US008304258B2

(12) United States Patent
Kulaksiz et al.

(10) Patent No.: US 8,304,258 B2
(45) Date of Patent: Nov. 6, 2012

(54) METHODS OF PRODUCING MONOCLONAL ANTIBODIES SPECIFIC FOR HUMAN HEPCIDIN

(75) Inventors: Hasan Kulaksiz, Ulm (DE); Cyril E. Geacintov, Mountainside, NJ (US); Alfred Janetzko, Butzbach (DE)

(73) Assignee: DRG International, Inc., Mountainside, NJ (US)

( * ) Notice: Subject to any disclaimer, the term of this patent is extended or adjusted under 35 U.S.C. 154(b) by 0 days.

(21) Appl. No.: 13/215,665

(22) Filed: Aug. 23, 2011

(65) Prior Publication Data

US 2012/0003696 A1 Jan. 5, 2012

Related U.S. Application Data

(60) Division of application No. 11/657,772, filed on Jan. 25, 2007, now Pat. No. 8,017,737, which is a continuation-in-part of application No. 10/441,089, filed on May 19, 2003, now Pat. No. 7,320,894, which is a continuation-in-part of application No. 10/299,486, filed on Nov. 19, 2002, now Pat. No. 7,411,048.

(51) Int. Cl.
G01N 33/53 (2006.01)
A61K 39/395 (2006.01)
C07K 16/00 (2006.01)
C12P 21/08 (2006.01)

(52) U.S. Cl. .................. 436/548; 424/141.1; 530/388.1; 530/808

(58) Field of Classification Search .................. None
See application file for complete search history.

(56) References Cited

U.S. PATENT DOCUMENTS

| | | | |
|---|---|---|---|
| 4,464,465 A | 8/1984 | Lostrom | |
| 5,420,016 A | 5/1995 | Boguslaski et al. | |
| 5,753,230 A | 5/1998 | Brooks et al. | |
| 7,320,894 B2 | 1/2008 | Kulaksiz et al. | |
| 7,411,048 B2 | 8/2008 | Kulaksiz et al. | |
| 8,017,737 B2 | 9/2011 | Kulaksiz et al. | |
| 2002/0091247 A1 | 7/2002 | Kaser et al. | |
| 2003/0027999 A1 | 2/2003 | Rosen et al. | |
| 2004/0096990 A1* | 5/2004 | Geacintov et al. | 436/518 |
| 2004/0234527 A1 | 11/2004 | Crisanti | |
| 2005/0037971 A1 | 2/2005 | Nicolas et al. | |
| 2007/0124825 A1 | 5/2007 | Nicolas et al. | |
| 2007/0134746 A1 | 6/2007 | Kulaksiz et al. | |

FOREIGN PATENT DOCUMENTS

| | | |
|---|---|---|
| WO | 00/73454 A1 | 12/2000 |
| WO | 02/098444 A2 | 12/2002 |

OTHER PUBLICATIONS

Subramaniam et al., (2002) Cell Biochem. Biophys. 36, 235-239.

Brugnara, Carlo; "Iron Deficiency and Erythropoiesis: New Diagnostic Approaches,"; Clinical Chemistry 2003; vol. 49, No. 10, pp. 1573-1578.
Nemeth et al.; "Hepcidin, a putative mediator of anemia of inflammation, is a type II acute-phase protein,"; Blood, Apr. 1, 2003; vol. 101, No. 7, pp. 2461-2463.
Swinkels et al.; "Hereditary hemochromatosis: genetic complexity and new diagnostic approaches,"; Clinical Chemistry 2006; vol. 52, No. 6, pp. 950-968.
Ashurst, P.R., Dennis, M.J., Analytical Methods of Food Authentication, 1998, p. 253, Blackie Academic and Professional, Thomson Science, London, UK.
Garcia-Beato, R., Melero, J.A., The C-terminal third of human respiratory syncytial virus attachment (G) protein is partially resistant to protease digestion and is glycosylated in a cell-type-specific manner, J. General Virology, 2000, pp. 917-927,vol. 81, UK.
Tang, R., et al. Epitope Mapping of Monoclonal Antibody to Integrin aLb2 Hybrid Domain Suggests Different Requirements of affinity States for Intercellular Adhesion Molecules (ICAM)-1 and ICAM-3 Binding, j. Biological Chemistry, Aug. 12, 2005, pp. 29208-29216, vol. 280, No. 32, The american Society for Biochemistry and Molecular Biology, USA.
Anderson et al., "Iron Absorption and Metabolism," Current Opinion in Gastroenterology (2009) vol. 25: pp. 129-135.
Nemeth et al., "Hepcidin, a putative mediator of anemia of inflammation, is a type II acute-phase protein," Blood (Apr. 1, 2003) vol. 101, No. 7: pp. 2461-2463.
Swinkels, et al., "Hereditary Hemochromatosis: Genetic Complexity and New Diagnostic Approaches," Clinical Chemistry (2006) 52:6, pp. 950-968.
Darst et al., "Adsorption of the protein antigen myoglobin affects the binding of conformation-specific monoclonal antibodies,"; Biophysical Journal (1988): vol. 53, pp. 533-539.
Declaration of Alfred Janetzko, Ph.D., Dec. 23, 2009.
Strongin, Laboratory Diagnosis of Viral Infections, Sensitivity, Specificity, and Predictive Value of Diagnostic Tests: Definitions and Clinical applications, Lennette, ed. Marcel Dekker, Inc. New York, pp. 211-219, 1992.

(Continued)

Primary Examiner — Robert Landsman
(74) Attorney, Agent, or Firm — Fox Rothschild LLP; Gerard P. Norton

(57) ABSTRACT

The present invention concerns antibodies specific for the C-terminus of human hepcidin, and related methods and kits for diagnosing and/or treating a disease condition characterized by non-physiological levels of hepcidin protein, including prohepcidin and fragments thereof, comprising obtaining a tissue or fluid sample from a subject; contacting the sample with an antibody or fragment thereof that specifically binds to a polypeptide corresponding to the amino acid sequence between and including amino acids 60 and 84, or, in another embodiment, amino acids 74 and 81, as aligned with the human pre-pro-hepcidin precursor protein, and quantifying the pro-hepcidin and/or mature hepcidin level using an assay based on binding of the antibody and the polypeptide; wherein the non-physiological level of prohepcidin/mature hepcidin is indicative of the disease condition. The present invention also concerns diagnostic methods and kits for applications in genetic technological approaches, such as for over-expressing or downregulating hepcidin.

7 Claims, 18 Drawing Sheets

OTHER PUBLICATIONS

Ashurst, P.R., Dennis, M.J., "Analytical Methods of Food Authentication," Blackie Academic and Professional, Thomson Science, London, UK (1998) p. 253.

Garcia-Beato, R., Melero, J.A., The C-terminal third of human respiratory syncytial virus attachment (G) protein is partially resistant to protease digestion and is glycosylated in a cell-type-specific manner, J. General Virology, 2000, pp. 919-927,vol. 81, UK.

Tang, R. et al, Epitope Mapping of Monoclonal Antibody to Integrin aLb2 Hybrid Domain Suggest Different Requirements of affinity States for intercellular Adhesion Molecules (ICAM)-1 and ICAM-3 Binding, j. Biological Chemistry, Aug. 12, 2005, pp. 29208-29216, vol. 280, No. 32, The American Society for Biochemistry and Molecular biology, USA.

Office Action issued on Apr. 14, 2010 for U.S. Appl. No. 12/629,263.
Office Action issued on Oct. 28, 2008 for U.S. Appl. No. 11/526,997.
Wild, The Immunoassay Handbook, Stockton Press, 1994, p. 66.
Diamandis et al., Immunoassay, Academic Press, Chapter 11, The Avidin-Biotin System, pp. 237-255, 1996.
Andrews, N.C. (2000) Annu. Rev. Genomics Hum. Genet. 1, 75?98.
Philpott, C.C. (2002) Hepatology 35, 993-1001.
Beutler et al., (2001) Drug?Metab. Dispos. 29, 495?499.
Collawn et al., (1990) Cell 63, 1061?1072.
Kawabata et al., (1999) J. Biol. Chem. 274, 20826-20832.
Camasehella et al., (2000) Nat. Genet. 25, 14-15.
Fleming et al., (2002) Proc. Natl. Acad. Sci. USA 99, 10653?10658.
Fleming et al., (2000) Proc. Natl. Acadi. Sci. USA 97, 2214-2219.
Subramaniam et al., (2002) Cell Biochem. Biophys. 36, 235?239.
Krause et al., (2000) FEBS Lett. 480, 147-150.
Park et al., (2001) J. Biol. Chem. 276, 7806-7810.
Nicolas et al., (2002) Proc. Natl. Acad. Sci. USA 99, 4396-4601.
Pigeon et al., (2001) J. Biol. Chem. 276, 7811-7819.
Nicolas et al., (2001) Proc. Natl. Acad. Sci. USA 98, 8780?8785.
Kulaksiz et al., (2002) Proc. Natl. Acad. Sci. USA 99, 6796-6801.
Kulaksiz et al., (2002) Am. J. Pathol. 161, 655-664.
Rost et al., (1999) Hepatology 29, 814-821.
Hunter et al., (2002) J. Biol. Chem., M205305200.
Kawabata et al., (2000) J. Biol. Chem. 275, 16618-16625.
Frazer et al., (2002) Gastroenterology 123, 835-844.
Aden et al., (1979) Nature 282, 615-616.
Schwartz et al., (1985) EMBO J. 4, 899-904.
Zhou et al., (1998) Proc. Natl. Acad. Sci. USA 95, 2492-2497.
Levy et al., (1999) Blood 94, 9-11.
Santos et al., (1996) J. Exp. Med. 184, 1975?1985.
Anderson et al., (2002) Biochem. Soc. Trans. 30, 724-726.
UniProtKB/Swiss-Prot entry Q5U9D2 HEPC CANFA, pp. 1-3, Jun. 28, 2006.
UniProtKB/Swiss-Prot entry P81172 HEPC Human, pp. 1-3, Jun. 28, 2006.
UniProtKB/Swiss-Prot entry Q8MJ80, HEPC Pig, pp. 1-3, Jun. 28, 2006.
UnitProtKB/Swiss-Prot entry Q9EQ21, HEPC Mouse, pp. 1-4, Jun. 28, 2006.
Wild et al., The Immunoassay Handbook, Chapter 2, Components, pp. 49-54, 1994.
Andrews, N.C. (2000) Annu. Rev. Genomics Hum. Genet. 1, 75-98.
Beutler et al., (2001) Drug-Metab. Dispos. 29, 495-499.
Collawn et al., (1990) Cell 63, 1061-1072.
Fleming et al., (2002) Proc. Natl. Acad. Sci. USA 99, 10653-10658.
Nicolas et al., (2001) Proc. Natl. Acad. Sci. USA 98, 8780-8785.
Santos et al., (1996) J. Exp. Med. 184, 1975-1985.

* cited by examiner

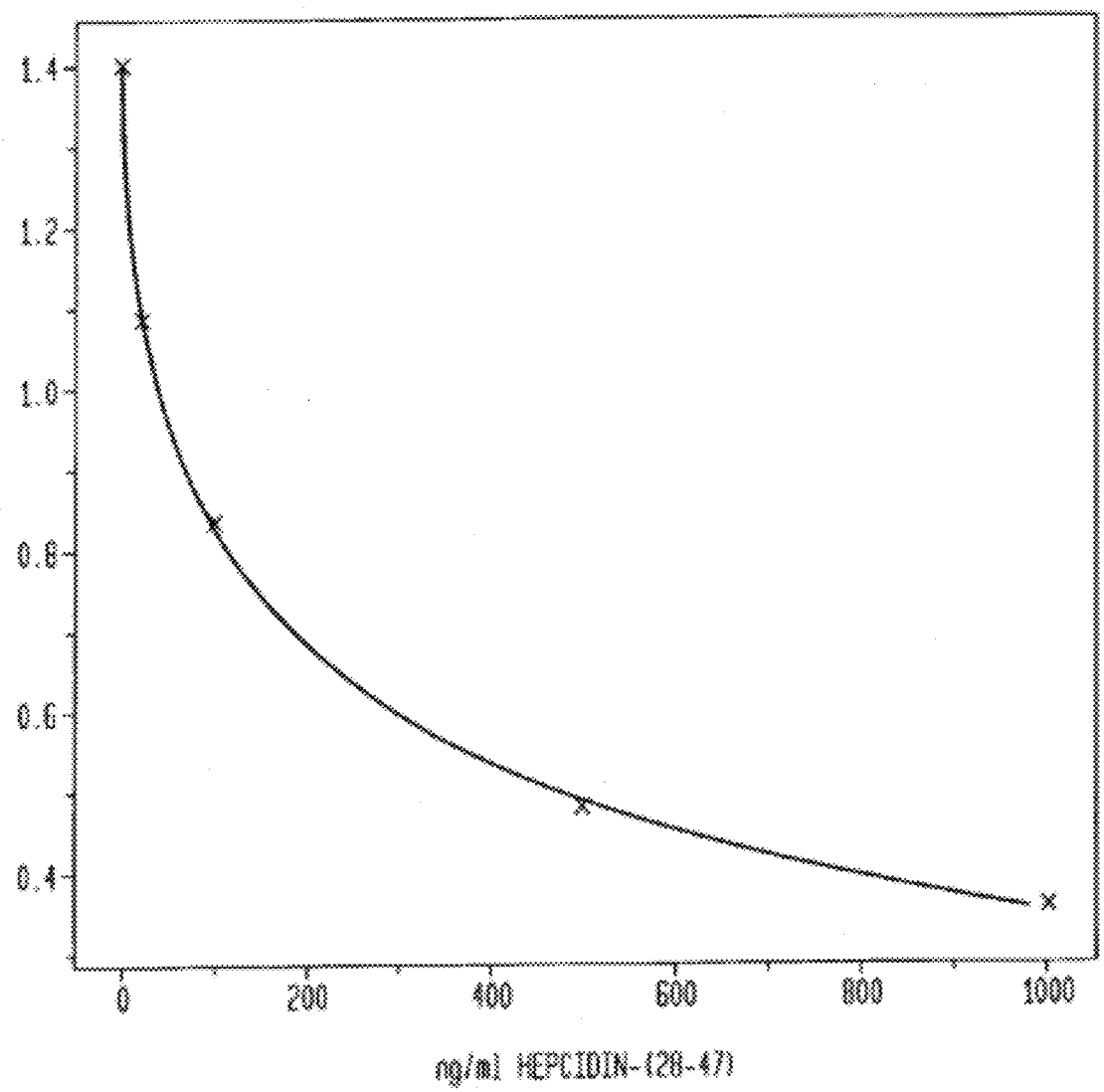

FIG. 7

(SEQ ID NO. 6)

```
gactgtcact cggtcccaga caccagagca agctcaagac ccagcagtgg gacagccaga  60
cagacggcac gatggcactg agctcccaga tctgggccgc ttgcctactg ctcctcctcc 120
tcctcgccag cctgaccagt ggctctgttt tcccacaaca gacgggacaa cttgcagagc 180
tgcaacccca ggacagagct ggagccaggg ccagctggat gccatgttc cagaggcgaa 240
ggaggcgaga caccccactc cccatctgca ttttctgctg cggctgctgt catcgatcaa 300
agtgtgggat gtgctgcaag acgtagaacc tacctgccct gccccgtcc cctcccttcc 360
ttatttattc ctgctgcccc agaacatagg tcttggaata aaatggctgg ttcttttgtt 420
ttccaaaaaa                                                        430
```

(SEQ ID NO. 7)

```
malssqiwaa clllllllas ltsgsvfpqq tgqlaelqpq dragaraswm pmfqrrrrrd  60
thfpicifcc gcchrskcgm cckt                                         24
```

FIG. 13
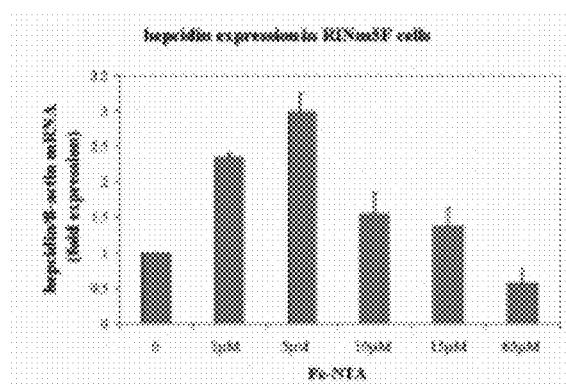
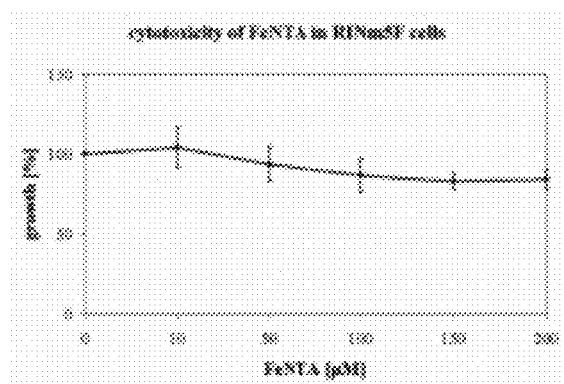
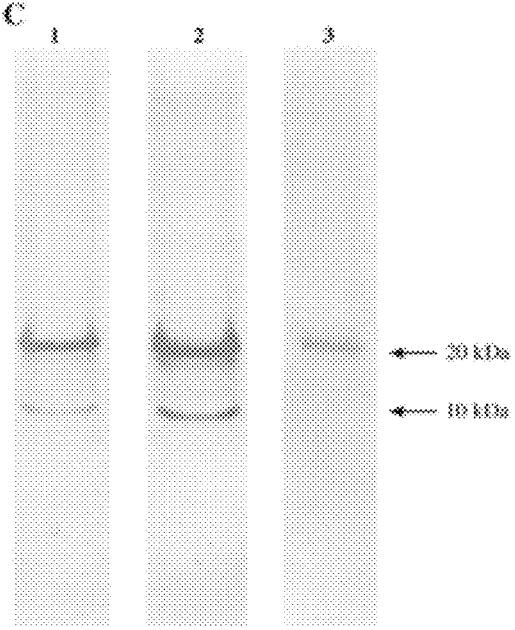

FIG. 14
A
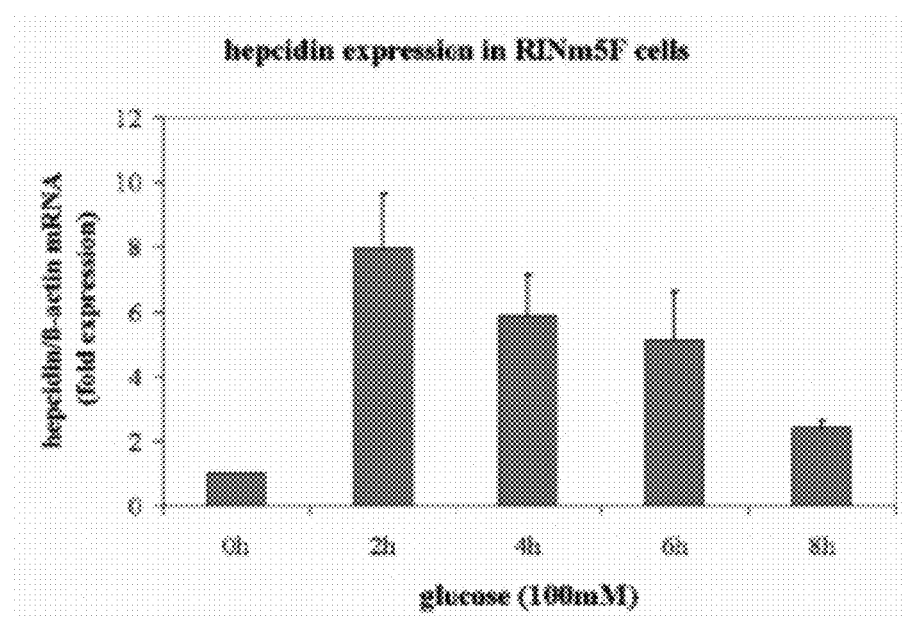
B
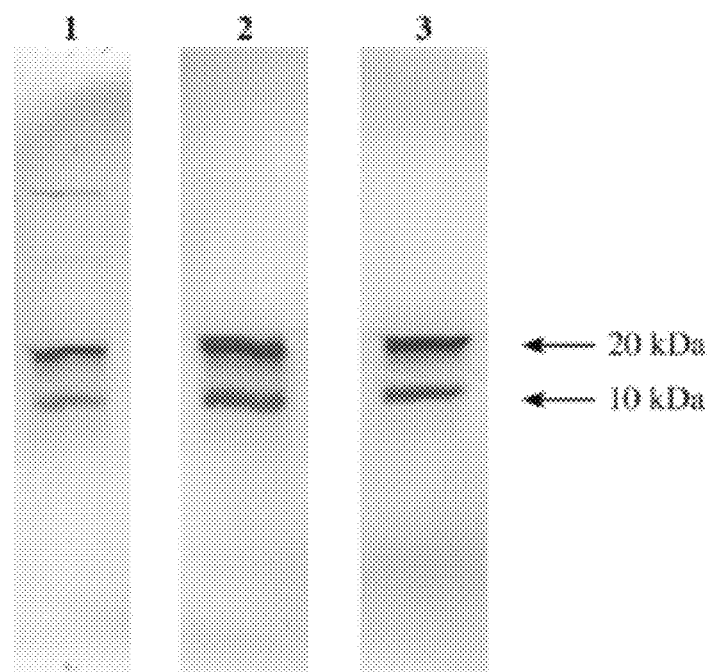

METHODS OF PRODUCING MONOCLONAL ANTIBODIES SPECIFIC FOR HUMAN HEPCIDIN

CROSS-REFERENCE TO RELATED APPLICATIONS

This application is a Divisional of U.S. patent application Ser. No. 11/657,772 filed on Jan. 25, 2007, now U.S. Pat. No. 8,017,737, which is a Continuation-in-Part of application Ser. No. 10/441,089 filed on May 19, 2003, now U.S. Pat. No. 7,320,894, which is a Continuation-in-Part of application Ser. No. 10/299,486 filed Nov. 19, 2002, now U.S. Pat. No. 7,411,048.

FIELD OF THE INVENTION

The present invention concerns methods and kits for diagnosing a disease condition characterized by non-physiological levels of hepcidin protein. The present invention further concerns monoclonal antibodies that interact specifically with the mature form of human hepcidin (hepcidin-25). Multiple forms of these isolated antibodies are disclosed and exemplified herein. The present invention further concerns methods of treating any disease condition within a patient that is characterized by such non-physiological levels of hepcidin protein.

BACKGROUND OF THE INVENTION

Iron is an essential trace element that is required for growth and development of all living organisms. It is indispensable for DNA synthesis and is an essential component of many proteins and enzymes including haemoglobin and myoglobin, the cytochromes, NADH dehydrogenase, lipooxygenases, phosphatases, superoxide dismutase, ribonucleotide reductase, and fatty acid desaturases.

Iron can also be toxic when present in excess because of its ability to generate reactive oxygen species. This dual nature imposed a very tight regulation of the iron concentration in the body. Disturbances in iron metabolism are implicated in a number of significant human diseases, including anemia of chronic diseases, anemia of inflammation, or the iron overload disease hemochromatosis.

In mammals, iron absorption occurs predominantly in the duodenum and upper jejunum, and systemic iron homeostasis is regulated at the level of intestinal absorption and this is the only mechanism by which iron stores are physiologically controlled (Philpott, *Hepatology* 35:993-1001 2002). Following absorption, iron is bound to circulating transferrin and delivered to tissues throughout the body. The liver is the major site of iron storage. There, transferrin-bound iron is taken into the hepatocytes by receptor-mediated endocytosis via the classical transferring receptor (TfR1) (Collawn et al., *Cell* 63: 1061-1072, 1990) and presumably in greater amounts via the recently identified homologous transferrin receptor 2 (TfR2) (Kawabata et al., *J. Biol. Chem.* 274: 20826-20832, 1999). The extracellular domain of this protein is 45% identical to the corresponding portion of TfR1 (Id.). TfR2 can also bind diferric transferrin and facilitate the uptake of iron. Mutations in TfR2 have been associated with certain forms of hemochromatosis demonstrating the important role for TfR2 in iron homeostasis (Philpott, *Hepatology* 35:993-1001, 2002; Camasehella et al., *Nat. Genet.* 25:14-15, 2000; Fleming et al. *Proc. Natl. Acad. Sci. USA* 99: 10653-10658, 2002). TfR2 is predominantly expressed in the liver (Fleming et al., *Proc. Natl. Acad. Sci. USA* 97: 2214-2219, 2000; Subramaniam et al., *Cell Biochem. Biophys.* 36:235-239, 2002), and is localized in the basolateral membrane domain of hepatocytes. (Merle et al., *Histochem. Cell. Biol.*, 2006.)

Maintenance of stable extracellular iron concentrations requires the coordinate regulation of iron transport into plasma from dietary sources in the duodenum, from recycled senescent red cells in macrophages and from storage in hepatocytes.

Hepcidin is a recently discovered peptide hormone (Park et al., *J. Biol. Chem.* 276:7806-7810, 2001; Krause et al., *FEBS Letter* 480:147-150, 2000), which is the key regulator of systemic iron homeostasis. Hepcidin is predominantly produced in the liver (Park et al. *J. Biol. Chem.* 276:7806-7810, 2001; Kulaksiz et al. GUT 53:735-43, 2004), circulates in plasma and is excreted in urine (Kulaksiz et al., *J. Endocrinol.* 184, 2005). It is encoded by a small three-exon gene as a preprohepcidin with a characteristic signal sequence and a furin cleavage site preceding the mature hepcidin peptide. The active form of the peptide is a 25 amino acid β-sheet hairpin stabilized by four disulfide bonds. It is synthesized as a preprohepcidin of 84 amino acids. The signal peptide is cleaved leading to the 60 amino acids prohepcidin, which is further processed giving rise to the 25 amino acids hepcidin. In human urine, the predominant form is the 25 amino acid peptide, although shorter peptides with 20 and 22 amino acids are also detectable.

The involvement of hepcidin in iron metabolism was suggested by the observation that hepcidin synthesis is induced by dietary iron (Pigeon et al. *J. Biol. Chem.* 276:7811-7819, 2001). The specific role of hepcidin was then examined by assessing the effects of its deficiency or excess in transgenic mouse models. Hepcidin expression is abolished in mice exhibiting iron overload due to targeted disruption of the upstream stimulatory factor 2 (Usf2) gene, resembling the same phenotype as found in hfe−/− mice (Nicolas et al., *Proc. Natl. Acad. Sci. USA* 98:8780-8785, 2001). In contrast, overexpression of hepcidin was shown to result in severe iron deficiency anemia in transgenic mice (Nicolas et al., *Proc. Natl. Acad. Sci. USA* 99:4396-4601, 2002), indicating that hepcidin is a central regulator of iron homeostasis. Moreover, recent studies have shown that liver hepcidin expression is decreased in the hfe knockout mouse (Ahmad et al., *Blood Cells Mol. Dis.* 29, 2002), and mutations in the hepcidin peptide are associated with severe juvenile hemochromatosis (Roetto et al., *Nat. Genet.* 33, 2003), providing new perspectives in our understanding of the molecular pathogenesis of iron overload.

Recent studies indicate that hepcidin inhibits cellular efflux of iron by binding to ferroportin (Nemeth et al. *Science* 306: 2090-2093, 2004), the only known mammalian iron exporter, which is expressed by enterocytes, macrophages and hepatocytes. The binding of hepcidin causes ferroportin to be internalized and degraded, and the loss of ferroportin from cell membrane ablates cellular iron export. The direct hepcidin-ferroportin interaction allows an adaptive response from the body in situations that alter normal iron homeostasis (hypoxia, anemia, iron deficiency, iron overload, and inflammation).

This mechanism explains the regulation of iron absorption. When iron stores are adequate or high, the liver produces hepcidin which circulates to the duodenum, where hepcidin causes internalization of ferroportin, blocking the sole pathway for the transfer of iron from the enterocytes to plasma. When iron stores are low, hepcidin production is suppressed, and ferroportin molecules are displayed on basolateral membranes of enterocytes, transporting iron from enterocyte to plasma (Ganz, *Best Prac. & Res. Clin. Haem.* 18, 2005). Most of the iron absorbed from the diet or recycled from haemoglobin is destined for developing erythrocytes. It is therefore not surprising that hepcidin production is homeostatically regulated by anemia and hypoxemia (Nicolas et al., *J. Clin. Invest.* 110, 2002). When oxygen delivery is inadequate, the homeostatic response is to produce more erythrocytes. Thus, in anemia, hepcidin levels decrease, its inhibitory effects diminish, and more iron is made available from the diet and from the storage pool in macrophages and hepatocytes.

Hepcidin, as an iron-regulatory hormone, constitutes an important link between host defense, inflammation and iron metabolism. Hepcidin is structurally similar to cysteine rich, cationic, antimicrobial peptides, including the defensins and some cathelicidins. In vitro, human hepcidin exerts antimicrobial and antifungal activities (Park et al., *J. Biol. Chem.* 276:7806-7810, 2001; Krause et al., *FEBS Letter* 480:147-150, 2000). Its synthesis is markedly induced by infection and inflammation (Pigeon et al., *J. Biol. Chem.* 276: 7811-7819, 2001; Nemeth et al., 101, *Blood* 2003; Nicolas et al., *J. Clin. Invest.* 110, 2002), trapping iron in macrophages, decreasing plasma iron concentrations and causing iron-restricted erythropoiesis characteristic of anemia of inflammation.

The cytokine IL-6 is apparently the key inducer of hepcidin synthesis during inflammation (Nemeth et al., *J. Clin. Invest.* 113, 2004) and anti-IL-6 antibodies block the induction of hepcidin mRNA in human hepatocyte cell lines treated with supernatants of LPS- or peptidoglycan-stimulated macrophages. During inflammation induced by subcutaneous injections of turpentine, normal mice show a marked decrease in serum iron (Nicolas et al., *J. Clin. Invest.* 110, 2002; Nemeth et al., *J. Clin. Invest.* 113, 2004). This response is completely ablated in hepcidin-deficient mice and in IL-6-deficient mice. In humans, the hepcidin increase elicited by IL-6 infusion is accompanied by a decrease in serum iron and transferring saturation of more than 30% (Nemeth et al., *J. Clin. Invest.* 113, 2004; Ganz, *Best Prac & Res Clin Haem* 18, 2005).

The key role of hepcidin in iron homeostasis and its disorders suggests that its assay in blood or urine could prove useful for the diagnosis and monitoring of iron disorders. Furthermore, hepcidin could be a marker for disease activity of chronic inflammatory diseases such as, for example, chronic polyarthritis or Crohn's disease, or ulcerative colitis. At this time, only an assay for pro-hepcidin is available (Kulaksiz et al., *GUT* 53: 735-43, 2004; see also co-pending related U.S. patent application Ser. No. 10/441,089, filed May 19, 2003 and Ser. No. 10/299,486, filed Nov. 19, 2002). Further development of reliable plasma and urine assays for hepcidin is highly desirable (Ganz, *Best Prac. & Res. Clin. Haem.* 18, 2005). However, production of specific antibodies against hepcidin was not possible due to the complicated structure of hepcidin (Ganz, *Best Prac. & Res. Clin. Haem.* 18, 2005; Kulaksiz et al., *GUT* 53: 735-43, 2004; Hugman, *Clin. Lab. Haem.* 28, 2006).

Thus, there is a need for improvements in methods and kits useful for the diagnosis and monitoring of disease conditions characterized by non-physiological levels of hepcidin protein.

SUMMARY OF THE INVENTION

The invention addresses drawbacks of the prior art by providing, in one aspect, sensitive methods and kits for diagnosing a disease condition characterized by non-physiological levels of hepcidin protein. To this end, a portion of the present invention relates to an antibody or antibody fragment which interacts with a specific region of a mature form of human hepcidin-25, namely amino acids 74-81 of hepcidin-25, represented as His Arg Ser Lys Cys Gly Met Cys (SEQ ID NO:3). The present invention further relates to an antibody raised against a specific region of mature human hepcidin-25 which comprises the region from amino acid 74-81, wherein amino acid residue 78 is Xaa (His Arg Ser Lys Xaa Gly Met Cys [SEQ ID NO:4]), where Xaa is any known amino acid, including L or D stereoisomeric forms of the 20 common amino acids, as well as any modified or unusual amino acid available to the artisan. In an embodiment exemplified herein, amino acid residue 78 is alpha aminobutyric acid (His Arg Ser Lys Abu Gly Met Cys [SEQ ID NO:5]).

In one embodiment, the present invention relates to a monoclonal antibody or fragment thereof which interacts with a specific region of human hepcidin-25 (again, amino acids 74-81 of hepcidin-25, represented as His Arg Ser Lys Cys Gly Met Cys [SEQ ID NO:3]). Therefore, the present invention relates to a monoclonal antibody raised against a specific region of human hepcidin-25 which comprises the region from amino acid 74-81, wherein amino acid residue 78 is Xaa (His Arg Ser Lys Xaa Gly Met Cys [SEQ ID NO:4]), as disclosed herein. Again, an exemplified peptide susbstitutes alpha aminobutyric acid for cysteine (His Arg Ser Lys Abu Gly Met Cys [SEQ ID NO:5]), which was used as an immunogen to generate the exemplified monoclonal antibodies described herein.

The present invention also relates to a hybridoma capable of producing a monoclonal antibody of the present invention. Particular hybridomas of the present invention are hybridomas which produce monoclonal antibodies mHK(5), mHK (8/1), mHK(8/2), mHK(8/3) and mHK(9), respectively. Hybridoma mHK(9) was deposited in the DSMZ—Deutsche Sammlung von Mikroorganismen und Zellkulturen GmbH (DSMZ), Mascheroder Weg 1b, D-38124 Braunschweig, Germany on Feb. 7, 2007, as was assigned accession number DSM ACC2812. The deposit was made under the requirements of the Budapest Treaty on the International Recognition of the Deposit of Microorganisms for the Purposes of Patent Procedure.

The antibodies of the present invention may also be in the form of a polyclonal sera raised against this specific region of human hepcidin-25, especially polyclonal sera raised against this core sequence comprising at least amino acid residues 74-81 (His Arg Ser Lys Cys Gly Met Cys [SEQ ID NO:3]), His Arg Ser Lys Xaa Gly Met Cys [SEQ ID NO:4], and/or His Arg Ser Lys Abu Gly Met Cys [SEQ ID NO:5]).

The present invention further relates to a peptide which comprises the amino acid sequence shown as His Arg Ser Lys Cys Gly Met Cys (SEQ ID NO:3).

The present invention also relates to a peptide which comprises the amino acid sequence shown as His Arg Ser Lys Xaa Gly Met Cys (SEQ ID NO:4), where Xaa is any known amino acid, including L or D stereoisomeric forms of the 20 common amino acids, as well as any modified or unusual amino acid available to the artisan.

The present invention also relates to a peptide which comprises the amino acid sequence shown as His Arg Ser Lys Abu Gly Met Cys (SEQ ID NO:5), where amino acid residue 78 is alpha aminobutyric acid.

The present invention also relates to a peptide which consists of the amino acid sequence selected from the group consisting of SEQ ID NO:3, SEQ ID NO:4 and SEQ ID NO:5.

The present invention also relates to methods of generating antibodies specific for mature human hepcidin which comprises immunizing a non-human animal with a C-terminal hepcidin peptide which comprises the amino acid sequence as shown in of SEQ ID NO:3, SEQ ID NO:4, and/or SEQ ID NO:5.

The present invention further relates to methods and assays for quantitatively determining hepcidin levels, which comprises obtaining a tissue or fluid sample from a subject; contacting the sample with an antibody or fragment thereof that specifically binds to a peptide selected from the group consisting of SEQ ID NO:3, SEQ ID NO:4, and/or SEQ ID NO:5, and quantifying the hepcidin level in the sample; wherein the non-physiological level of hepcidin is indicative of the disease condition.

The present invention thus relates to kits for quantitatively determining hepcidin levels, which comprises obtaining a tissue or fluid sample from a subject; contacting the sample with an antibody or fragment thereof that specifically binds to a peptide selected from the group consisting of SEQ ID NO:3, SEQ ID NO:4, and/or SEQ ID NO:5, and quantifying the hepcidin level in the sample; wherein the non-physiological level of hepcidin is indicative of the disease condition.

The present invention also relates to methods, assays and kits for quantitatively determining prohepcidin and/or mature hepcidin levels, which comprises obtaining a tissue or fluid sample from a subject; contacting the sample with an antibody or fragment thereof that specifically binds to one or more epitopes of human hepcidin precursor amino acid sequence between and including amino acids 74-81 (i.e., SEQ ID NO:3), and quantifying the hepcidin level in the sample; wherein the non-physiological level of hepcidin is indicative of the disease condition.

The present invention also relates to methods, assays and kits for quantitatively determining hepcidin levels, which comprises obtaining a tissue or fluid sample from a subject; contacting the sample with an antibody or fragment thereof that specifically binds to one or more epitopes of human hepcidin precursor amino acid sequence between and including amino acids 60-84 (i.e., SEQ ID NO:2), and quantifying the hepcidin level in the sample; wherein the non-physiological level of hepcidin is indicative of the disease condition. Thus, the present invention concerns hepcidin regulation of iron uptake by mammalian cells and the use of hepcidin and/or hepcidin specific antibodies in the diagnosis of diseases involving disturbances of iron metabolism. The diagnostic detection kits of the present invention can be particularly useful in screening the overall population of either humans or animals and identifying those subjects who have these diseases. To this end, one aspect of the invention relates to a method for diagnosing a disease condition characterized by non-physiological levels of hepcidin, comprising obtaining a tissue or fluid sample from a subject; contacting the sample with an antibody or fragment thereof that specifically binds to a polypeptide from the mid-portion (amino acids 20 to 50, SEQ ID NO:1) or C-terminus of hepcidin (amino acids 60 to 84, SEQ ID NO:2, such as a region of the human hepcidin protein comprising amino acids 74-81 (His Arg Ser Lys Cys Gly Met Cys [SEQ ID NO:3]), and quantifying the hepcidin level using an assay based on binding of the antibody and the polypeptide; wherein the non-physiological level of hepcidin is indicative of the disease condition. In one aspect of the present invention, sensitive diagnostic methods and kits were established enabling the detection of pro-hepcidin in human plasma. In another aspect of the present invention, sensitive diagnostic methods and kits were established enabling the detection of mature hepcidin (e.g., HEPCIDIN-25, HEPCIDIN-22, and/or HEPCIDIN-20; see FIG. 8) in human plasma, urine and other body fluids. The invention opens a broad range of therapeutic perspectives, where a hepcidin antibody and diagnostic methods (e.g., HEPCIDIN-25, HEPCIDIN-22, and/or HEPCIDIN-20; again, see FIG. 8) and kits can be used for the determination of hepcidin as a parameter for the progress of the diseases mentioned above during and after therapy.

This invention further provides the demonstration that a hepcidin protein in subjects of these disorders are present in human or animal tissue, blood and body fluids in concentrations greatly exceeding that found in normal humans or animals that are not subjects of these disorders. This is achieved by examining a sample of tissue, blood or body fluid from a patient, and detecting the presence and quantity of hepcidin protein, including but not limited to prohepcidin or any mature form of hepcidin, such as hepcidin-25, or a 22- or 20-amino acid version of mature hepcidin (see FIG. 8). The detection and quantitative measurement of any hepcidin protein or fragment thereof in tissue, blood or body fluids in accordance with this invention is useful in confirming a clinical diagnosis of the diseases described herein, in affected patients and in following the course of the disease. The invention is also useful in monitoring the disease during and subsequent to a period of treatment with agents that are being tested for their ability to stabilize, decrease or prevent the occurrence of such diseases.

This discovery has permitted the development of monoclonal antibodies against hepcidin and assays for a hepcidin protein and fragments thereof. These antibodies and assays allow for the first time the determination of hepcidin levels in the following diseases and treatment of diseases with monoclonal hepcidin antibodies to block hepcidin activity.

Nonphysiological amounts of the hepcidin protein or a fragment thereof can exist in disturbances of iron metabolism, resulting in iron deficiency or overload, such as iron deficiency anemia, genetic and nongenetic iron overload diseases, such as hemosiderosis and hemochromatosis or secondary hemochromatosis, aceruloplasminemia, hypotransferrinemia, atransferrinemia; iron overload diseases of undetermined origin, for instance in the case of diseases of the biliary system, liver diseases, especially alcoholic liver diseases, nonalcoholic steatohepatitis, and chronic hepatitis B and C infections; diseases of utilization of iron, such as sideroblastic anemia, thalassemia; hematologic diseases, such as leukemia, polyglobulie, macrocytic, microcytic or normocytic anemia, anemia with reticulocytosis, hemolytic anemia; disturbances of the reticuloendothelial system due to infections and diseases; inflammations and infections, including sepsis; immunologic diseases and tumors, such as carcinoma, sarcoma, lymphomas that result in non-physiologic hepcidin concentrations; neurodegenerative diseases, such as Alzheimer's disease and Wilson's disease, renal anemia, anemia of chronic diseases, anemia in Crohns disease, anemia in ulcerative colitis, sprue, cholangitis, primary or secondary sclerosing cholangitis, chronic polyarthritis, thalassemia, and iron overload after iron substitution or after erythropoietin therapy. To this end, the present invention relates to use of the antibodies of the present invention in methods of diagnosis, related assays and kits for such diagnosis, as well as therapeutic intervention of various disease states disclosed herein.

One embodiment of the invention concerns the generation and purification of a hepcidin protein and fragments thereof. Another embodiment of the invention concerns hepcidin specific antibodies, or fragments or variants thereof that, in turn, can be used in immunoassays to detect a hepcidin protein in suspected humans or animals.

In another aspect of the invention, the hepcidin diagnostic methods and kits can be used in genetic technological approaches, such as for overexpressing or downregulating hepcidin.

In still another aspect of the invention, hepcidin can be used in therapeutic treatment of the diseases described herein, by treating subjects with hepcidin, and agonists or antagonists of hepcidin, including but not limited to monospecific antibodies, especially monospecific antibodies of the present invention which recognize one or more epitopes associated with amino acids 74-81 or human hepcidin (see FIG. 8). Iron uptake in cells may be modulated by varying the concentration of hepcidin, thus modulating binding between hepcidin and ferroportin. Accordingly, hepcidin, and agonists or antagonists of hepcidin may be useful in the treatment of conditions where there is a disturbance in iron metabolism. For example, such substances may be useful in the treatment of such aforementioned diseases. Depending on the disease condition, the therapeutic agent may comprise an antibody as mentioned above, including those discussed in the instant application, as well as antisense therapy (including RNAi, siRNA AND shRNA), or agents which alter blood glucose level, and any other molecule which possesses the ability to modulate hepcidin concentration, acting as either an agonist or antagonist of hepcidin concentration.

BRIEF DESCRIPTION OF THE DRAWINGS

FIG. 6 shows ELISA for circulating Pro-Hepcidin. A representative standard curve with concentrations of hepcidin-(28-47) in ng/ml and the extinction of the ELISA solution at 450 nm wavelength are shown. Note the high resolving power in the range of 1 to 400 ng/ml hepcidin-(28-47).

FIG. 7 shows the complete nucleotide (SEQ ID NO: 6) and amino acid sequences (SEQ ID NO: 7) of one form of hepcidin reproduced from GenBank database accession nos. NM021175 and AAH20612, respectively.

FIG. 13A-C shows that pancreatic hepcidin mRNA is regulated by iron. (A): Hepcidin expression in RINm5F cells after iron (FeNTA) stimulation using quantitative RT-PCR (n=5) (1 µM FeNTA: P<0.01; 3 µM: P<0.001; 10 µM: P<0.002; 65 µM: P<0.05). (B): Cytotoxicity of FeNTA in RINm5F cells measured by neutral red assay 3 days after iron stimulation. Note that no cytotoxicity exists under the iron concentrations used. (C): Immunoblot analysis of iron stimulated RINm5F cells showing hepcidin immunoreactivity at the range of 10 kDa. Note up-regulation of hepcidin with 3 µM FeNTA (2) and down-regulation with 65 µM FeNTA (3) compared to control (1). The second immunoreactive band at 20 kDa may reflect a dimeric type of hepcidin.

FIG. 14A-B shows hepcidin expression in β-cells is regulated by glucose. (A): Hepcidin expression in RINm5F cells after stimulation with glucose using quantitative RT-PCR (n=5) (2 h-8 h: P<0.01). (B): Immunoblot analysis of glucose-stimulated RINm5F cells showing up-regulation of hepcidin expression at 10 kDa after 2 h (2) and 4 h (3) glucose stimulation compared to control (1). Experiments were performed with 100 mM glucose. Stimulation of RINm5F cells with 25 mM glucose leads to the same results (not shown).

DETAILED DESCRIPTION OF THE INVENTION

The present invention describes that hepcidin regulates iron uptake by mammalian cells and nonphysiological express of hepcidin results in disease involved distribution of iron metabolism. Our preliminary data show that the physiological concentration of pro-hepcidin is in the range of 51.6-153.4 ng/mL (the mean concentration is about 106.2 ng/mL). Currently, it appears that nonphysiological concentrations are below or over this range. However, a person of the ordinary skill in the art will appreciate that as additional research is performed, these data may be modified. Nonphysiological amounts of prohepcidin and/or mature hepcidin protein or fragments thereof are associated with disturbances of iron metabolism, resulting in iron deficiency or overload, such as iron deficiency anemia; genetic and nongenetic iron overload diseases, such as hemosiderosis and hemochromatosis or secondary hemochromatosis, aceruloplasminemia, hypotransferrinemia, atransferrinemia; iron overload diseases of undetermined origin, for instance in the case of diseases of the biliary system, liver diseases, especially alcoholic liver diseases, nonalcoholic steatohepatitis, and chronic hepatitis B and C infections; diseases of utilization of iron, such as sideroblastic anemia, thalassemia; hematologic diseases, such as leukemia, polyglobulie, macrocytic, microcytic or normocytic anemia, anemia with reticulocytosis, hemolytic anemia; disturbances of the reticuloendothelial system due to infections and diseases; inflammations and infections, including sepsis; immunologic diseases and tumors, such as carcinoma, sarcoma, lymphoma, that result in non-physiologic hepcidin concentrations; neurodegenerative diseases, such as Alzheimer's disease and Wilson's disease. The clinical consequences of iron overload include cirrhosis of the liver and hepatocellular cancer, diabetes, heart failure, arthritis, and hypogonadism. Zhou et al., *Proc. Natl. Acad. Sci.*, 95, 2492-2497 (1998). Other suitable diseases include, without limitation, renal anemia, anemia of chronic diseases, anemia in Crohns disease, anemia in ulcerative colitis, sprue, cholangitis, primary or secondary sclerosing cholangitis, chronic polyarthritis, thalassemia, and iron overload after iron. This discovery has permitted the development of assays for a hepcidin protein and fragments thereof and their subsequent purification with retention of their native configuration and physiological activity. The invention is based, in part, on the discovery that in patients suffering from certain disorders a hepcidin protein is present in tissue, blood and body fluid of a human or animal. To this end, the present invention relates to use of the antibodies of the present invention in methods of diagnosis, related assays and kits for such diagnosis, as well as therapeutic intervention of various disease states disclosed herein.

Figure 8:
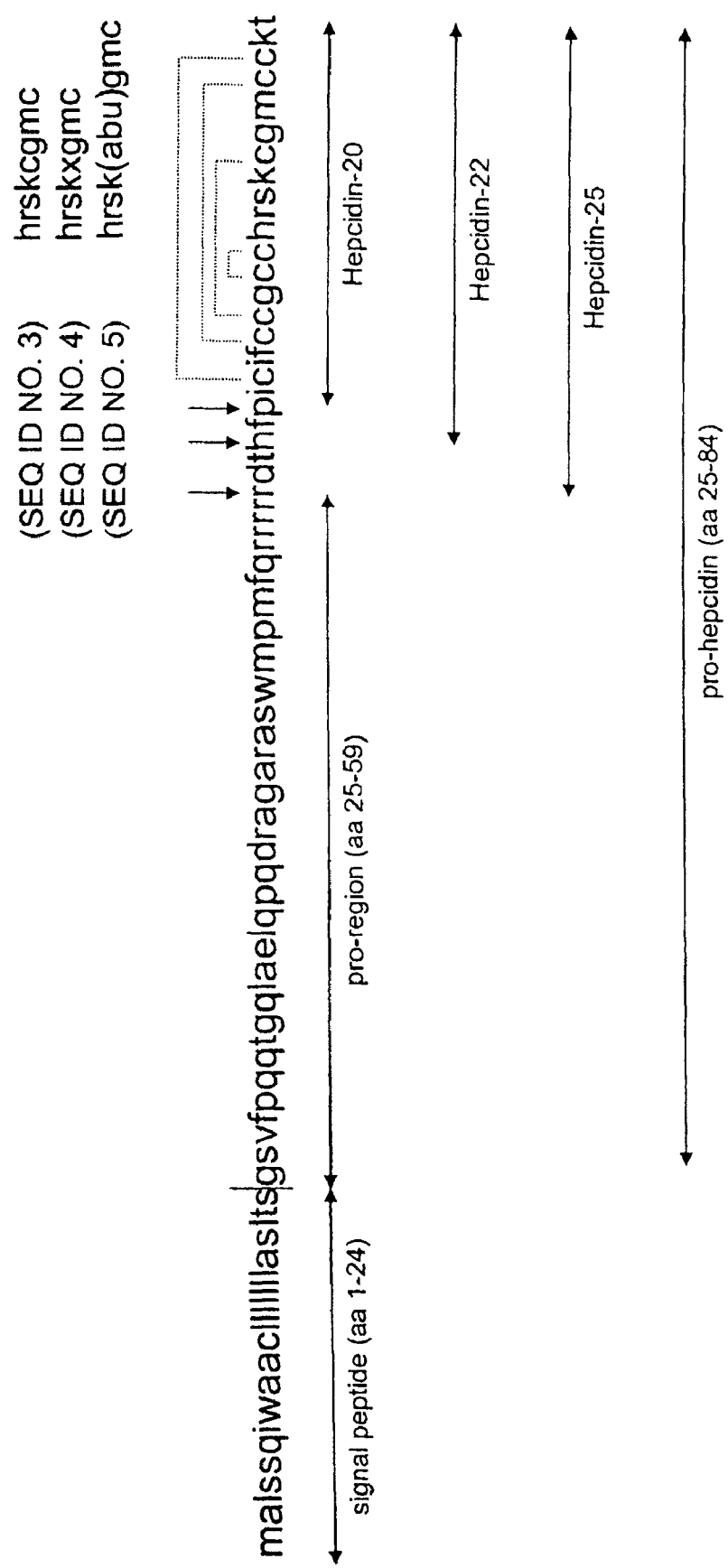
FIG. 8 shows the complete amino acid sequence of human pre-pro-hepcidin (amino acids 1-84[SEQ ID NO:8]), as well as the regions which represent pro-hepcidin (amino acids 25-84, contained within SEQ ID NO:8), the pro-region of hepcidin (amino acids 25-59, contained within SEQ ID NO:8), as well as the known mature forms of hepcidin [hepcidin-25 (amino acids 60-84, SEQ ID NO:2), hepcidin-22 [amino acids 63-84, contained within SEQ ID NO:2) and hepcidin-20 (amino acids 65-84, contained within SEQ ID NO:2)].

Further research of hepcidin's mechanism of action, as well as practical applications of the known information about hepcidin, have been hampered due to the lack of suitable antibodies recognizing both human pro-hepcidin and the 20-25 amino acid long mature hepcidin (i.e., amino acids 60-84 of human hepcidin [FIG. 8]). Co-pending patent applications U.S. patent application Ser. Nos. 10/299,486 and 10/441,089 respectively, teach novel antibodies binding to the mid-portion of pro-hepcidin. However, the production of antibodies useful in various ELISA applications which specifically bind to one or more epitopes in the C-terminus of human hepcidin protein has not been straightforward due to the fact that eight of the 25 amino acids in the mature 25 amino acid long hepcidin protein are cysteine residues, which are known to form disulfide bridges. Accordingly, there has been great difficulty in the art to find suitable immunogenic epitopes within that region.

The present invention solves this need of the art and further discloses novel antibodies which specifically bind to an epitope within the C-terminus of human hepcidin protein. These antibodies are advantageous compared to the prior art in at least two respects. First, the antibodies of the instant invention are suitable for diagnostic tests such as ELISA, and second, they can detect and bind the 20-25 amino acid long mature hepcidin. Thus, the antibodies can be used to block hepcidin and inhibit its activity, and, accordingly, may be used as a therapeutic agent. Therefore, the present invention relates in part to an antibody or antibody fragment which interacts with a specific region of a mature form of human hepcidin-25, namely amino acids 74-81 of hepcidin-25, represented as His Arg Ser Lys Cys Gly Met Cys (SEQ ID NO:3), which is also present in pro-hepcidin (see FIG. 8). Also contemplated in the present invention is an antibody raised against a specific region of mature human hepcidin-25 which comprises the region from amino acid 74-81, wherein amino acid residue 78 is Xaa (His Arg Ser Lys Xaa Gly Met Cys [SEQ ID NO:4]), where Xaa is any known amino acid, including L or D stereoisomeric forms of the 20 common amino acids, as well as any modified or unusual amino acid available to the artisan. A specific embodiment, as disclosed and discussed herein, is an antibody raised against an immunogen representing amino acids 74-81 of human hepcidin, whereby amino acid residue 78 is alpha aminobutyric acid (His Arg Ser Lys Abu Gly Met Cys [SEQ ID NO:5]). Thus, an antibody of the present invention, including any form of a monoclonal antibody known in the art, is a monoclonal antibody or fragment thereof which interacts with a specific region of human hepcidin-25 (e.g., including but not limited to amino acids 74-81 of human hepcidin, represented as His Arg Ser Lys Cys Gly Met Cys [SEQ ID NO:3], see FIG. 8). Therefore, the present invention relates to a monoclonal antibody raised against a specific region of human hepcidin-25 which comprises the region from amino acid 74-81, wherein amino acid residue 78 is Xaa (His Arg Ser Lys Xaa Gly Met Cys [SEQ ID NO:4]), as disclosed herein. Again, an exemplified peptide substitutes alpha aminobutyric acid for cysteine (His Arg Ser Lys Abu Gly Met Cys [SEQ ID NO:5]), which was used as an immunogen to generate the exemplified monoclonal antibodies described herein. Also included within the scope of the present invention is any hybridoma capable of producing a monoclonal antibody of the present invention. Particular hybridomas of the present invention are hybridomas which produce monoclonal antibodies mHK(5), mHK(8/1), mHK(8/2), mHK(8/3) and mHK(9), respectively. The antibodies of the present invention may also be in the form of a polyclonal sera raised against this specific region of human hepcidin-25, especially polyclonal sera raised against this core sequence comprising at least amino acid residues 74-81 (His Arg Ser Lys Cys Gly Met Cys [SEQ ID NO:3]), His Arg Ser Lys Xaa Gly Met Cys [SEQ ID NO:4], and/or His Arg Ser Lys Abu Gly Met Cys [SEQ ID NO:5]).

The present invention further relates to a peptide which comprises the amino acid sequence shown as SEQ ID NO:2 or as His Arg Ser Lys Cys Gly Met Cys (SEQ ID NO:3), the amino acid sequence shown as His Arg Ser Lys Xaa Gly Met Cys (SEQ ID NO:4), where Xaa is any known amino acid, including L or D stereoisomeric forms of the 20 common amino acids, as well as any modified or unusual amino acid available to the artisan, and the amino acid sequence shown as His Arg Ser Lys Abu Gly Met Cys (SEQ ID NO:5), where amino acid residue 78 is alpha aminobutyric acid. To this end, the present invention also relates to methods of generating antibodies specific for mature human hepcidin which comprises immunizing a non-human animal with a C-terminal hepcidin peptide which comprises the amino acid sequence as shown in SEQ ID NO:2, SEQ ID NO:3, SEQ ID NO:4, and/or SEQ ID NO:5.

The present invention also relates to a peptide which consists of the amino acid sequence selected from the group consisting of SEQ ID NO:3, SEQ ID NO:4 and SEQ ID NO:5.

The present invention relates in part to methods and assays for quantitatively determining hepcidin levels, which comprise obtaining a tissue or fluid sample from a subject; contacting the sample with an antibody or fragment thereof that specifically binds to a peptide selected from the group consisting of SEQ ID NO:2, SEQ ID NO:3, SEQ ID NO:4, and/or SEQ ID NO:5, and quantifying the hepcidin level in the sample; wherein the non-physiological level of hepcidin is indicative of the disease condition.

The present invention also relates in part to kits for quantitatively determining hepcidin levels, which comprises obtaining a tissue or fluid sample from a subject; contacting the sample with an antibody or fragment thereof that specifically binds to a peptide selected from the group consisting of SEQ ID NO:3, SEQ ID NO:4, and/or SEQ ID NO:5, and quantifying the hepcidin level in the sample; wherein the non-physiological level of hepcidin is indicative of the disease condition.

The present invention also relates to methods, assays and kits for quantitatively determining prohepcidin or mature hepcidin levels, which comprises obtaining a tissue or fluid sample from a subject; contacting the sample with an antibody or fragment thereof that specifically binds to one or more epitopes of human hepcidin precursor amino acid sequence between and including amino acids 74-81 (i.e., SEQ ID NO:3), and quantifying the hepcidin level in the sample; wherein the non-physiological level of hepcidin is indicative of the disease condition.

The present invention also relates to methods, assays and kits for quantitatively determining hepcidin levels, which comprises obtaining a tissue or fluid sample from a subject; contacting the sample with an antibody or fragment thereof that specifically binds to one or more epitopes of human hepcidin precursor amino acid sequence between and including amino acids 60-84 (i.e., SEQ ID NO:2, representing the predominant form of mature human hepcidin), and quantifying the hepcidin level in the sample; wherein the non-physiological level of hepcidin is indicative of the disease condition. Thus, the present invention concerns hepcidin regulation of iron uptake by mammalian cells and the use of hepcidin and/or hepcidin specific antibodies in the diagnosis of diseases involving disturbances of iron metabolism. The diagnostic detection kits of the present invention can be particularly useful in screening the overall population of either humans or animals and identifying those subjects who have these diseases. To this end, one aspect of the invention relates to a method for diagnosing a disease condition characterized by non-physiological levels of hepcidin, comprising obtaining a tissue or fluid sample from a subject; contacting the sample with an antibody or fragment thereof that specifically binds to a polypeptide from the mid-portion (amino acids 20 to 50, SEQ ID NO:1) or C-terminus of hepcidin (amino acids 60 to 84, SEQ ID NO:2, such as a region of the human hepcidin protein comprising amino acids 74-81 (His Arg Ser Lys Cys Gly Met Cys [SEQ ID NO:3])), and quantifying the hepcidin level using an assay based on binding of the antibody and the polypeptide; wherein the non-physiological level of hepcidin is indicative of the disease condition. In one aspect of the present invention, sensitive diagnostic methods and kits were established enabling the detection of pro-hepcidin in human plasma. In another aspect of the present invention, sensitive diagnostic methods and kits were established enabling the detection of mature hepcidin (e.g., HEPCIDIN-25, HEPCIDIN-22, and/or HEPCIDIN-20; see FIG. 8) in human plasma, urine and other body fluids. The invention opens a broad range of therapeutic perspectives, where a hepcidin antibody and diagnostic methods (e.g., HEPCIDIN-25, HEPCIDIN-22, and/or HEPCIDIN-20; see FIG. 8) and kits can be used for the determination of hepcidin as a parameter for the progress of the diseases mentioned above during and after therapy.

The present application further provides important data that hepcidin is expressed in β-cells of the islets of Langerhans in the human pancreas and that it co-localizes with insulin. This application also discloses that the production of hepcidin is regulated by glucose and iron, therapeutic applications of which are discussed further herein.

For purposes of description only, the invention will be described in terms of: (a) generating a hepcidin protein or fragments thereof (including mature 20-25 amino acid long hepcidin protein); (b) generating antibodies that specifically bind a hepcidin protein (including antibodies which bind only pro-hepcidin and antibodies which bind the mature 20-25 amino acid long hepcidin); (c) diagnostic assays and kits for diagnosing subtyping or monitoring the diseases described herein; (d) methods for over expressing and down regulating hepcidin; and (e) therapeutic treatment of the diseases described herein.

Production of a Hepcidin Protein

Isolating a Hepcidin Protein from Blood and Body Fluids

For purposes of the present invention the term hepcidin protein is defined as any mammalian hepcidin polypeptide sharing about 80 percent amino acid sequence identity with the predicted amino acid sequence published by Pigeon and co-workers ((2001) J. Biol. Chem. 276, 7811-7819). The term refers to both pro-hepcidin and the 20-25 amino acid mature human hepcidin, or any fragment thereof (see FIG. 8). The hepcidin proteins provided herein also include proteins characterized by amino acid sequences similar to those of purified hepcidin proteins but into which modification are naturally provided or deliberately engineered. For example, modifications in a hepcidin peptide or DNA sequences can be made by those skilled in the art using known techniques. Modifications of interest in a hepcidin protein sequences may include the alteration, substitution, replacement, insertion or deletion of a selected amino acid residue in the coding sequence. For example, one or more of the cysteine residues may be deleted or replaced with another amino acid to alter the conformation of the molecule (e.g., as shown herein regarding SEQ ID NOS:3, 4 and 5). Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein. Regions of a hepcidin protein that are important for the protein function can be determined by various methods known in the art including the alanine-scanning method which involved systematic substitution of single or strings of amino acids with-alanine, followed by testing the resulting alanine-containing variant for biological activity. This type of analysis determines the importance of the substituted amino acid(s) in biological activity.

Production of a hepcidin protein may be accomplished by isolating a hepcidin protein from the tissue, blood or body fluids of humans or animals suffering from hemochromotosis, iron deficiency anemia, hemosiderosis, liver cirrhosis and other such diseases described herein, using standard techniques known by those of skill in the art. Such techniques included in the invention also relate to methods for producing a hepcidin protein comprising growing a culture of host cells in a suitable culture medium, and purifying a hepcidin protein from the cells or the culture in which the cells are grown.

A variety of methodologies known in the art can be utilized to obtain any one of the isolated hepcidin proteins of the present invention. For example, a hepcidin protein can also be produced by chemical synthesis of the amino acid sequence of a hepcidin protein (Pigeon et al., (2001) J. Biol. Chem. 276, 7811-7819), as predicted from the cloning and sequencing of a cDNA coding for a hepcidin protein. This hepcidin protein sequence information may be utilized to predict the appropriate amino sequence of a fragment of a hepcidin protein to be chemically synthesized using standard peptide synthesis methods known in the art. These methods include a solid-phase method devised by R. Bruce Merrifield, (Erickson and Merrifield, "Solid-Phase Peptide Synthesis", in The Proteins, Volume 2, H. Neurath & R. Hill (Eds.) Academic Press, Inc., New York pp. 255-257; Merrifield, (1986) "Solid phase synthesis", Science, 242:341-347). In the solid-phase method, amino acids are added stepwise to a growing peptide chain that is linked to an insoluble matrix, such as polystyrene beads. A major advantage of this method is that the desired product at each stage is bound to beads that can be rapidly filtered and washed and thus the need to purify intermediates is obviated. All of the reactions are carried out in a single vessel, which eliminates losses due to repeated transfers of products. This solid phase method of chemical peptide synthesis can readily be automated making it feasible to routinely synthesize peptides containing about 50 residues in good yield and purity (Stewart and Young, (1984) Solid Phase Peptide Synthesis, $2^{nd}$ ed., Pierce Chemical Co.; Tam et al., (1983) J. Am. Chem. Soc., 105:6442). For example, a hepcidin protein fragment corresponding to amino acid residues 1 to 50, or 34 to 84 as depicted in FIG. 7 could be synthesized. At the simplest level, commercially available peptide synthesizers are particularly useful in producing small peptides and fragments of a hepcidin protein. Fragments are useful, for example, in generating antibodies against the native hepcidin protein.

One skilled in the art can readily follow known methods for isolating proteins in order to obtain one of the isolated hepcidin proteins/peptides of the present invention. These include, but are not limited to, immunochromatography, HPLC, size-exclusion chromatography, ion-exchange chromatography, and immuno-affinity chromatography. See, e.g., Scopes, Protein Purification: Principles and Practice, Springer-Verlag (1994); Sambrook, et al., in Molecular Cloning: A Laboratory Manual; Ausubel et al., Current Protocols in Molecular Biology.

Finally, one or more reverse-phase high performance liquid chromatography (RP-HPLC) steps employing hydrophobic RP-HPLC media, e.g., silica gel having pendant methyl or other aliphatic groups, can be employed to further purify a hepcidin protein. Some or all of the foregoing purification steps, in various combinations, can also be employed to provide a substantially homogeneous isolated recombinant hepcidin protein. A hepcidin protein thus 'purified' or 'isolated' is substantially free of other mammalian proteins and is defined in accordance with the present invention as an isolated protein.

The sequence of a hepcidin protein may be identified using the Edman degradation method of protein sequencing. This method sequentially removes one amino acid residue at a time from the amino terminal end of a peptide for subsequent sequence identification by chromatographic procedures. See for example, the techniques described in Konigsberg and Steinman, (1977) Strategy and Methods of Sequence Analysis, in Neurath and Hill (eds.), The Proteins ($3^{rd}$ ed.) Vol. 3, pp. 1-178, Academic Press. In addition, sequence analysis of a hepcidin protein may be accelerated by using an automated liquid phase amino acid sequenator following described techniques (Hewick et al., (1981) J. Biol. Chem., 256:7990-7997; Stein and Undefriend, (1984) Analy. Chem., 136:7-23), thereby allowing for the analysis of picomolar quantities of a hepcidin protein.

The purified hepcidin protein can be used in in vitro binding assays that are well known in the art to identify molecules that bind to a hepcidin protein. These molecules include but are not limited to, for e.g., small molecules, molecules from combinatorial libraries, antibodies or other proteins. The molecules identified in the binding assay are then tested for agonist or antagonist activity in in vivo tissue culture or animal models that are well known in the art. In brief, the molecules are titrated into a plurality of cell cultures or animals and then tested for either cell/animal death or prolonged survival of the animal/cells.

In addition, the binding molecules may be complexed with toxins, e.g., ricin or cholera, or with other compounds that are toxic to cells. The toxin-binding molecule complex is then targeted to a tumor or other cell by the specificity of the binding molecule for a hepcidin protein.

Cloning and Expression of Recombinant Hepcidin Protein

In other embodiments, production of a hepcidin protein can be achieved by recombinant DNA technology. For example, appropriate hepcidin nucleotide coding sequences may be synthesized, cloned and expressed in appropriate host cells. Since the DNA sequence coding for a hepcidin protein is known (Pigeon et al., (2001) *J. Biol. Chem.* 276, 7811-7819), DNA probes may be synthesized by standard methods known in the art to screen cDNA libraries prepared from liver tissue from human or animal subjects suffering from hemochromotosis, iron deficiency anemia, hemosiderosis, liver cirrhosis and other diseases described herein, for specific hepcidin protein cDNA's. These DNA probes can further be used to isolate the entire family of hepcidin protein genes from these cDNA libraries using methods that are well known to those skilled in the art. See, for example, the techniques described in Maniatis et al., (1982) Molecular Cloning A Laboratory Manual, Cold Spring Harbor Laboratory, N.Y., Chapter 7.

Hybridization procedures are useful for the screening of recombinant clones by using labeled mixed synthetic oligonucleotide probes where each probe is potentially the complete complement of a specific DNA sequence in the hybridization sample that includes a heterogeneous mixture of denatured double-stranded DNA. For such screening, hybridization is preferably performed on either single-stranded DNA or denatured double-stranded DNA. By using stringent hybridization conditions directed to avoid non-specific binding, it is possible, for example, to allow the autoradiographic visualization of a specific DNA clone by the hybridization of the target DNA to that single probe in the mixture which is its complete complement (Wallace, et al., (1981) *Nucleic Acids Research,* 9:879).

Alternatively, an expression library can be screened indirectly for a hepcidin protein of the invention having at least one epitope using antibodies to the protein. Such antibodies can both be polyclonally or monoclonally derived and used to detect an expression product indicative of the presence of a hepcidin protein. Generally, a lambda gt11 library is constructed and screened immunologically according to the method of Huynh, et al., (1985) (in DNA Cloning: A Practical Approach, D. M. Glover, ed., 1:49).

The development of specific DNA sequences encoding a hepcidin protein can also be obtained by: (1) isolation of a double stranded DNA sequence from the genomic DNA, and (2) chemical manufacture of a DNA sequence to provide the necessary codons for the protein of interest.

The polymerase chain reaction (PCR) technique can be utilized to amplify the individual members of a hepcidin family for subsequent cloning and expression of hepcidin protein cDNAs (e.g., see U.S. Pat. Nos. 4,683,202; 4,683,195; 4,889,818; Gyllensten et al., (1988) Proc. Nat'l Acad. Sci. USA, 85:7652-7656; Ochman et al., (1988) Genetics, 120:621-623; Triglia et al., (1988) Nucl. Acids. Res., 16:8156; Frohman et al., (1988) *Proc. Natl. Acad. Sci. USA,* 85:8998-9002; Loh et al., (1989) *Science,* 243:217-220).

Methods that are well known to those skilled in the art can be used to construct expression vectors containing a hepcidin protein or fragments thereof coding sequences and appropriate transcriptional/translational control signals. These methods include in vitro recombinant DNA techniques, synthetic techniques and in vivo recombination/genetic recombination. See, for example, the techniques described in Maniatis et al., 1982, Molecular Cloning A Laboratory Manual, Cold Spring Harbor Laboratory, N.Y., Chapter 12.

A variety of host-expression vector systems may be utilized to express a hepcidin protein or fragment thereof. These include but are not limited to microorganisms such as bacteria transformed with recombinant bacteriophage DNA, plasmid DNA or cosmid DNA expression vectors containing a coding sequence for a hepcidin protein or fragments thereof; yeast transformed with recombinant yeast expression vectors containing a coding sequence for a hepcidin protein or fragment thereof; insect cell systems infected with recombinant virus expression vectors (e.g., baculovirus) containing a coding sequence for a hepcidin protein or fragment thereof; or animal cell systems infected with recombinant virus expression vectors (e.g., adenovirus, vaccinia virus) containing a coding sequence for a hepcidin protein or fragment thereof.

The expression elements of these vectors vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage lambda, plac, ptrp, ptac (ptrp-lac hybrid promoter) and the like may be used; when cloning in insect cell systems, promoters such as the baculovirus polyhedrin promoter may be used; when cloning in mammalian cell systems, promoters such as the adenovirus late promoter or the vaccinia virus 7.5K promoter may be used. Promoters produced by recombinant DNA or synthetic techniques may also be used to provide for transcription of the inserted coding sequence for a hepcidin protein or fragment thereof.

In yeast, a number of vectors containing constitutive or inducible promoters may be used. For reviews see, Current Protocols in Molecular Biology, Vol. 2, (1988) Ed. Ausubel et al., Greene Publish. Assoc. & Wiley Interscience Ch. 13; Grant et al., (1987) Expression and Secretion Vectors for Yeast, in Methods in Enzymology, Eds. Wu & Grossman, (1987) Acad. Press, N.Y., Vol. 153, pp. 516-544; Glover, (1986) DNA Cloning, Vol. II, IRL Press, Wash., D.C. Ch. 3; and Bitter, (1987) Heterologous Gene Expression in Yeast, Methods in Enzymology, Eds. Berger & Kimmel, Acad. Press, N.Y., Vol. 152, pp. 673-684; and The Molecular Biology of the Yeast Saccharomyces, (1982) Eds. Strathern et al., Cold Spring Harbor Press, Vols. I and II. For complementation assays in yeast, cDNAs for hepcidin proteins or fragments thereof may be cloned into yeast episomal plasmids (YEp) that replicate autonomously in yeast due to the presence of the yeast 2 mu circle. A hepcidin protein or fragment thereof sequence may be cloned behind either a constitutive yeast promoter such as ADH or LEU2 or an inducible promoter such as GAL (Cloning in Yeast, Ch. 3, R. Rothstein (1986) In DNA Cloning Vol. 11, A Practical Approach, Ed. D M Glover, IRL Press, Wash., D.C.). Constructs may contain the 5' and 3' non-translated regions of a cognate hepcidin protein mRNA or those corresponding to a yeast gene. YEp plasmids transform at high efficiency and the plasmids are extremely stable. Alternatively vectors may be used which promote integration of foreign DNA sequences into the yeast chromosome.

A particularly good expression system that could be used to express a hepcidin protein or fragments thereof is an insect system. In one such system, *Autographa californica* nuclear polyhedrosis virus (AcNPV) is used as a vector to express foreign genes. The virus grows in *Spodoptera frugiperda* cells. A hepcidin protein or fragment thereof coding sequence may be cloned into non-essential regions (for example the polyhedrin gene) of the virus and placed under control of an AcNPV promoter (for example the polyhedrin promoter). Successful insertion of the polyhedrin gene results in production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., (1983) J. Biol., 46:586; Smith, U.S. Pat. No. 4,215,051). In addition, materials and methods for baculovirus/insect cell expression systems are commercially available in kit form from, e.g., Invitrogen, San Diego, Calif., U.S.A. (the MaxBat™ kit), and such methods are well known in the art, as described in Summers and Smith, Texas Agricultural Experiment Station Bulletin No. 1555 (1987), incorporated herein by reference. As used herein, an insect cell capable of expressing a hepcidin polynucleotide of the present invention is transformed.

In cases where an adenovirus is used as an expression vector, a hepcidin protein or fragment thereof coding sequence may be ligated to an adenovirus transcription/translation control complex, e.g., the late promoter and tripartite leader sequence. This chimeric gene may then be inserted in the adenovirus genome by in vivo or in vitro recombination. Insertion in a non-essential region of the viral genome (e.g., region E1 or E3) will result in a recombinant virus that is viable and capable of expressing a hepcidin protein of fragment thereof in infected hosts. (e.g., See Logan & Shenk, (1984) Proc. Natl. Acad. Sci., (USA) 81:3655-3659). Alternatively, the vaccinia 7.5K promoter may be used. (e.g., see Mackett et al., (1982) Proc. Natl. Acad. Sci., (USA) 79:7415-7419; Mackett et al., (1984) J. Virol., 49:857-864; Panicali et al., (1982) Proc. Natl. Acad. Sci., 79: 4927-4931).

Specific initiation signals may also be required for efficient translation of the inserted hepcidin protein or fragment thereof coding sequences. These signals include the ATG initiation codon and adjacent sequences. In cases where the entire hepcidin protein genome, including its own initiation codon and adjacent sequences, are inserted into the appropriate expression vectors, no additional translational control signals may be needed. However, in cases where only a portion of a hepcidin protein coding sequence is inserted, exogenous translational control signals, including the ATG initiation codon, must be provided. Furthermore, the initiation codon must be in phase with the reading frame of a hepcidin protein or fragment thereof coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., (1987) Methods in Enzymol., 153:516-544).

In addition, a host cell strain may be chosen which modulates the expression of the inserted sequences, or modifies and processes the gene product in the specific fashion desired. Expression driven by certain promoters can be elevated in the presence of certain inducers, (e.g., zinc and cadmium ions for metallothionein promoters). Therefore, expression of the genetically engineered hepcidin protein or fragment thereof may be controlled. This is important if the protein product of the cloned foreign gene is lethal to host cells. Furthermore, modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

The host cells which contain a hepcidin protein or fragment thereof coding sequence and which express the biologically active hepcidin protein or fragment thereof gene product may be identified by at least four general approaches: (a) DNA-DNA hybridization; (b) the presence or absence of "marker" gene functions; (c) assessing the level of transcription as measured by expression of hepcidin protein mRNA transcripts in host cells; and (d) detection of hepcidin protein gene products as measured by immunoassays or by its biological activity.

In the first approach, the presence of a hepcidin protein or fragment thereof coding sequence inserted in the expression vector can be detected by DNA-DNA hybridization using probes comprising nucleotide sequences that are homologous to a hepcidin protein coding sequence or particular portions thereof substantially as described recently (Pigeon et al., (2001) J. Biol. Chem. 276, 7811-7819).

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if a hepcidin protein or fragment thereof coding sequence is inserted within a marker gene sequence of the vector, recombinants containing a hepcidin protein or fragment thereof coding sequence can be identified by the absence of the marker gene function. Alternatively, a marker gene can be placed in tandem with a hepcidin protein or fragment thereof coding sequence under the control of the same or different promoter used to control the expression of a hepcidin coding sequence. Expression of the marker in response to induction or selection indicates expression of a hepcidin protein coding sequence.

In the third approach, transcriptional activity for a hepcidin protein or fragment thereof coding region can be assessed by hybridization assays. For example, RNA can be isolated and analyzed by Northern blot using a probe homologous to a hepcidin protein or fragment thereof coding sequence or particular portions thereof substantially as described (Pigeon et al., (2001) J. Biol. Chem. 276, 7811-7819). Alternatively, total nucleic acids of the host cell may be extracted and assayed for hybridization to such probes.

In the fourth approach, the expression of a hepcidin protein or fragment thereof product can be assessed immunologically, for example by Western blots, immunoassays such as radioimmunoprecipitation, enzyme-linked immunoassays and the like.

Once a recombinant that expresses a hepcidin protein or fragment thereof is identified, the gene product should be analyzed. This can be achieved by assays based on the physical, immunological or functional properties of the product. For example, the methods of the invention include a process for producing a hepcidin protein in which a host cell containing a suitable expression vector that includes a hepcidin polynucleotide of the invention is cultured under conditions that allow expression of the encoded hepcidin protein. A hepcidin protein can be recovered from the culture, conveniently from the culture medium, or from a lysate prepared from the host cells and further purified. Preferred embodiments include those in which the protein produced by such process is a full length or mature form of the protein.

The present invention further provides isolated hepcidin protein encoded by the nucleic acid fragments of the present invention or by degenerate variants of the nucleic acid fragments of the present invention. By "degenerate variant" is intended nucleotide fragments that differ from a nucleic acid fragment of the present invention (e.g., an ORF) by nucleotide sequence but, due to the degeneracy of the genetic code, encode an identical protein sequence. Preferred nucleic acid fragments of the present invention are the Orbs that encode proteins.

A hepcidin protein of the present invention can alternatively be purified from cells that have been altered to express a hepcidin protein. As used herein, a cell is altered to express a desired polypeptide or protein when the cell, through genetic manipulation, is made to produce a hepcidin protein which it normally does not produce or which the cell normally produces at a lower level. One skilled in the art can readily adapt procedures for introducing and expressing either recombinant or synthetic sequences into eukaryotic or prokaryotic cells in order to generate a cell which produces a hepcidin protein of the present invention.

A hepcidin protein of the invention may also be expressed as a product of transgenic animals, e.g., as a component of the milk of transgenic cows, goats, pigs, or sheep which are characterized by somatic or germ cells containing a nucleotide sequence encoding a hepcidin protein.

A hepcidin protein (e.g., see SEQ ID NOS. 1-7) may also be produced by known conventional chemical synthesis-Methods for constructing a hepcidin protein of the present invention by synthetic means are known to those skilled in the art. The synthetically-constructed hepcidin protein sequences, by virtue of sharing primary, secondary or tertiary structural and/or conformational characteristics with natural hepcidin protein may possess biological properties in common therewith, including protein activity. Thus, they may be employed as biologically active or immunological substitutes for a natural, purified hepcidin protein in screening of therapeutic compounds and in immunological processes for the development of antibodies.

A hepcidin protein of the invention may be prepared by culturing transformed host cells under culture conditions suitable to express the recombinant protein. The resulting expressed hepcidin protein may then be purified from such culture (i.e., from culture medium or cell extracts) using known purification processes, such as gel filtration and ion exchange chromatography. The purification of a hepcidin protein may also include an affinity column containing agents which will bind to the protein; one or more column steps over such affinity resins as concanavalin A-agarose, Heparin-Toyopearl™ or Cibacrom blue 3GA Sepharose™; one or more steps involving hydrophobic interaction chromatography using such resins as phenyl ether, butyl ether, or propyl ether; or immunoaffinity chromatography.

Alternatively, a hepcidin protein of the invention may also be expressed in a form that will facilitate purification. For example, it may be expressed as a fusion protein, such as those of maltose binding protein (MBP), glutathione-S-transferase (GST) or thioredoxin (TRX), or as a His tag. Kits for expression and purification of such fusion proteins are commercially available from New England BioLab (Beverly, Mass.), Pharmacia (Piscataway, N.J.) and Invitrogen, respectively. A hepcidin protein can also be tagged with an epitope and subsequently purified by using a specific antibody directed to such epitope. One such epitope ("FLAG®") is commercially available from Kodak (New Haven, Conn.).

Other fragments and derivatives of the sequences of hepcidin proteins/peptides which would be expected to retain protein activity in whole or in part (e.g., binding to a TfR2 receptor, binding to a hepcidin specific antibody, etc.) and are useful for screening or other immunological methodologies may also be easily made by those skilled in the art given the disclosures herein. Such modifications are encompassed by the present invention.

A hepcidin protein or fragment thereof should be immunoreactive whether it results from the expression of the entire gene sequence, a portion of the gene sequence or from two or more gene sequences which are ligated to direct the production of chimeric proteins. This reactivity may be demonstrated by standard immunological techniques, such as radio-immunoprecipitation, radioimmune competition, or immunoblots.

Generation of Monoclonal Antibodies that Identify a Pro-Hepcidin or Mature Hepcidin Protein From the published human pro-hepcidin sequence (Krause, A. et al., *FEBS Lett.* 480:147-150 (2000); Pigeon, C. et al., *J. Biol. Chem.* 276:7811-7819 (2001)) the modified peptide hepcidin-(74-81) was synthesized as C terminal amides using a standard Fmoc protocol. To avoid the problem with cysteine-disulfide-bridges the amino acid Cysteine at position hepcidin-78 was replaced by the isosteric amino acid alpha aminobutyric acid (Abu). The immunization peptide was: H R S K Abu G M C (SEQ ID NO:5).

The immunization peptide was coupled to keyhole limpet hemocyanin using m-maleimidobenzoyl-N-hydroxysuccinimide ester, and mice were immunized with the peptide conjugate. After producing monoclonal antibodies using standard protocol the titer of the antibodies were tested by ELISA. The antibodies mHK(5), mHK(8/1), mHK(8/2), mHK(8/3), and mHK(9), each directed against hepcidin-(74-Abu-81), were used in studies, as discussed herein. These antibodies were able to identify hepcidin in Western blot, immunohistochemistry and ELISA experiments.

Various procedures known in the art may also be used for the production of antibodies to the mid-portion (amino acids 20 to 50) or C-terminus of epitopes (amino acids 60 to 84) of a hepcidin protein. The hepcidin specific antibodies bind those epitopes and no other known sequences.

In one non-limiting example, the epitope is identical to SEQ ID NO:4. (HRSKXGMC). In a native amino acid hepcidin sequence, "X" OF SEQ ID NO:4 is cysteine (i.e., SEQ ID NO:3). However, the use of the native sequence of hepcidin fragment (HRSKCGMC; SEQ ID NO:3) has a disadvantage due to disulfide bridges being formed between the two cysteine residues of this epitope. Thus, the inventors designed a creative way to overcome this drawback and yet create antibodies which specifically bind to the native sequence HRSKCGMC (SEQ ID NO:3) of hepcidin. In different embodiments, the cysteine at position 5 of this sequence (HRSKXGMC (SEQ ID NO:4) is replaced with another molecule, which preferably resembles cysteine but cannot form disulfide bridges with the cysteine at the C-terminus of SEQ. ID. NO. 3. In one embodiment, the residue designated as "X" is an alpha aminobutyric acid (see SEQ ID NO:5). Other molecules can also be used to replace the cysteine in position X of SEQ ID NO:3. Suitable non-limiting examples of such molecules are in general, alpha-amino acids with straight or branched backbones up to 9 carbon atoms long. These alpha amino acids may have hydroxy groups attached to carbon atoms β to ω. A person of the ordinary skill in the art will be able to select appropriate residues taking into consideration the following factors: structural similarity with cysteine and inability (or limited ability) to form bonds other than peptide bonds with immediately adjacent amino acids (in this case, lysine and glycine).

Such antibodies, as discussed further herein, include but are not limited to polyclonal, monoclonal, chimeric, humanized, human, single chain, Fab fragments and an Fab expression library. For the production of antibodies, various host animals may be immunized by injection with a particular hepcidin protein, or a synthetic hepcidin protein or an immunogenic peptide comprising a portion of hepcidin (e.g., see SEQ ID NOS:3, 4 and/or 5), including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *corynebacterium parvum*.

Thus, antibodies may take the form of any type of relevant antibody fragment, antibody binding portion, specific binding member, a non-protein synthetic mimic, or any other relevant terminology known in the art which refers to an entity which at least substantially retains the binding specificity/neutralization activity. Therefore, the term "antibody" as used in any context within this specification is meant to include, but not be limited to, any specific binding member, immunoglobulin class and/or isotype (e.g., IgG1, IgG2, IgG3, IgG4, IgM, IgA, IgD, IgE and IgM); and biologically relevant fragment or specific binding member thereof, including but not limited to Fab, F(ab')2, Fv, and scFv (single chain or related entity), which are capable of binding to the respective hepcidin protein or fragment, including but not limited to pro-hepcidin and any mature form of hepcidin. Therefore, it is well known in the art, and is included as review only, that an "antibody" refers to a glycoprotein comprising at least two heavy (H) chains and two light (L) chains inter-connected by disulfide bonds, or an antigen binding portion thereof. A heavy chain is comprised of a heavy chain variable region (VH) and a heavy chain constant region (CHI, CH2 and CH3). A light chain is comprised of a light chain variable region (Vat) and a light chain constant region (CL). The variable regions of both the heavy and light chains comprise a framework (FW) and complementarily determining regions (CDR). The four (4) FW regions are relatively conversed while CDR regions (CDR1, CDR2 and CDR3) represent hypervariable regions and are arranged from $NH_2$ terminus to the COOH terminus as follows: FW1, CDR1, FW2, CDR2, FW3, CDR3, FW4. The variable regions of the heavy and light chains contain a binding domain that interacts with an antigen while, depending of the isotype, the constant region(s) may mediate the binding of the immunoglobulin to host tissues or factors. That said, also included in the working definition of "antibody" are chimeric antibodies, humanized antibodies, a recombinant antibody, human antibodies generated from a transgenic non-human animal, as well as antibodies selected from libraries using enrichment technologies available to the artisan. Antibody fragments are obtained using techniques readily known and available to those of ordinary skill in the art, as reviewed below. Therefore, an "antibody" is any such entity or specific binding member, which specifically binds to the respective portion of hepcidin so as to be useful in various diagnostic methods, as well as being a candidate for therapeutic applications intended to treat non-physiological concentrations of hepcidin protein within the patient, such as abnormally high concentrations of hepcidin associated with numerous disease states disclosed herein. Therefore, the term "antibody" further describes an immunoglobulin, whether natural or partly or wholly synthetically produced; any polypeptide or protein having a binding domain which is, or is substantially homologous to, an antibody binding domain. These can be derived from natural sources, or they may be partly or wholly synthetically produced. Examples of antibodies are the immunoglobulin isotypes and their isotypic subclasses; fragments which comprise an antigen binding domain such as Fab, scFv, Fv, dAb, Fd and diabodies, as discussed without limitation, infra. It is known in the art that it is possible to manipulate monoclonal and other antibodies and use techniques of recombinant DNA technology to produce other antibodies or chimeric molecules which retain the specificity of the original antibody. Such techniques may evolve introducing DNA encoding the immunoglobulin variable region, or the complementarily determining regions (CDRs), of an antibody to the constant regions, or constant regions plus framework regions, of a different immunoglobulin. A hybridoma or other cell producing an antibody may be subject to genetic mutation or other changes, which may or may not alter the binding specificity of antibodies produced. Antibodies can be modified in a number of ways, and the term "antibody" should be construed as covering any specific binding member or substance having a binding domain with the required specificity, as shown herein with the exemplified mouse monoclonal antibodies. Thus, this term covers antibody fragments, derivatives, functional equivalents and homologues of antibodies, including any polypeptide comprising an immunoglobulin binding domain, whether natural or wholly or partially synthetic. Such an entity may be a binding fragment encompassed within the term "antigen-binding portion" or "specific binding member" of an antibody including but not limited to (i) a Fab fragment, a monovalent fragment consisting of the VL, VH, CL and CH domains; (ii) a F(ab')2 fragment, a bivalent fragment comprising two Fab fragments linked by a disulfide bridge at the hinge region; (iii) a Fd fragment consisting of the VH and CH domains; (iv) a Fv fragment consisting of the VL and VH domains of a single arm of an antibody, (v) a dAb fragment, which comprises a VH domain; (vi) an isolated complementarily determining region (CDR); (vii) a 'scAb', an antibody fragment containing VH and VL as well as either CL or CHI; and (viii) artificial antibodies based upon protein scaffolds, including but not limited to fibronectin type III polypeptide antibodies (e.g., see U.S. Pat. No. 6,703,199, issued to Koide on Mar. 9, 2004 and PCT International Application Publication No. WO 02/32925). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)).

Polyclonal antibodies may be readily generated by one of ordinary skill in the art from a variety of warm-blooded animals such as horses, cows, various fowl, rabbits, mice, or rats. Briefly, hepcidin is utilized to immunize the animal through intraperitoneal, intramuscular, intraocular, or subcutaneous injections, an adjuvant such as Freund's complete or incomplete adjuvant. Following several booster immunizations, samples of serum are collected and tested for reactivity to hepcidin. Particularly preferred polyclonal antisera will give a signal on one of these assays that is at least three times greater than background. Once the titer of the animal has reached a plateau in terms of its reactivity to hepcidin, larger quantities of antisera may be readily obtained either by weekly bleedings, or by exsanguinating the animal.

Monoclonal antibodies to peptides of hepcidin may be prepared by using any technique that provides for the production of antibody molecules by continuous cell lines in culture. These include but are not limited to the hybridoma technique originally described by Kohler and Milstein, (*Nature*, (1975) 256:495-497), the more recent human B-cell hybridoma technique (Kosbor et al., (1983) *Immunology Today,* 4:72) and the EBV-hybridoma technique (Cole et al., (1985) Monoclonal Antibodies and Cancer Therapy, Alan R. Liss, Inc., pp. 77-96). In an additional embodiment of the invention monoclonal antibodies specific to hepcidin proteins/peptides may be produced in germ-free animals utilizing recent technology (PCT/US90/02545). According to the invention, human antibodies may be used and can be obtained by using human hybridomas (Cote at al., (1983) *Proc. Natl. Acad. Sci.,* 80:2026-2030) or by transforming human B cells with EBV virus in vitro (Cole et al., (1985) in, Monoclonal Antibodies and Cancer Therapy, Alan R. Liss, pp. 77-96). In fact, according to the invention, techniques developed for the production of "chimeric antibodies" (Morrison et al., (1984) *Proc. Natl. Acad. Sci.,* 81:6851-6855; Neuberger et al., (1984) *Nature,* 312:604-608; Takeda et al., (1985) *Nature,* 314:452-454) by splicing the genes from a mouse antibody molecule of appropriate antigen specificity together with genes from a human antibody molecule of appropriate biological activity can be used; such antibodies are due to this invention.

Thus, polyclonal or monoclonal antibodies for use in the disclosed treatment methods may be raised by known techniques. Monospecific (i.e., monoclonal) murine (mouse) antibodies showing specificity to a confirmational epitope may be purified from mammalian antisera containing antibodies reactive against this region, or may be prepared as monoclonal antibodies using any techniques available to the artisan. "Monospecific" or "monoclonal" antibody as used herein is defined as a single antibody species or multiple antibody species with homogenous binding characteristics. As noted above, hybridoma cells are produced by mixing the splenic lymphocytes with an appropriate fusion partner, preferably myeloma cells, under conditions which will allow the formation of stable hybridomas. The splenic antibody producing cells and myeloma cells are fused, selected, and screened for antibody production. Hybridoma cells from antibody positive wells are cloned by a technique such as the soft agar technique of MacPherson, 1973, Soft Agar Techniques, in Tissue Culture Methods and Applications, Kruse and Paterson, Eds, Academic Press. Monoclonal antibodies are produced in vivo by injecting respective hydridoma cells into pristine primed mice, collecting ascite fluid after an interval of time, and prepared by techniques well known in the art.

Beyond species specific monoclonal antibodies described above, the antibodies of the present invention may also be in the form of a "chimeric antibody", a monoclonal antibody constructed from the variable regions derived from say, the murine source, and constant regions derived from the intended host source (e.g., human; for a review, see Morrison and Oi, 1989, *Advances in Immunology*, 44: 65-92). The variable light and heavy genes from the rodent (e.g., mouse) antibody are cloned into a mammalian expression vector which contains an appropriate human light chain and heavy chain coding region, respectively. These heavy and light "chimeric" expression vectors are cotransfected into a recipient cell line and selected and expanded by known techniques. This cell line may then be subjected to known cell culture techniques, resulting in production of both the light and heavy chains of a chimeric antibody. Such chimeric antibodies have historically been shown to have the antigen-binding capacity of the original rodent monoclonal while significantly reducing immunogenicity problems upon host administration.

A logical improvement to the chimeric antibody is the "humanized antibody," which arguably reduces the chance of the patient mounting an immune response against a therapeutic antibody when compared to use of a chimeric or full murine monoclonal antibody. The strategy of "humanizing" a murine Mab is based on replacing amino acid residues which differ from those in the human sequences by site directed mutagenesis of individual residues or by grafting of entire complementarily determining regions (Jones et al., 1986, *Nature* 321: 522-526). This technology is again now well known in the art and is represented by numerous strategies to improve on this technology; namely by implementing strategies including, but not limited to, "reshaping" (see Verhoeyen, et al., 1988, *Science* 239: 1534-1536), "hyperchimerization" (see Queen, et al., 1991, *Proc. Natl. Acad. Sci.* 88:2869-2873) or "veneering" (Mark, et al., 1994, Derivation of Therapeutically Active Humanized and Veneered anti-CD18 Antibodies. Metcalf end Dalton, eds. Cellular Adhesion: Molecular Definition to Therapeutic Potential. New York: Plenum Press, 291-312). These strategies all involve to some degree sequence comparison between rodent and human sequences to determine whether specific amino acid substitutions from a rodent to human consensus is appropriate. Whatever the variations, the central theme involved in generating a humanized antibody relies on CDR grafting, where these three antigen binding sites from both the light and heavy chain are effectively removed from the rodent expressing antibody clone and subcloned (or "grafted") into an expression vector coding for the framework region of the human antibody. Therefore, a "humanized antibody" is effectively an antibody constructed with only murine CDRs (minus any additional improvements generated by incorporating one or more of the above mentioned strategies), with the remainder of the variable region and all of the constant region being derived from a human source. Such humanized antibodies may be advantageous for therapeutic purposes. Thus, "humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. The humanization techniques are well known in the art. Further, some humanization protocols are commercially available, for example, from Diversa Corp (San Diego, Calif.). In some instances, FV framework region (FR) residues of the human immunoglobulin are replaced by corresponding non-human residues. Furthermore, humanized antibodies may comprise residues which are not found in the recipient antibody or in the donor antibody. these modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (FC), typically that of a human immunoglobulin. For further details, see Jones et al., *Nature* 321:522-525 (1986); Reichmann et al., Nature 332:323-329 (1988); and Presta, Curr. Op. Struct. Biol. 2:593-596 (1992). Thus, essentially, humanizing involves assembly of hypervariable regions of a non-human antibody and conserved regions of human antibodies.

According to the invention, techniques described for the production of single chain antibodies (U.S. Pat. No. 4,946,778) can be adapted to produce hepcidin protein-specific single chain antibodies.

An additional embodiment of the invention utilizes the techniques described for the construction of Fab expression libraries (Huse et al., (1989) Science, 246:1275-1281) to allow rapid and easy identification of monoclonal Fab fragments with the desired specificity to hepcidin proteins/peptides.

Antibody fragments that contain specific binding sites for a hepcidin protein may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments.

An analysis of the three-dimensional structures of antibody-combining sites suggests that only 20% to 33% of CDR residues are critical in the antigen-antibody interaction. These residues, which are located in the regions of high variability and which are most likely to be unique to each antibody, are designated as specificity-determining residues (SDRS) (Padlan E et al. *FASEB J* 9: 133-9, 1995). SDR-grafted humanized antibody has a substantially reduced number of non-human residues as compared with those present in its CDR-grafted counterpart (Tamura M et al., *J Immunol* 164: 1432-41, 2000).

For a humanization protocol to achieve the desirable goal, it is important that the structural features of the target antibody are preserved. humanization often results in a significant modification of the antigen-combining site structure and a consequent loss in the antigen-binding affinity of the antibody. to avoid this problem, in vitro affinity maturation (De Pascalis R et al. *Clin Cancer Res* 9: 5521-31, 2003) can be used to generate humanized antibodies with enhanced antigen-binding affinity and reduced immunogenic potential in human patients.

Yet another improvement over re-engineered antibodies as reviewed above is the generation of fully human monoclonal antibodies. The first involves the use of genetically engineered mouse strains which possess an immune system whereby the mouse antibody genes have been inactivated and in turn replaced with a repertoire of functional human antibody genes, while leaving other components of the mouse immune system unchanged. Such genetically engineered mice allow for the natural in vivo immune response and affinity maturation process which results in high affinity, fully human monoclonal antibodies. This technology is again now well known in the art and is fully detailed in various publications, including but not limited to U.S. Pat. Nos. 5,939,598; 6,075,181; 6,114,598; 6,150,584 and related family members (assigned to Abgenix, disclosing their XenoMouse technology); as well as U.S. Pat. Nos. 5,545,806; 5,569,825; 5,625,126; 5,633,425; 5,789,650; 5,877,397; 5,661,016; 5,814,318; 5,874,299; and 5,770,429 (assigned to GenPharm International and available through Medarex, under the umbrella of the "UltraMab Human Antibody Development System"). See also a review from Kellerman and Green (2002, *Curr. Opinion in Biotechnology* 13: 593-597)

Finally, techniques are available to the artisan for the selection of antibody fragments from libraries using enrichment technologies, including but not limited to phage display, ribosome display (Hanes and Pluckthun, 1997, *Proc. Nat. Acad. Sci.* 94: 4937-4942), bacterial display (Georgiou, et al., 1997, *Nature Biotechnology* 15: 29-34) and/or yeast display (Kieke, et al., 1997, *Protein Engineering* 10: 1303-1310) may be utilized as alternatives to previously discussed technologies to select single chain antibodies which specifically bind to hepcidin. Single-chain antibodies are selected from a library of single chain antibodies produced directly utilizing filamentous phage technology. Phage display technology is known in the art (e.g., see technology from Cambridge Antibody Technology (CAT)) as disclosed in U.S. Pat. Nos. 5,565,332; 5, 733,743; 5,871,907; 5,872,215; 5,885,793; 5,962,255; 6,140,471; 6,225,447; 6,291650; 6,492,160; 6,521,404; 6,544,731; 6,555,313; 6,582,915; 6,593,081, as well as other U.S. family members, or applications which rely on priority filing GB 9206318, filed 24 May 1992; see also Vaughn, et al. 1996, *Nature Biotechnology* 14: 309-314). Single chain antibodies may also be designed and constructed using available recombinant DNA technology, such as a DNA amplification method (e.g., PCR), or possibly by using a respective hybridoma cDNA as a template. Single-chain antibodies can be mono- or bispecific; bivalent or tetravalent. A nucleotide sequence encoding a single-chain antibody can be constructed using manual or automated nucleotide synthesis, cloned into an expression construct using standard recombinant DNA methods, and introduced into a cell to express the coding sequence, as described below.

The term "recombinant human antibody", represents a viable subset of "antibodies" generated by various means of recombinant DNA technology and non-human transgenics that are well known in the art. Such methodology is utilized to generate an antibody from one or the following origins: (i) a scFv or alternative antibody isolated from a combinatorial human antibody library; (ii) a partial or complete antibody generated from a respective expression vector stably or transiently transfected into a host cell, preferably a mammalian host cell; and/or (iii) an antibody isolated from a non-human transgenic animal which contains human immunoglobulin genes, or by any other known methodology which relies of the recombinant 'mixing and matching' of human immunoglobulin gene sequences to other DNA sequences in order to generate the human recombinant antibody of interest.

In another aspect, the invention provides a method of monitoring a disease condition characterized by non-physiological levels of hepcidin in a subject, comprising: determining an amount of the hepcidin protein (including both 84 amino acid long hepcidin and the 20-25 amino acid long mature hepcidin) at a first time; determining an amount of the hepcidin protein at a second, later time; whereby $|H_1-N|\uparrow<|H_2-N|$ indicates that the disease condition has progressed, and $|H_1-N|>|H_2-N|$ indicates that the disease condition has improved, wherein $H_1$ equals to the amount of the hepcidin protein measured at the first time; $H_2$ equals to the amount of the hepcidin protein measured at the second time; and N equals to the normal range or amount of the hepcidin protein. This method may be applied to follow a course of any of the disease conditions described herein, with representative non-limiting examples being anemia of chronic disease and renal insufficiency. In another embodiment, the method of the instant aspect may be used to evaluate a treatment of any of the diseases. For example, in one embodiment, the measurement of hepcidin conducted at the first time is prior to the treatment, and the measurement of hepcidin conducted at the second time is during or after the treatment. Suitable examples of treatments include, without limitation erythropoietin therapy and/or iron substitution (e.g., oral or i.v. iron substitution). A normal ranges or amounts of hepcidin (i.e., the meaning of "|N|" in the instant disclosure) are available from public sources, such as, for example, Pubmed. For example, in the instant application, the inventors found that in their study, the level of the 84 amino acid hepcidin was 92±17 ng/ml (mean±SE; 10 healthy persons). These results are consistent with the previous reports that the physiological concentration of 84-amino acid long hepcidin is in the range of 51.6-153.4 ng/mL (mean 106.2 ng/mL). Thus, the normal range or level may be compared with the level of hepcidin during or after the treatment and if a significant difference is found, then the practitioner may infer the efficacy of the treatment.

Diagnostic Assays and Kits

Yet another purpose of the present invention is to provide reagents for use in diagnostic assays for the detection of a hepcidin protein (including both pro-hepcidin and the 20-25 amino acid long mature hepcidin) and hepcidin fragments from individuals suffering from hemochromotosis, iron deficiency anemia, hemosiderosis, liver cirrhosis and such other diseases described herein.

In one mode of this embodiment, a hepcidin protein of the present invention may be used as an antigen in immunoassays for the detection of those individuals suffering from hemochromotosis, iron deficiency anemia, hemosiderosis, liver cirrhosis and such other diseases described herein. A hepcidin protein, polypeptide and/or peptide of the present invention may be used in any immunoassay system known in the art including, but not limited to: radioimmunoassays, enzyme-linked immunosorbent assay, "sandwich" assays, precipitin reactions, gel diffusion immunodiffusion assays, agglutination assays, fluorescent immunoassays, protein A immunoassays and immunoelectrophoresis assays, to name but a few U.S. Pat. No. 4,629,783 and patents cited therein also describe suitable assays.

According to the present invention, monoclonal or polyclonal antibodies produced to various forms of a hepcidin protein (including both pro-hepcidin and the 20-25 amino acid long mature hepcidin), and hepcidin fragments can be used in an immunoassay on samples of blood, spinal fluid or other body fluid to diagnose subjects with hemochromotosis, iron deficiency anemia, hemosiderosis, liver cirrhosis and other diseases described herein.

In one embodiment of the invention, a sample of blood is removed from the patient by venesection and placed in contact with an anticoagulant such as EDTA, mixed, centrifuged at 600 g for 10 min and the plasma removed as is common in the art or a sample of spinal fluid is removed from the patient by lumbar puncture.

The antibodies described herein may be used as the basic reagents in a number of different immunoassays to determine the presence of a hepcidin protein in a sample of tissue, blood or body fluid. Generally speaking, the antibodies can be employed in any type of immunoassay, whether qualitative or quantitative. This includes both the two-site sandwich assay and the single site immunoassay of the non-competitive type, as well as in traditional competitive binding assays.

Particularly preferred, for ease of detection, and its quantitative nature, is the sandwich or double antibody assay, of which a number of variations exist, all of which are intended to be encompassed by the present invention.

For example, in a typical forward sandwich assay, unlabeled antibody is immobilized on a solid substrate, e.g., microtiter plate wells, and the sample to be tested is brought into contact with the bound molecule. After a suitable period of incubation, for a period of time sufficient to allow formation of an antibody-antigen binary complex, a second antibody, labeled with a reporter molecule capable of inducing a detectable signal, is then added and incubation is continued allowing sufficient time for binding with the antigen at a different site and the formation of a ternary complex of antibody-antigen-labeled antibody. Any unreacted material is washed away, and the presence of the antigen is determined by observation of a signal, which may be quantitated by comparison with a control sample containing known amounts of antigen. Variations on the forward sandwich assay include the simultaneous assay, in which both sample and antibody are added simultaneously to the bound antibody, or a reverse sandwich assay in which the labeled antibody and sample to be tested are first combined, incubated and added to the unlabelled surface bound antibody. These techniques are well known to those skilled in the art, and the possibility of minor variations will be readily apparent. As used herein, "sandwich assay" is intended to encompass all variations on the basic two-site technique.

For the sandwich assays of the present invention, the only limiting factor is that both antibodies have different binding specificities for a hepcidin protein. Thus, a number of possible combinations are possible.

As a more specific example, in a typical forward sandwich assay, a primary antibody is either covalently or passively bound to a solid support. The solid surface is usually glass or a polymer, the most commonly used polymers being cellulose, polyacrylamide, nylon, polystyrene, polyvinylchloride or polypropylene. The solid supports may be in the form of tubes, beads, discs or microplates, or any other surfaces suitable for conducting an immunoassay. The binding processes are well known in the art. Following binding, the solid phase-antibody complex is washed in preparation for the test sample. An aliquot of the body fluid containing a hepcidin protein to be tested is then added to the solid phase complex and incubated at 25° C. for a period of time sufficient to allow binding of any hepcidin protein present to the antibody specific for hepcidin protein. The second antibody is then added to the solid phase complex and incubated at 25° C. for an additional period of time sufficient to allow the second antibody to bind to the primary antibody-antigen solid phase complex. The second antibody is linked to a reporter molecule, the visible signal of which is used to indicate the binding of the second antibody to any antigen in the sample. By "reporter molecule", as used in the present specification is meant a molecule which by its chemical nature, provides an analytically detectable signal which allows the detection of antigen-bound antibody. Detection must be at least relatively quantifiable, to allow determination of the amount of antigen in the sample, this may be calculated in absolute terms, or may be done in comparison with a standard (or series of standards) containing a known normal level of antigen.

The most commonly used reporter molecules in this type of assay are either enzymes or fluorophores. In the case of an enzyme immunoassay an enzyme is conjugated to the second antibody, often by means of glutaraldehyde or periodate. As will be readily recognized, however, a wide variety of different conjugation techniques exist, which are well known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. In all cases, the enzyme-labeled antibody is added to the first antibody-hepcidin protein complex and allowed to bind to the complex, and then the excess reagent is washed away. A solution containing the appropriate substrate is then added to the tertiary complex of antibody-antigen-labeled antibody. The substrate reacts with the enzyme linked to the second antibody, giving a qualitative visual signal, which may be further quantitated, usually spectrophotometrically, to give an evaluation of the amount of antigen that is present in the serum sample.

Alternately, fluorescent compounds, such as fluorescein or rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. As in the enzyme immunoassay (EIA), the fluorescent-labelled antibody is allowed to bind to the first antibody-hepcidin protein complex. After washing the unbound reagent, the remaining ternary complex is then exposed to light of the appropriate wavelength, and the fluorescence observed indicates the presence of the antigen. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

Alternatively, the sample to be tested either human blood or spinal fluid containing a hepcidin protein may be used in a single site immunoassay wherein it is adhered to a solid substrate either covalently or noncovalently. An unlabeled anti-hepcidin protein antibody is brought into contact with the sample bound on the solid substrate. After a suitable period of incubation, for a period of time sufficient to allow formation of an antibody-antigen binary complex a second antibody, labelled with a reporter molecule capable of inducing a detectable signal, is then added and incubation is continued allowing sufficient time for the formation of a ternary complex of antigen-antibody-labeled antibody. For the single site immunoassay, the second antibody may be a general antibody (i.e., zenogeneic antibody to immunoglobulin, particularly anti-(IgM and IgG) linked to a reporter molecule) that is capable of binding an antibody that is specific for a hepcidin protein of interest.

A hepcidin gene (mutated or normal) can be utilized in an assay of iron metabolism. The gene is expressed, with or without any accompanying molecules, in cell lines or primary cells derived from human or animal subjects, healthy subjects, or cells from other organisms (such as rodents, insects, bacteria, amphibians, etc.). Uptake of iron by these cells is measured, for example through the use of radioactive isotopes. Further, binding of iron to a hepcidin gene product can also be measured. Such experiments assist in assessing the role of a hepcidin gene and hepcidin gene product in iron uptake, binding, and transport by and in cells.

Therapeutic Treatment

In one aspect of the invention, the hepcidin diagnostic methods and kits can be used in genetic technological approaches, such as for over expressing or down regulating hepcidin. In certain therapeutic applications, it is desirable to down regulate the expression and/or function of a hepcidin gene, a mutant hepcidin gene, a hepcidin protein, or a mutant hepcidin protein. For example, down regulation of a normal hepcidin gene or a normal hepcidin protein is desirable in situations where iron is under accumulated in the body, for example in certain anemias (i.e., anemia by bleeding or renal anemia). On the other hand, upregulation of a hepcidin gene or a hepcidin protein is desirable in situations where iron is over-accumulated in the body because hepcidin inhibits iron absorption.

Among the diseases which may be suitable for treatment with hepcidin or fragments thereof are the diseases described elsewhere in this application. These diseases may optionally be accompanied by non-physiological hepcidin or prohepcidin levels. Suitable non-representative examples of the diseases include, but are in no way limited to, hemochromatosis, hemosiderosis, and primary and/or secondary iron overload.

As discussed above antibodies specific to a normal or a mutant hepcidin protein can be prepared. Such antibodies can be used therapeutically in the diseases described herein. For example, the antibodies can be used therapeutically to block the action of a hepcidin protein that leads to a decrease of body iron. In a similar manner, a hepcidin gene, either in a normal or in a mutant form, can be down regulated through the use of antisense oligonucleotides directed against the gene or its transcripts. A similar strategy can be utilized as discussed above in connection with antibodies. For a particularly valuable review of the design considerations and use of antisense oligonucleotides, see Uhlmann et al., (1990) Chemical Reviews 90:543-584, the disclosure of which is hereby incorporated by reference. The antisense oligonucleotides of the present invention may be synthesized by any of the known chemical oligonucleotide synthesis methods. Such methods are generally described, for example, in Winnacker Chirurg (1992) 63:145. Antisense oligonucleotides are most advantageously prepared by utilizing any of the commercially available, automated nucleic acid synthesizers. One such device, the Applied Biosystems 380B DNA Synthesizer, utilizes beta-cyanoethyl phosphoramidite chemistry.

Since the complete nucleotide synthesis of DNA complementary to a hepcidin gene is known, the mRNA transcript of the cDNA sequence is also known. As such, antisense oligonucleotides hybridizable with any portion of such transcripts may be prepared by oligonucleotide synthesis methods known to those skilled in the art. While any length oligonucleotide may be utilized in the practice of the invention, sequences shorter than 12 bases may be less specific in hybridizing to the target mRNA, may be more easily destroyed by enzymatic digestion, and may be destabilized by enzymatic digestion. Hence, oligonucleotides having 12 or more nucleotides are preferred. Long sequences, particularly sequences longer than about 40 nucleotides, may be somewhat less effective in inhibiting translation because of decreased uptake by the target cell. Thus, oligomers of 12-40 nucleotides are preferred, more preferably 15-30 nucleotides, most preferably 18-26 nucleotides. Sequences of 18-24 nucleotides are most particularly preferred.

In one embodiment, the antisense therapy may be accomplished by siRNA or shRNA treatment. SiRNAs are typically short (19-29 nucleotides), double-stranded RNA molecules that cause sequence-specific degradation of complementary target mRNA known as RNA interference (RNAi) (Bass, *Nature* 411:428 (2001)).

Accordingly, in some embodiments, the siRNA molecules comprise a double-stranded structure comprising a sense strand and an antisense strand, wherein the antisense strand comprises a nucleotide sequence that is complementary to at least a portion of a desired nucleic acid sequence (i.e., hepcidin mRNA) and the sense strand comprises a nucleotide sequence that is complementary to at least a portion of the nucleotide sequence of said antisense region, and wherein the sense strand and the antisense strand each comprise about 19-29 nucleotides.

Any desired nucleic acid sequence can be targeted by the siRNA molecules of the present invention. Nucleic acid sequences encoding hepcidin are publicly available from Genbank. In one embodiment, the target is a human hepcidin mRNA.

The siRNA molecules targeted to desired sequence can be designed based on criteria well known in the art (e.g., Elbashir et al., *EMBO J.* 20:6877 (2001)). For example, the target segment of the target mRNA preferably should begin with AA (most preferred), TA, GA, or CA; the GC ratio of the siRNA molecule preferably should be 45-55%; the siRNA molecule preferably should not contain three of the same nucleotides in a row; the siRNA molecule preferably should not contain seven mixed G/Cs in a row; the siRNA molecule preferably should comprise two nucleotide overhangs (preferably TT) at each 3' terminus; the target segment preferably should be in the ORF region of the target mRNA and preferably should be at least 75 bp after the initiation ATG and at least 75 bp before the stop codon; and the target segment preferably should not contain more than 16-17 contiguous base pairs of homology to other coding sequences.

Based on some or all of these criteria, siRNA molecules targeted to desired sequences can be designed by one of skill in the art using the aforementioned criteria or other known criteria (e.g., Gilmore et al., *J. Drug Targeting* 12:315 (2004); Reynolds et al., *Nature Biotechnol.* 22:326 (2004); Ui-Tei et al., *Nucleic Acids Res.* 32:936 (2004)). Such criteria are available in various web-based program formats useful for designing and optimizing siRNA molecules (e.g., Sidesign Center at Dharmacon; BLOCK-IT RNAi Designer at Invitrogen; siRNA Selector at WISTAR Insitute; siRNA selection program at Whitehead Institute; siRNA Design at Integrated DNA Technologies; siRNA Target Finder at Ambion; AND siRNA Target Finder at Genscript). Accordingly, a person of skill in the art may just find suitable siRNA sequences by entering the desired template sequence (in this case, the mRNA sequence for hepcidin, including, without limitation, human hepcidin) into one or more of the software programs listed above.

SiRNA molecules targeted to desired sequences can be produced in vitro by annealing two complementary single-stranded RNA molecules together (one of which matches at least a portion of a desired nucleic acid sequence) (e.g., U.S. Pat. No. 6,506,559) or through the use of a short hairpin RNA (shRNA) molecule which folds back on itself to produce the requisite double-stranded portion (Yu et al., *Proc. Natl. Acad. Sci. USA* 99:6047 (2002)). Such single-stranded RNA molecules can be chemically synthesized (e.g., Elbashir et al., *Nature* 411:494 (2001)) or produced by in vitro transcription using DNA templates (e.g., Yu et al., *Proc. Natl. Acad. Sci. Usa* 99:6047 (2002)). When chemically synthesized, chemical modifications can be introduced into the siRNA molecules to improve biological stability. Such modifications include phosphorothioate linkages, fluorine-derivatized nucleotides, deoxynucleotide overhangs, 2'-O-methylation, 2'-O-allylation, and locked nucleic acid (LNA) substitutions (Dorset and Tuschl, *Nat. Rev. Drug Discov.* 3:318 (2004); Gilmore et al., *J. Drug Targeting* 12:315 (2004)).

SiRNA molecules targeted to desired target sequences can be introduced into cells to inhibit expression. The siRNA molecules are introduced into a cell expressing hepcidin (for example, a pancreatic cell or a kidney cell).

In one embodiment, the synthesis of oligonucleotides makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 mmol scale protocol with a 2.5 min coupling step for 2'-O-methylated nucleotides and a 45 second coupling step for 2'-deoxy nucleotides or 2'-deoxy-2'-fluoro nucleotides. Syntheses at the 0.2 mmol scale can be performed on a 96-well plate synthesizer, such as the instrument produced by Protogene (Palo Alto, Calif.) with minimal modification to the cycle. A 33-fold excess (60 mL of 0.11 M=6.6 mmol) of 2'-O-methyl phosphoramidite and a 105-fold excess of S-ethyl tetrazole (60 mL of 0.25 M=15 mmol) can be used in each coupling cycle of 2'-O-methyl residues relative to polymer-bound 5'-hydroxyl. A 22-fold excess (40 mL of 0.11 M=4.4 mmol) of deoxy phosphoramidite and a 70-fold excess of S-ethyl tetrazole (40 mL of 0.25 M=10 mmol) can be used in each coupling cycle of deoxy residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); and oxidation solution is 16.9 mM I.sub.2, 49 mM pyridine, 9% water in THF (PerSeptive Biosystems, Inc.). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide, 0.05 M in acetonitrile) is used.

Deprotection of the DNA-based oligonucleotides is performed as follows: the polymer-bound trityl-on oligoribonucleotide is transferred to a 4 mL glass screw top vial and suspended in a solution of 40% aqueous methylamine (1 mL) at 65° C. for 10 minutes. After cooling to −20° C., the supernatant is removed from the polymer support. The support is washed three times with 1.0 mL of EtOH:MeCN:H$_2$O/3:1:1, vortexed and the supernatant is then added to the first supernatant. The combined supernatants, containing the oligoribonucleotide, are dried to a white powder.

The siRNA molecules can be introduced into cells in vivo by direct delivery into specific organs such as the kidneys or the pancreas, or systemic delivery into the blood stream or nasal passage using naked siRNA molecules or siRNA molecules encapsulated in biodegradable polymer microspheres (Gilmore et al., *J. Drug Targeting* 12:315 (2004)).

Alternatively, siRNA molecules targeted to specific mRNA sequences can be introduced into cells in vivo by endogenous production from an expression vector(s) encoding the sense and antisense siRNA sequences. Accordingly, another aspect of the present invention provides an expression vector comprising at least one DNA sequence encoding a siRNA molecule corresponding to at least a portion of hepcidin mRNA nucleic acid sequence capable of inhibiting expression of a specific mRNA in a cell operably linked to a genetic control element capable of directing expression of the siRNA molecule in a cell. Expression vectors can be transfected into cells using any of the methods described above.

Genetic control elements include a transcriptional promoter, and may also include transcription enhancers to elevate the level of mRNA expression, a sequence that encodes a suitable ribosome binding site, and sequences that terminate transcription. Suitable eukaryotic promoters include constitutive RNA polymerase II promoters (e.g., cytomegalovirus (CMV) promoter, the SV40 early promoter region, the promoter contained in the 3' long terminal repeat of Rous sarcoma virus (RSV), the herpes thymidine kinase (TK) promoter, and the chicken beta-actin promoter), cardiac-tissue-specific RNA polymerase II promoters (e.g., the ventricular myosin light chain 2 (MLC-2V) promoter, and the sodium-calcium exchanger gene H1 promoter (NCX1H1)), and RNA polymerase III promoters (e.g., U6, H1, 7SK AND 7SL).

In some embodiments, the sense and antisense strands of siRNA molecules are encoded by different expression vectors (i.e., cotransfected) (e.g., Yu et al., *Proc. Natl. Acad. Sci. USA* 99:6047 (2002). In other embodiments, the sense and antisense strands of siRNA molecules are encoded by the same expression vector. The sense and antisense strands can be expressed separately from a single expression vector, using either convergent or divergent transcription (e.g., Wang et al., *Proc. Natl. Acad. Sci. USA* 100:5103 (2003); Tran et al., *BMC Biotechnol.* 3:21 (2003)). Alternatively, the sense and antisense strands can be expressed together from a single expression vector in the form of a single hairpin RNA molecule, either as a short hairpin RNA (shRNA) molecule (e.g., Arts et al., *Genome Res.* 13:2325 (2003)) or a long hairpin RNA molecule (e.g., Paddison et al., *Proc. Natl. Acad. Sci. USA* 99:1443 (2002)).

Although numerous expression vectors can be used to express siRNA molecules in cells (Dorsett AND Tuschl, *Nat. Rev. Drug Discov.* 3:318 (2004)), viral expression vectors are preferred, particularly those that efficiently transduce human cells (e.g., alphaviral, lentiviral, retroviral, adenoviral, adenoassociated viral (AAV)) (Williams and Koch, *Annu. Rev. Physiol.* 66:49 (2004); Del Monte and Hajjar, *J. Physiol.* 546.1:49 (2003).

Following introduction of the desired siRNA molecules into cells, changes in desired gene product levels can be measured if desired. Desired gene products include, for example, desired mRNA and desired polypeptide, and both can be measured using methods well-known to those skilled in the art. For example, desired mRNA can be directly detected and quantified using, e.g., Northern hybridization, in situ hybridization, dot and slot blots, or oligonucleotide arrays, or can be amplified before detection and quantitation using, e.g., polymerase chain reaction (PCR), Reverse-Transcription-PCR (RT-PCR), PCR-Enzyme-Linked Immunosorbent Assay (PCR-ELISA), or ligase chain reaction (LCR).

Desired polypeptide (or fragments thereof) can be detected and quantified using various well-known immunological assays, such as, e.g., enzyme-linked immunosorbent assay (ELISA), radioimmunoassay (RIA), immunoprecipitation, immunofluorescence, and Western blotting. Anti-hepcidin antibodies may be produced, for example, by the methods described in the instant application.

The present invention further relates to methods of treating various diseases disclosed herein which comprises administering to a human or animal patient or subject showing non-physiological hepcidin or prohepcidin levels and/or activity a therapeutically effective amount of a molecule or substance as to modulate or promote either an increase or decrease in iron levels within the patient or subject so as to bring the level of pro-hepcidin or hepcidin to within normal physiological levels. For example, patients with a primary or seconday iron overload may be administered a therapeutically effective amount of hepcidin, hepcidin-fragments, hepcidin-derivatives, and/or prohepcidin, so as to effectively lower iron levels to physiological levels. On the other hand, a patient showing decreased iron levels (i.e., non-physiological iron levels on the low end of the scale) may be administered a molecule or substance which lowers pro-hepcidin and/or hepcidin levels and/or activity so as to effect iron retention within the patient. Also, any such therapy may be combined with administration of an iron source so as to better promote a rise in the patient's iron level to physiologically normal levels. One embodiment of this portion of the invention indicates, but in no way limits, the use of these methods to treat various types of hemochromatosis and hemosiderosis. Such methodology becomes even more appropriate in view of the link between glucose and iron levels disclosed herein.

As used herein, "modulating" pro-hepcidin and/or hepcidin ranges from initiating to shutting down, and within that range includes enhancing significantly or slightly to inhibiting significantly or slightly, so as to effect the level of iron within the patient. The term "inhibiting" includes a down regulation which may reduce or eliminate the function of mature hepcidin. For example, a given patient's condition (iron overload) may require an initiation of hepcidin-like activity to effectively modulate iron levels in the patient to physiological levels; whereas another patients condition (iron deficiency) may require an inhibition of hepcidin-like activity so that patient may also modulate iron levels to acceptable, physiological levels. Also, the term "subject" or "patient" may be used interchangeably and shall mean any animal belonging to phylum Chordata, including, without limitation, humans.

The term "treating" or "treatment" of a disease refers to executing a protocol, which may include administering one or more molecules, substances, drugs, etc, to a patient or subject in an effort to alleviate signs or symptoms of the disease, such as an iron overload or iron deficiency. Alleviation can occur prior to signs or symptoms of the disease appearing, as well as after their appearance, as per results of various assays disclosed herein. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the subject (such as at least a positive movement away from non-physiological iron levels towards physiological iron levels within the patient).

Diseases of glucose metabolism such as diabetes mellitus are mostly associated with elevated body iron status, and diseases of iron overload are often accompanied by type 2 diabetes. The molecular mechanism of mutual relationship between iron and glucose metabolisms remain enigmatic. Provided herein is evidence that the body iron and glucose profile is connected by the hepcidin. Hepcidin is specifically expressed in pancreatic β-cells and co-localized with insulin in secretory granules. Stimulation of β-cells with glucose induces co-secretion of insulin and hepcidin with parallelly increasing serum concentrations. Beyond the known effect of insulin on glucose metabolism, increases of hepcidin serum concentrations lead to a decrease of body iron stores as evidenced stressing the ambiguous glucose/iron-regulatory function of the pancreatic β-cell. The expression of hepcidin in β-cells at the transcriptional and translational levels is likewise under control of both iron and glucose. Data disclosed herein clearly show the impact of pancreatic hepcidin in linking glucose and iron metabolisms, thus providing insight into the phenomenology of glucose/iron metabolic disorders such as in hereditary hemochromatosis, an iron overload disease with abnormal glucose homeostasis and decreased insulin secretion.

It is disclosed and discussed herein that expression of hepcidin in β-cells is regulated by iron as well as by glucose. Stimulation of RINm5F cells with 100 mM glucose significantly yielded an up to eightfold increase of hepcidin expression; in contrast, parallel experiments with the hepatocyte-derived cell line HepG2 revealed no changes of hepcidin expression under glucose treatment. The clear responsive difference between pancreatic RINm5F and hepatic HepG2 cells on glucose stimulation is evident. Thus, these data definitely show that hepcidin expression in pancreatic β-cells is specifically induced and regulated by glucose. The effect of glucose on hepcidin secretion was verified in a glucose tolerance test in humans. Increasing serum glucose levels resulted in parallel increases of serum insulin and hepcidin concentrations. This co-secretory pattern completely fits with the co-localization of both peptides in β-cell secretory granules and unequivocally demonstrates that glucose not only regulates insulin but also hepcidin secretion into the serum. Thus, the data disclosed herein show that hepcidin is expressed in pancreatic β-cells under the control of glucose and iron and that the secretion of hepcidin and insulin is linked and co-regulated. This underlines the dual function of pancreatic β-cells in balancing systemic glucose and iron. In view of the fact that the pancreas is one of the main organs affected by hemochromatosis, the expression of iron-regulatory peptide hepcidin in the pancreas opens up new vistas in the physiology of iron/glucose regulation and phenomenology of iron storing diseases at the pancreatic β-cell level.

Therefore, as discussed herein, the instant application discloses that hepcidin is expressed in mammalian (e.g., rat and human) pancreatic β-cells and is co-localized with insulin in secretory granules. The instant application also discloses that pancreatic hepcidin is regulated by iron and glucose. More specifically, hepcidin expression was down-regulated when concentrations of a source of iron (Iron Nitrilotriacetate, or FENTA), of 65 μm or higher were used, even if the concentrations of FENTA were not cytotoxic as shown in a neutral red assay. Moreover, expression and/or secretion of pancreatic hepcidin is induced by glucose, both in vivo and in vitro. In fact, 30 min and 60 min after oral glucose application the serum hepcidin levels increased significantly to 137 and 158%. Accordingly, in another embodiment, the invention provides a method of increasing hepcidin concentration in a subject in need thereof, the method comprising administering the subject a therapeutic agent which is either glucose itself or which stimulates an increase in concentration of glucose in blood. Such agent may cause a release of glucose from body storages (e.g., increase production of glucose from glycogen, or the agent may metabolize into glucose. Suitable non-limiting examples of the latter therapeutic agents include carbohydrates such as sucrose or fructose. Suitable non-limiting examples of the agents which increase production of glucose from glycogen include glucagon and epinephrin.

In still another aspect of the invention, hepcidin can be used in the therapy of the disorders described herein, by treating subjects with hepcidin, and agonists or antagonists of hepcidin. For example, iron uptake in cells can be modulated by varying the concentration of hepcidin. Accordingly, hepcidin, and agonists or antagonists of hepcidin may be useful in the treatment of conditions where there is a disturbance in iron metabolism. For example, such substances may be useful in the treatment of conditions such as haemochromatosis, neurodegenerative diseases, ischemic tissue damage, including ischemic stroke or trauma, heart disease, and tumors, in particular, skin cancer, sideroblastic anemia, thalassemia; hematologic diseases, such as leukemia, polyglobulie, macrocytic, microcytic or normocytic anemia, anemia with reticulocytosis, hemolytic anemia; disturbances of the reticuloendothelial system due to infections and diseases; inflammations and infections, including sepsis; immunologic diseases and tumors, such as carcinoma, sarcoma, lymphoma, that result in non-physiologic hepcidin concentrations; neurodegenerative diseases, such as Alzheimer's disease and Wilson's disease, renal anemia, anemia of chronic diseases, anemia in Crohns disease, anemia in ulcerative colitis, sprue, cholangitis, primary or secondary sclerosing cholangitis, chronic polyarthritis, thalassemia, and iron overload after iron substitution and such other diseases described herein. Some have evidence of the end organ injury seen with prolonged iron overload including liver cirrhosis, arthritis, diabetes, and hypogonadism. Fleming et al., Proc. Natl. Acad. Sci. USA 99, 10653-10658 (2002).

The invention also contemplates methods of modulating iron metabolism using hepcidin. In particular, the present invention relates to a method for treating conditions involving disturbances in iron metabolism comprising administering an iron-modulating amount of hepcidin, or a stimulant, agonist or antagonist of hepcidin. Conditions involving disturbances in iron metabolism which may be treated using the method of the invention include by way of example haemochromatosis, neurodegenerative diseases, ischemic tissue damage, including ischemic stroke or trauma, heart disease, and tumors, in particular skin cancer and such other diseases described herein. A substance which is an agonist or antagonist of hepcidin may be identified by determining the effect of the substance on the binding activity of hepcidin to ferroportin or the effect of the substance on the expression of hepcidin in cells capable of expressing hepcidin including cells genetically engineered to express hepcidin on their surface.

The invention therefore in one aspect relates to a method of identifying agonists or antagonists of hepcidin comprising reacting a substance suspected of being an agonist or antagonist of hepcidin with hepcidin and ferroportin under conditions such that hepcidin is capable of binding to ferroportin; measuring the amount of hepcidin bound to ferroportin; and determining the effect of the substance by comparing the amount of hepcidin bound to ferroportin with an amount determined for a control.

The invention also relates to a method of identifying agonists or antagonists of hepcidin comprising reacting a substance suspected of being an agonist or antagonist of hepcidin with a cell which produces hepcidin, measuring the amount of hepcidin expressed by the cell, and determining the effect of the substance by comparing the amount of expression of hepcidin with an amount determined for a control. The invention further relates to a method for identifying an agonist or antagonist of hepcidin-mediated iron uptake comprising: incubating a cell expressing hepcidin on its surface and a substance suspected of being an agonist or antagonist of hepcidin in the presence of iron and in the absence of transferrin, measuring the amount of iron uptake into the cell, and identifying an agonist or antagonist of hepcidin-mediated iron uptake by comparing the amount of iron uptake in the cell with the amount of iron uptake in a cell from a control incubation in the absence of the substance.

In some embodiments of the invention, hepcidin peptides are provided for therapeutic use in subjects having symptoms of a primary iron overload disease or syndrome, such as hemochromatosis, or other iron overload condition caused by secondary causes, such as repeated transfusions. A hepcidin peptide can be full-length hepcidin or some fragment of hepcidin. Preferably, a hepcidin peptide comprises the amino acid residues 28 to 47 (SEQ ID NO: 8) or 60 to 84 of a 84 amino acid long hepcidin (SEQ ID NO: 2). The predicted amino acid sequence and genomic and cDNA sequences of hepcidin were provided in (Krause et al., (2000) FEBS Lett. 480, 147-150; Pigeon et al., (2001) J. Biol. Chem. 276, 7811-7819), hereby incorporated by reference in their entirety. A hepcidin protein or fragment thereof may be administered with beta-2-microglobulin, such as in the form of a complex. In some embodiments, a hepcidin protein greater than about 20 amino acids is administered in a complex with beta-2-microglobulin.

In some embodiments of the invention, agonists or antagonists of a hepcidin protein or a transferrin receptor are provided. Agonists of a hepcidin polypeptide, and/or antagonists of a transferrin receptor, are useful for example, in the treatment of primary or secondary iron overload diseases or syndromes, while antagonists of a hepcidin polypeptide, or agonists of the transferrin receptor are useful, for example, in the treatment of iron deficiency conditions, such as anemias. In other embodiments, mutant hepcidin proteins/peptides are provided which function as antagonists of the wild-type hepcidin protein. Antagonists or agonists can also be antibodies, directed against a transferrin receptor, or the mid-portion (amino acids 20 to 50) or C-terminal region (amino acids 60 to 84) of a hepcidin protein. In some embodiments of the invention, hepcidin polypeptides can serve as antagonists of a transferrin receptor. In further embodiments of the invention, peptidomimetics can be designed using techniques well known in the art as antagonists or agonists of a hepcidin protein and/or a transferrin receptor.

In one embodiment, the antibodies of the instant invention (e.g., the antibodies capable of binding SEQ ID NO:2, SEQ ID NO:3, SEQ ID NO:4, SEQ ID NO:5) may be used to inactivate hepcidin. In one embodiment, EcR293 cells were stably transfected with a plasmid containing an ecdysone-regulated Ferroportin-GFP (Fpn-GFP) construct (Nemeth et al. Science 306:2090-2093, (2004)). In resulting HEK293-Fpn cells bioactive hepcidin binds to ferroportin and specifically induces the internalization of Fpn-GFP. Briefly, Fpn-GFP was induced by ponasterone treatment for 24 h. Cells were then incubated with 0.1 to 0.5 µM purified human hepcidin (from urine) for 6 h and imaged by epi-fluorescence microscopy. Addition of hepcidin to Fpn-GFP expressing cells changed the distribution of Fpn-GFP from the cell surface to punctuate intracellular vesicles. When hepcidin was absent from the medium, there was no internalization of Fpn-GFP.

Concentrations of hepcidin as low as 0.1 µM induced Fpn internalization within 1 h. Hepcidin was chemically synthesized and the same experiments were performed. Chemically synthesized hepcidin was as efficient in inducing Fpn-GFP internalization as hepcidin purified from urine.

Addition of monoclonal hepcidin antibodies, detecting hepcidin specifically, showed no change of the localization of cell surface Fpn-GFP. In the presence of monoclonal hepcidin antibodies, which bind to hepcidin in the medium, no internalization of Fpn-GFP by hepcidin was observed. These data clearly show that monoclonal antibodies can specifically bind to hepcidin and inactivate it.

Ligands for ferroportin, whether antagonists or agonists, can be screened using the techniques described herein for the ability to bind to ferroportin. Additionally, competition for hepcidin binding to ferroportin can be done using techniques well known in the art. Ligands, or more generally, binding partners for a hepcidin protein can be screened, for example, for the ability to inhibit the complexing of a hepcidin polypeptide to beta-2-microglobulin, using techniques described herein.

In some embodiments of the invention, agonists or antagonists of ferroportin are similarly utilized to increase or decrease the amount of iron transported into a cell, such as into a patient's hepatocytes or lymphocytes. For example, the efficacy of a drug, therapeutic agent, agonist, or antagonist can be identified in a screening program in which modulation is monitored in in vitro cell systems. Host cell systems that express various mutant hepcidin proteins/peptides and are suited for use as primary screening systems. Candidate drugs can be evaluated by incubation with these cells and measuring cellular functions dependent on a hepcidin gene or by measuring proper hepcidin protein folding or processing. Such assays might also entail measuring receptor-like activity, iron transport and metabolism, gene transcription or other upstream or downstream biological function as dictated by studies of hepcidin gene function.

Alternatively, cell-free systems can be utilized. Purified hepcidin protein can be reconstituted into artificial membranes or vesicles and drugs screened in a cell-free system. Such systems are often more convenient and are inherently more amenable to high throughput types of screening and automation.

Criteria for the determination of the purity of a hepcidin protein include those standard to the field of protein chemistry. These include N-terminal amino acid determination, one and two-dimensional polyacrylamide gel electrophoresis, and silver staining. The purified protein is useful for use in studies related to the determination of secondary and tertiary structure, as aid in drug design, and for in vitro study of the biological function of the molecule.

In some embodiments of the invention, drugs can be designed to modulate a hepcidin gene and a hepcidin protein activity from knowledge of the structure and function correlations of a known hepcidin protein. For this, rational drug design by use of X-ray crystallography, computer-aided molecular modeling (CAMM), quantitative or qualitative structure-activity relationship (QSAR), and similar technologies can further focus drug discovery efforts. Rational design allows prediction of protein or synthetic structures that can interact with and modify a hepcidin protein activity. Such structures may be synthesized chemically or expressed in biological systems. This approach has been reviewed in Capsey et al., Genetically Engineered Human Therapeutic Drugs, Stockton Press, New York (1988). Further, combinatorial libraries can be designed, synthesized and used in screening programs.

In order to administer therapeutic agents based on, or derived from, the present invention, it will be appreciated that suitable carriers, excipients, and other agents may be incorporated into the formulations to provide improved transfer, delivery, tolerance, and the like.

A multitude of appropriate formulations can be found in the formulary known to all pharmaceutical chemists: Remington's Pharmaceutical Sciences, (15$^{th}$ Edition, Mack Publishing Company, Easton, Pa. (1975)), particularly Chapter 87, by Blaug, Seymour, therein. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

Any of the foregoing formulations may be appropriate in treatments and therapies in accordance with the present invention, provided that the active agent in the formulation is not inactivated by the formulation and the formulation is physiologically compatible.

The invention is not limited to the embodiments described herein and may be modified or varied without departing from the scope of the invention.

EXAMPLES

Tissue and Tissue Preparation

Human liver samples (n=7) used in the present study were obtained after hemi-hepatectomy in adult subjects with liver metastases. Healthy tissues were fixed in 4% paraformaldehyde for immunohistochemistry or immediately frozen in liquid nitrogen for RT PCR, Western blot and immunofluorescence analysis.

Guinea pigs (n=7) and mice (n=S) were anesthetized and subsequently sacrificed by cervical dislocation. Tissue specimens from liver, skeletal muscle and heart were resected and immediately frozen in liquid nitrogen for Western blot analysis or fixed in paraformaldehyde.

Peptide Synthesis, Immunization Procedure, and Antibodies

From the published prohepcidin sequence (Krause et al., (2000) FEBS Lett. 480, 147-150; Pigeon et al., (2001) J. Biol. Chem. 276, 7811-7819), the peptides hepcidin-(28-47) and hepcidin-(70-84) were synthesized as C terminal amides using a standard Fmoc protocol (Cetin et al., (1994), Proc. Natl. Acad. Sci. USA 91, 2935-2939; Atherton and Shepard, (1989) in *Solid Phase Peptide Synthesis*, eds. Rickwood, D. & Hames, B. D. (IRL, Oxford)). Solid phase peptide synthesis, developed by R. B. Merrifield, was a major breakthrough allowing for the chemical synthesis of peptides and small proteins and is well known in the art. In the general scheme of solid phase peptide synthesis an insoluble polymer support (resin) is used to anchor the peptide chain as each additional alpha-amino acid is attached. This polymer support is constructed of 20-50 µm diameter particles which are chemically inert to the reagents and solvents used in solid phase peptide synthesis. These particles swell extensively in solvents, which makes the linker arms more accessible.

Organic linkers attached to the polymer support activate the resin sites and strengthen the bond between the (-amino acid and the polymer support. Chloromethyl linkers, which were developed first, have been found to be unsatisfactory for longer peptides due to a decrease in step yields. The PAM (phenylacetamidomethyl) resin, because of the electron withdrawing power of the acid amide group on the phenylene ring, provides a much more stable bond than the classical resin. Another alternative resin for peptides under typical peptide synthesis conditions is the Wang resin. This resin is generally used with the FMOC labile protecting group (i.e., Fluorenylmethyloxycarbonyl). FMOC is a base labile protecting group which is easily removed by concentrated solutions of amines (usually 20-55% piperidine in N-methylpyrrolidone). When using FMOC alpha-amino acids, an acid labile (or base stable) resin, such as an ether resin, is desired.

The stable blocking group protects the reactive functional group of an amino acid and prevents formation of complicated secondary chains. This blocking group must remain attached throughout the synthesis and may be removed after completion of synthesis. When choosing a stable blocking group, the labile protecting group and the cleavage procedure to be used should be considered.

After generation of the resin bound synthetic peptide, the stable blocking groups are removed and the peptide is cleaved from the resin to produce a "free" peptide. In general, the stable blocking groups and organic linkers are labile to strong acids such as TFA. After the peptide is cleaved from the resin, the resin is washed away and the peptide is extracted with ether to remove unwanted materials such as the scavengers used in the cleavage reaction. The peptide is then frozen and lyophilized to produce the solid peptide. This is then characterized by HPLC and MALDI before being used by the investigator. It may also be necessary to purify the peptide by HPLC if higher purity is required by the investigator.

The peptides hepcidin-(28-47) and hepcidin-(70-84) were coupled to keyhole limpet hemocyanin using m-maleimidobenzoyl-N-hydroxysuccinimide ester, and two SPF rabbits (Charles River Iffa Credo) were immunized with each peptide conjugate (Eurogentec, Seraing, Belgium). After testing the titer by ELISA, three antisera [EG(1)-HepC directed against hepcidin-(70-84) and EG(1)-HepN and EG(2)-HepN, each directed against hepcidin-(28-47) were used in the present study (hepcidin 28-47: PQQ TGQ LAE LQP QDR AGA RA (SEQ ID NO: 8), hepcidin 70-84: CGC CHR SKC GMC CKT (SEQ ID NO: 9)). The peptide epitopes used for the generation of the antisera displayed no homology to any hitherto reported protein as confirmed by the BLAST P2 search.

The BT-TFR21 S antibody against mouse TfR2 (BioTrend, Cologne, Germany) was raised against the cytoplasmic N-terminus of mouse TfR2-alpha (TfR2) is alternatively spliced to alpha and beta isoforms, see Fleming et al., (2000) Proc. Natl. Acad. Sci. USA 97, 2214-2219), showing 68% sequence homology to the corresponding region of human TfR2-alpha. The antibody was generated in rabbits and affinity purified.

Expression Analyses in the Human Liver

RNA isolation was performed using Qiagen RNA easy kit including DNA digestion. Reverse transcription (RT)-PCR analysis was performed as described previously (Kulaksiz et al., (2002) Proc. Natl. Acad. Sci. USA 99, 6796-6801; Kulaksiz et al., (2002) Am. J. Pathol. 161, 655-664) using the following primers and specifications given in 5-3' orientation: human hepcidin (GenBank database accession no. NM0211175), 5'-CTG CAA CCC CAG GAC AGA G-3' (SEQ ID NO:10) and 5, GGA ATA AAT AAG GAA GGG AGG GG-3' (SEQ ID NO:11), corresponding to nucleotide positions 147-165 and 338-316. Human TfR2 (#AF067864), 5'-GAT TCA GGG TCA GGG AGG TG-3' (SEQ ID NO:12) and 5'-(GAA GGG GCT GTG ATT GAA GG-3'(SEQ ID NO:13); corresponding to nucleotide positions 2496-2515 and 2694-2675. After an initial denaturation of 94° C. for 4 min; reactions were subjected to 35 cycles of the following thermal program: 94° C. for 30 s, 60° C. for 30 s, and 72° C. for 30 s; this program was followed by a final 5 min elongation step at 72° C. Amplification products were run on an ethidium bromide-stained 1.8% 89 mM Tris/89 mM boric acid/2 mM EDTA (pH 8.3) agarose gel. The amplification of significant levels of genomic DNA was excluded by appropriate controls.

Expression Analyses 1N HEPG2 Cells

The human hepatoma HepG2 cells were obtained from the German Collection of Microorganisms and Cell Culture (Braunschweig, Germany) and grown at 37° C. in 5% CO2 in RPMI 1640 media (Gibco, Karlsruhe, Germany) supplemented with 10% (vol/vol) heat-inactivated FBS, penicillin (100 units/ml), and streptomycin (100 mg/ml). Cells were analyzed by RT PCR using the primer specifications mentioned above. For immunofluorescence microscopy, HepG2 cells were grown on glass slides fixed for 4 mm in methanol, and permeabilized with 0.5% Triton X-100 in PBS. After incubation with hepcidin (1:2000) and TfR2 antibodies (1:1000) for 60 min, followed by incubation with Cy-3-conjugated anti-rabbit antibody (Dianova, Hamburg, Germany), the immunostaining was investigated under an Olympus AX70 microscope using appropriate filters.

Extraction of Hepcidin and TFR2 from Tissues and HEPG2 Cells

For hepcidin analysis, frozen tissues and HepG2 cells were mixed in 1 M acetic acid and boiled for 8 mm as described (Cetin et al., (1994), Proc. Natl. Acad. Sci. USA 91, 2935-2939; Cetin et al., (1995) Proc. Natl. Acad. Sci. USA 92, 5925-5929). After homogenization with an Ultra-Turrax homogenizer (Janke & Kunkel, Staufen, Germany) the samples were centrifuged at 20,000×g for 20 mm at 4° C. and the supernatants were filtered through a 0.45-mm pore size filter. To enrich proteins, cell and total tissue extracts were applied to an octadecasilyl (C 18) Sep-Pak cartridge (Waters, Mass.). The column was washed with 0.01 M HCl and eluted with 30% (vol/vol) 2-propanol/300 (vol/vol) methanol 0.01 M HCl (Cetin et al., (1994), Proc. Natl. Acad. Sci. USA 91, 2935-2939). Protein fractions were lyophilized and stored at −80° C. until use. For TfR2 analysis, tissues and cells were homogenized in Tris-HCl buffer containing 100 mM NaCl, 50 mM Tris-HCl, pH 7.4, 10% glycerol, 1% Triton X-100, 2 mg/ml leupeptin, 2 mg/ml pepstatin, and 1 mM phenylmethylsulfonyl fluoride, and centrifuged at 100,000 g for 30 mm at 4° C.

Immunoblot Analysis

For Western blot analysis, protein extracts were incubated for 7 min at 94° C. in sample buffer with 4% (wt/vol) SDS (Merck, Darmstadt, Germany), 50 mM Tris-HCl (pH 8.15), 1 mM EDTA, 3.24 mM dithiothreitol (Roth, Karlsruhe, Germany), 12.5% (wt/vol) glycerol (Merck), and 0.002% bromophenol blue (Merck). To detect hepcidin, a 16.5% tricine-SDS-polyacrylamide gel was used according to the protocols published (Cetin et al., (1994), Proc. Natl. Acad. Sci. USA 91, 2935-2939; Kulaksiz et al., (2002) Proc. Natl. Acad. Sci. USA 99, 6796-6801; Kulaksiz et al., (2002) Am. J. Pathol. 161, 655-664; Cetin et al., (1995) Proc. Natl. Acad. Sci. USA 92, 5925-5929). TfR2 immunoblots were performed using 8% SDS-polyacrylamide gels. Following electrophoresis, proteins were transferred onto hydrophobic polyvinylidene fluoride-based membranes (Pall, Portsmouth, England) by semi-dry blotting. The membranes were incubated overnight with hepcidin or TfR2 antibodies at dilutions mentioned above. After washing in Tris-buffered saline containing 10 mM Tris-HCl (pH 8.0), 150 mM NaCl, and 0.05% Tween 20, the respective immunoreactive proteins were visualized after incubation with alkaline phosphatase-conjugated goat anti-rabbit antibody (diluted 1:50,000; Sigma) using nirro blue tetrazolium and 5-bromo-4-chloro-3-indolyl phosphate as chromogens (Sigma). The immunoreaction on the Western blot was specifically blocked after preincubation of the antibodies with the corresponding peptide immunogens. Cross-reactivity with the second goat anti-rabbit antibody was excluded by appropriate controls (Kulaksiz et al., (2002) Proc. Natl. Acad. Sci. USA 99, 6796-6801; Kulaksiz et al., (2002) Am. J. Pathol. 161, 655-664).

Immunohistochemistry and Immunofluorescence

Tissues were fixed in 4% paraformaldehyde for 18 h at 4° C. After dehydration in graded ethanol series, the specimens were embedded in paraffin. Paraffin sections (5 m) were immunostained for hepcidin (antibodies EG(1)-HepN, Kci(2)-HepN, and EG(1)-HepC, each diluted 1:2000) or TfR2 (antibody BT-TFR21-S. diluted 1:1000) by the avidin-biotin-peroxidase complex (ABC) technique and incubation sequences as previously described (Kulaksiz et al., (2002) Proc. Natl. Acad. Sci. USA 99, 6796-6801; Kulaksiz et al., (2002) Am. J. Pathol. 161, 655-664). The sections were incubated with the respective antibodies for 24 h at 4° C., followed by incubation with biotinylated anti-rabbit IgG (Jackson Immunoresearch, West Grove, Pa., USA) for 30 min diluted 1:200. The sections were then incubated for 30 min with a preformed complex of biotin-peroxidase/streptavidin (Jackson Immunoresearch), diluted in PBS (final concentrations: biotin-peroxidase, 0.7 mg/ml; streptavidin, mg/ml). The antigen-antibody binding sites were visualized by incubation of the sections in 07 mM diaminobenzidine hydrochloride/0.0020% $H_2O_2$ in 0.05 M Tris-HCl pH 7.6).

For immunofluorescence microscopy, tissue sections from human liver (2-4 mm) were prepared with a cryotome (FrigoCut 2800E; Leica, Nussloch, Germany), air dried for 2 hours, and fixed for 10 min in cold acetone (−20° C.). Double-immunofluorescence labeling was performed as described previously (Rost et al., (1999) Hepatology 29, 814-821) using the specific hepcidin antibodies (diluted 1:1000) and monoclonal antibody C219 (id.) raised against canalicular P-glycoproteins (Centocor, Malvern, Pa.) diluted 1:30. After incubation with the respective antisera, staining was performed by incubation with Cy2-(1:200) and Cy3-(1:600) labeled antibodies against mouse and rabbit IgG (Dianova, Hamburg, Germany). Micrographs were taken with an Olympus AX70 microscope equipped with a digital camera (color view 12, soft imaging system SiS, Munster, Germany) and analysis software (SiS, Munster, Germany).

Specificity Controls

Method-dependent non-specificities were excluded by running controls as described (Cetin et al., (1994), Proc. Natl. Acad. Sci. USA 91, 2935-2939; Cetin et al., (1995) Proc. Natl. Acad. Sci. USA 92, 5925-5929). Antibody specificities were tested by preadsorption of the antibodies with homologous and heterologous antigenic peptides (6.25-100 mg/ml of the antiserum) (Kulaksiz et al., (2002) Proc. Natl. Acad. Sci. USA 99, 6796-6801; Kulaksiz et al., (2002) Am. J. Pathol. 161, 655-664). Preadsorption of the antibodies with homologous antigens at concentrations as low as 6.25 mg/ml completely blocked immunostaining in the liver tissues and cells, while preadsorption of the antibodies with heterologous antigens at concentrations up to 100 mg/ml had no effect on immunostaining.

Hepcidin Elisa Competitive Binding Assay

Determinations were performed in duplicate using 96-well-microtiter plates coated with goat anti-rabbit IgG (DRG Instruments GmbH, Marburg, Germany). Hepcidin antibody EG(2)-IJepN, diluted 1.4000 in Tris buffered saline (TBS) containing 40 mM Tris-HCl (pH 7.3), 100 mM NaCl, was pipetted into the microtiter plates. After a 1 hour incubation at room temperature (RT), the microtiter plates were washed with TBST (TBS with 0.05% Tween 20) and 100 ml standard samples containing various amounts of synthetic peptides or human plasma samples (58 randomized samples from our clinical laboratory) and N-terminally biotinylated hepcidin-(28-47) (Peptide Specialty Laboratories GmbH, Heidelberg, Germany) (2 ng/well) were added to each well and incubated for 1 hour at RT. The biotinylated antigen-antibody complexes were detected by streptavidin-peroxidase enzyme (Dako, Hamburg, Germany) with the substrate tetramethylbenzidine (DRG); the color reaction was stopped with 0.5 N $H_2SO_4$ and the extinction of the solution was read at 450/630 nm wavelength.

Expression of Hepcidin and TFR2 in the Liver and HEPG2 Cells

Figure 1:
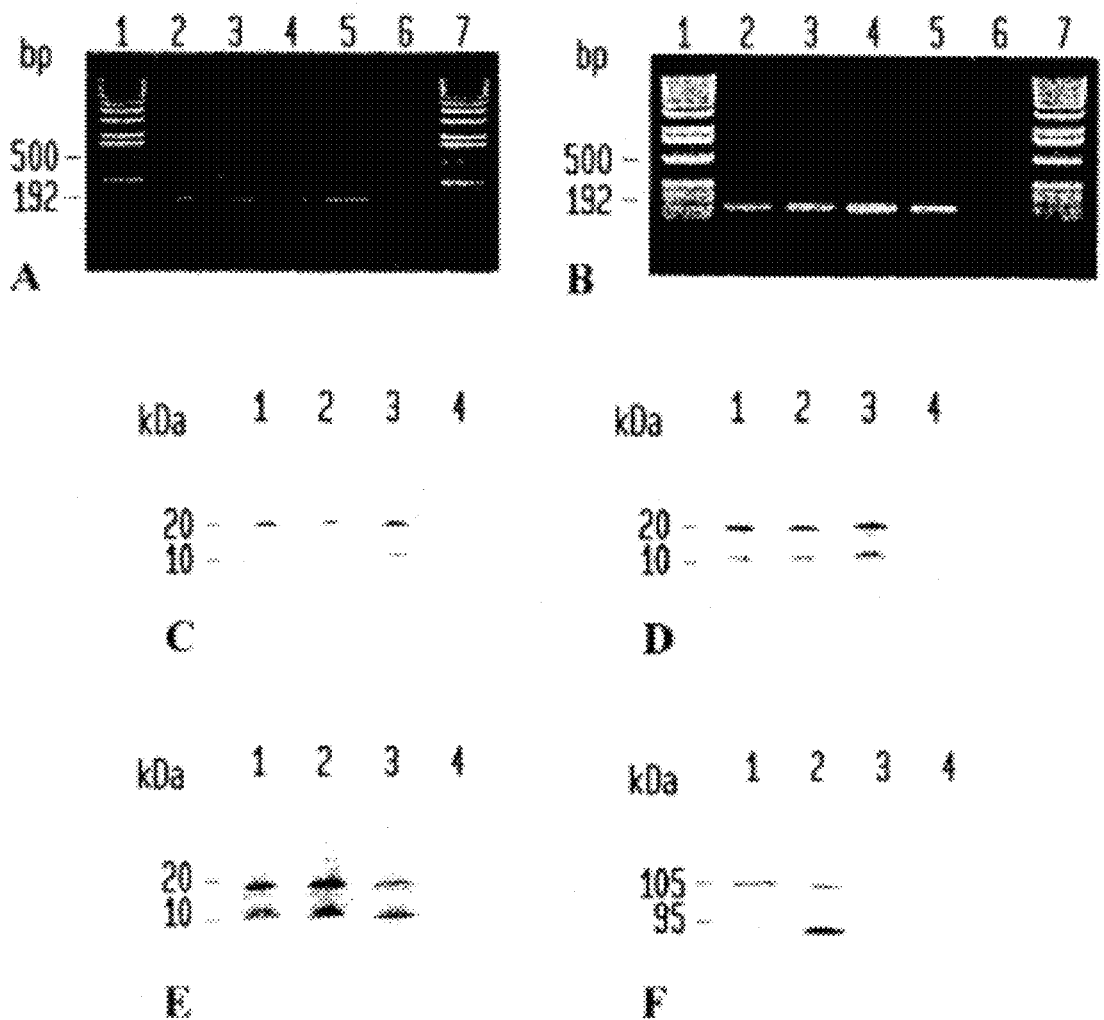
FIG. 1A-F shows RT-PCR analysis of human liver (lanes 2 and 3) and HepG2 cells (lanes 4 and 5) showing gene expression of hepcidin (A) and TfR2 (B) with amplification products of correct molecular size. A by DNA ladder is indicated (lanes 1 and 7). Lanes 6 show a negative control. (C-E) Western blot analyses of hepcidin in extracts of guinea pig (lane 1) and human liver (lane 2) as well as in HepG2 cells (lane 3) and guinea pig skeletal muscle (lane 4, control) with antibodies EG(1)-HepN (C), EG(2)-HepN (D) and EG(1)-HepC (E). Note the immunoreactive bands at 10 and 20 kDa obtained with all antibodies recognizing different epitopes in a hepcidin precursor. (F) Western blot analysis of TfR2 in extracts of mouse liver (1), human liver (2), HepG2 cells (3) and mouse heart (4) (control).

RT-FCR analysis demonstrated that hepcidin is highly expressed in human liver. Similarly, a 192-bp expected transcript was detected in HepG2 cells with an expression level comparable to human liver (FIG. 1). In addition, RT-PCR analyses clearly revealed that TfR2 is highly expressed in the human liver and HepG2 cells (FIG. 1). In Western blot analysis, all hepcidin antibodies [EG(1)-HepN, EG(2)-HepN, and EG(1)-HepC] coincidentally identified an immunoreactive band of about 10 kDa in extracts of human and guinea pig liver. This liver peptide comigrated with an immunoreactive band recognized by a hepcidin antibodies in homogenates of HepG2 cells (FIG. 1). All antibodies also identified an intensively stained band at ~20 kDa in all lanes loaded with human and guinea pig liver extracts or HepG2 cell extracts. Western blot analysis of skeletal muscle extracts (control) showed neither the immunoreactive band of 10 kDa nor the strong band at 20 kDa (FIG. 1).

Western blot analysis with TfR2 antibody BT-TFR21-S resulted in a staining of an expected (Fleming et al., (2000) Proc. Natl. Acad. Sci. USA 97, 2214-2219)about ~105 kDa protein in extracts of mouse liver. In extracts of human liver and HepG 2 cells, a ~95 kDa immunoreactive TfR2 and to lesser extent a ~105 kda immunoreactive protein was recognized by the same antibody (FIG. 1). No immunoreactivity was detected in the heart (control tissue).

Cellular and Subcellular Localization of Hepcidin and TFR2

Figure 2:
FIG. 2A-H shows. cellular localization of hepcidin in guinea pig (A-F) and human (G-I) liver. The paraffin sections immunostained with the region-specific antibodies EG(1)-HepN (A, D, G), EG(2)-HepN (B, E, H) and EG(1)-HepC (C, F, I) show a distinct immunoreactivity at the basolateral membrane domain of hepatocytes (arrows). (Magnification: A-C, X 180; D-I, X 540).
Figure 3:
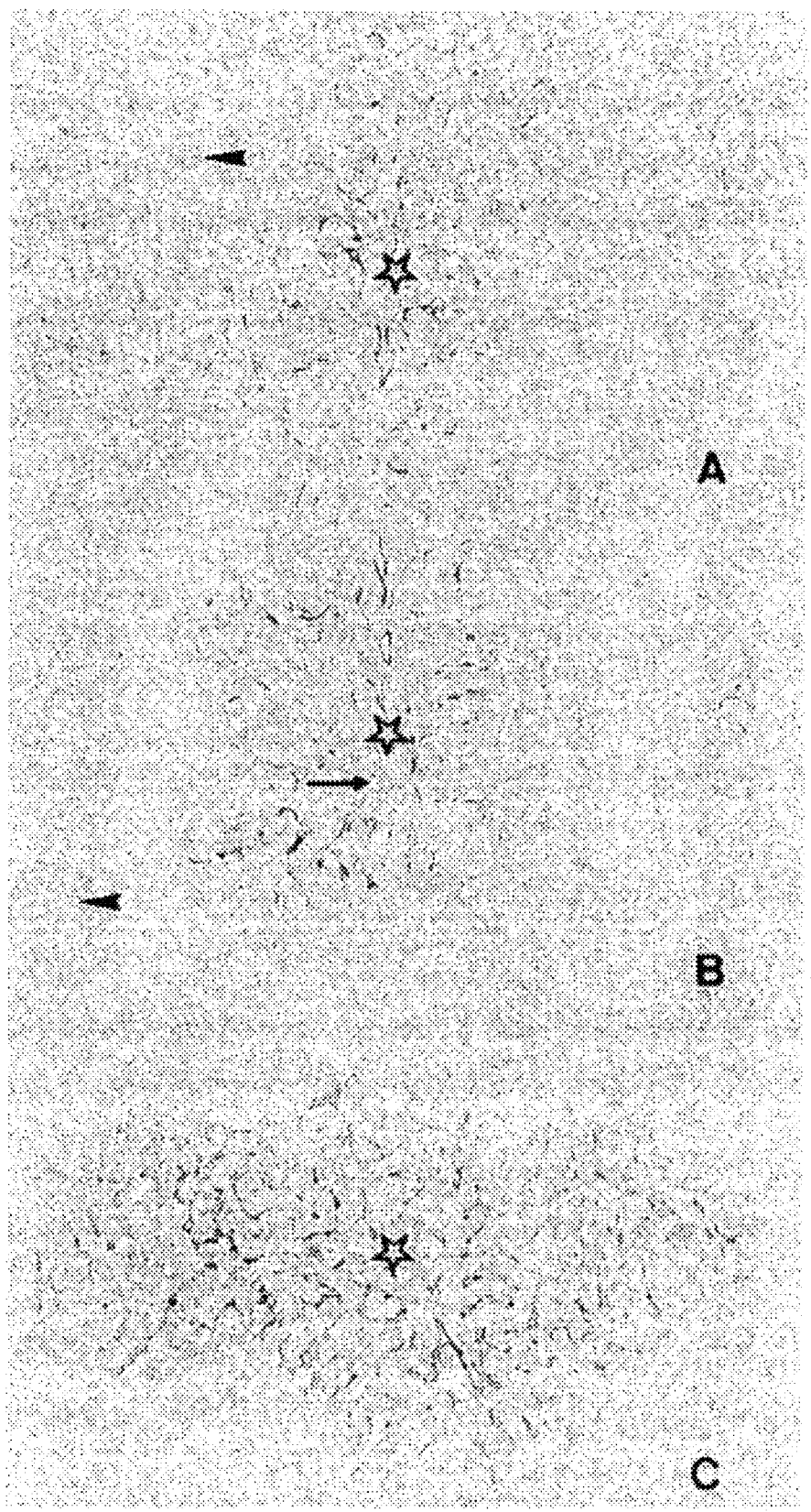
FIG. 3A-C shows immunohistochemical sections (A, antibody EG(1)-HepN; B, antibody EG(2)-HepN: C, antibody EG(1)-HepC showing the clear zonation of hepcidin within the hepatic lobules with decreasing immunoreactivity from periportal zones (stars) towards the central veins (arrowheads). Note that no immunoreactivity is found in hepatocytes around the central veins. (The arrow in B indicates a portal triad.) (A-C, X 180).

Immunohistochemical studies with various region-specific antibodies consistently localized hepcidin to the hepatocytes in human liver (FIG. 2). The Kupffer cells, endothelial cells, bile ducts, and the vascular system completely lacked hepcidin immunoreactivity. The same antibodies detected a strong hepcidin-immunoreactivity also in guinea pig liver (FIG. 2). Interestingly, hepatic lobule, were heterogeneous with respect to a hepcidin immunoreactivity; within a hepatic lobule, a hepcidin immunoreactive cells were predominantly located in periportal zones, and the frequency of hepcidin-positive cells continuously decreased from the portal triads toward the central veins (FIG. 3). Notably, distinct intercellular differences exist between a hepcidin positive cells; while most hepatocytes were strongly positive for hepcidin, others displayed only a faint staining or were totally unreactive for hepcidin (FIG. 3).

At the subcellular level, hepcidin immunoreactivity was confined to the basolateral (=sinusoidal) membrane domain of hepatocytes; no immunoreactivity was found at the apical membrane domain of the respective cells (FIG. 2). Similarly, immunofluorescence analysis demonstrated a strong immunoreactivity for hepcidin at the basolateral membrane domain; immunoreactivity was absent from the apical membrane domain as revealed by double staining with the C219 antibody raised against canalicular P-glycoproteins (Rost et al., (1999) Hepatology 29, 814-821).

Figure 4:
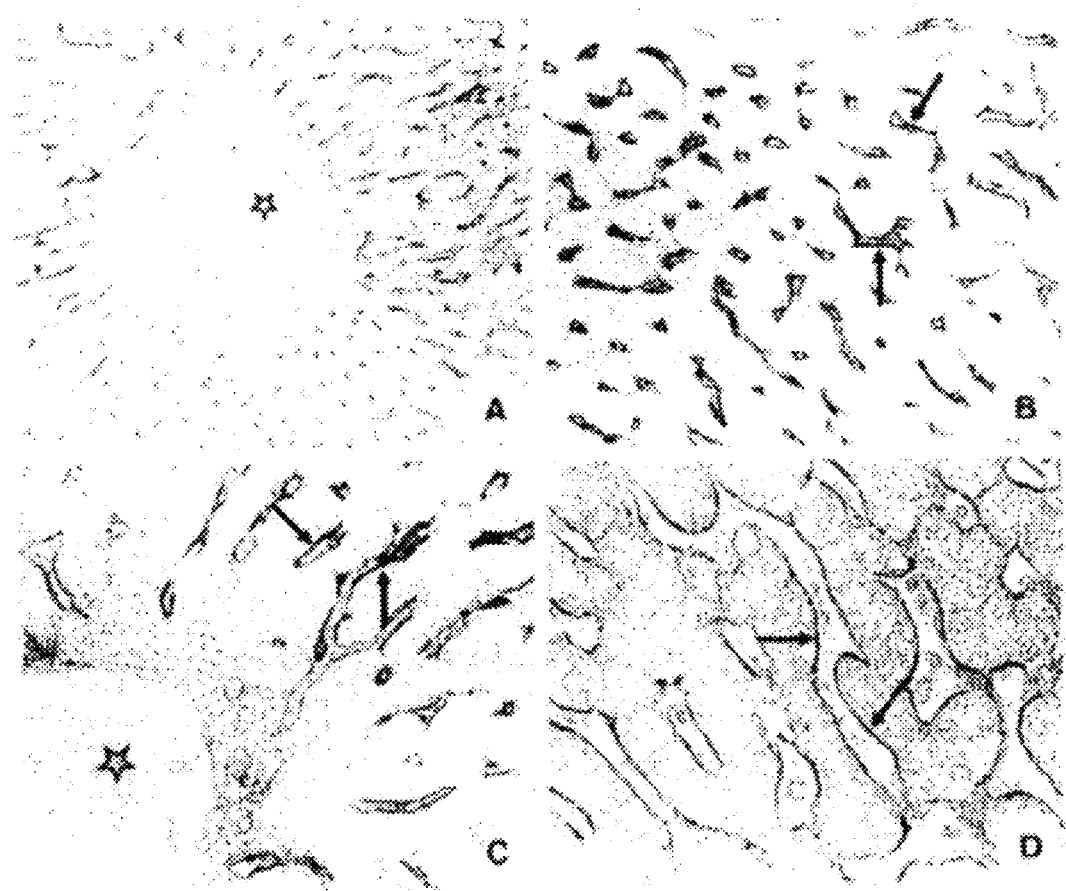
FIG. 4A-D shows immunohistochemical localization of TfR2 in mouse (A-C) and human liver (D) using the antibody BT-TFR21-S. Note that immununoreactivity is exclusively confined to the basolateral membrane (arrows) of hepatocytes; no immunoreactivity is found around the central veins (stars in A and C). A slight zonation for TfR2 is seen in A with decreasing immunoreactivity toward the central vein (A, X 180; B, C, X 360; D, X 540).

Corresponding to the localization of hepcidin, protein-specific antibody BT-TFR21-S detected TfR2 in human and mouse liver. At the cellular level, TfR2 was found at the basolateral membrane of hepatocytes, which revealed distinct intercellular differences concerning the intensity of immunoreactivity (FIG. 4). Heterogeneity was also observed within a hepatic lobule with increasing immunoreactivity from the central veins to the portal triads.

Immunfluorescence 1N HEPG2 Cells

Figure 5:
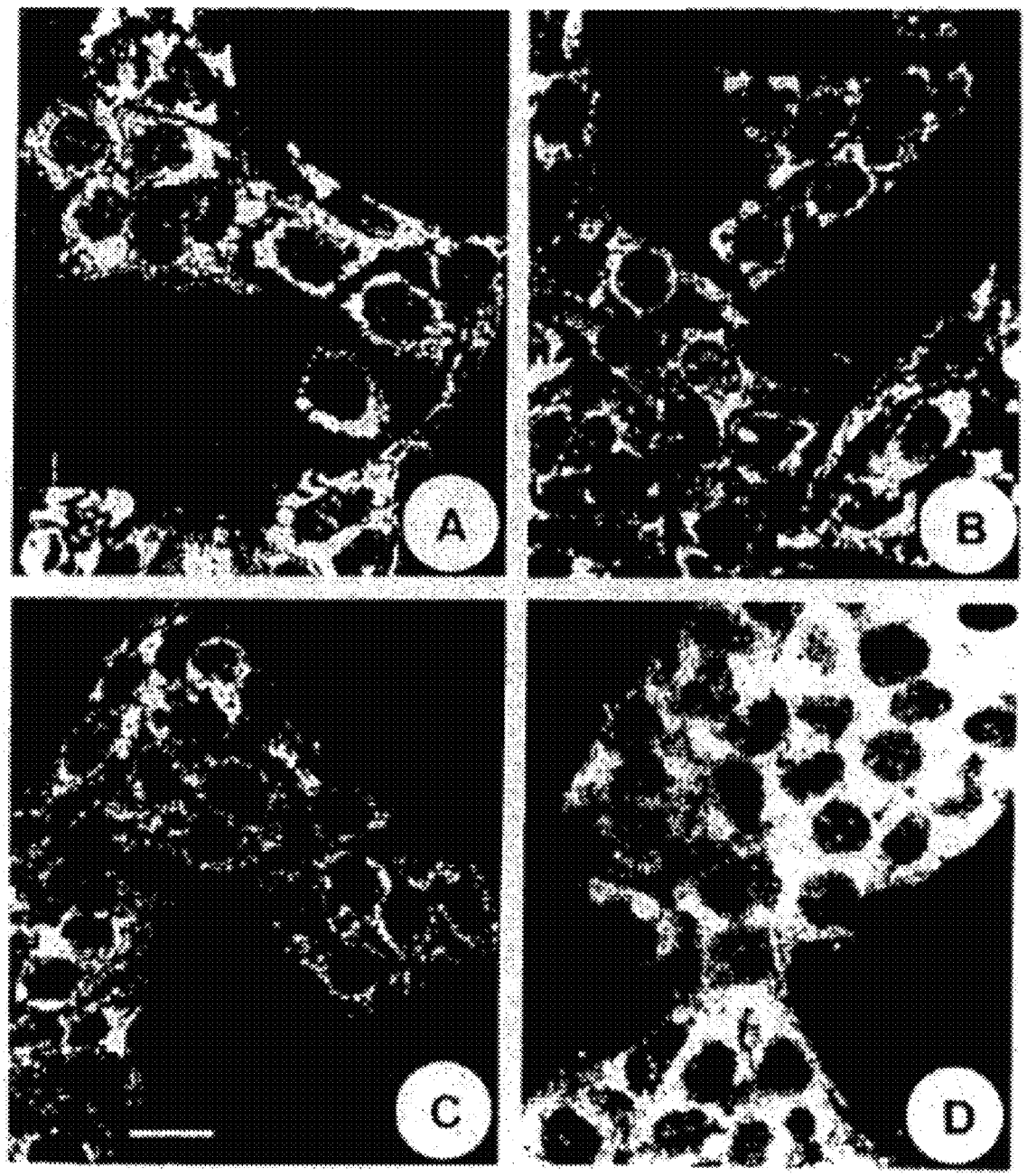
FIG. 5A-D shows detection of hepcidin (A-C) and TfR2 (D) in HepG2 cells by immunofluorescence microscopy using the antibodies EG(1)-HepN (A), EG(2)-HepN (B), EG(1)-HepC (C), and BT-TFR21-S (D) (Scale bar 8 mm).

The existence of hepcidin peptide in HepG2 cells was verified by immunocytochemistry using the corresponding peptide-specific antibodies. All antibodies identified hepcidin by the immunofluorescence technique in HepG2 cells resulting in a granular immunoreactivity pattern (FIG. 5). Coincident with the cellular localization of hepcidin, the TfR2 antibody detected TfR2 in the same cells (FIG. 5).

Detection of Hepcidin Propeptide in Human Plasma

Although the C-terminal antibody EG(1)-HepC revealed specific results in dot blot, Western blot, immunohistochemistry and immunofluorescence experiments (FIGS. 1-5), it did not work in ELISA. The compact folding pattern of hepcidin and its tertiary structure in the blood may account for the inability of the EG(1)-HepC antibody to identify circulating hepcidin. A sensitive hepcidin ELISA assay with a detection limit of 0.1 ng/well of the synthetic peptide was developed with the specific N-terminal hepcidin antibody EG(2)-HepN (FIG. 6). ELISA analyses with this antibody revealed a concentration of hepcidin in the range from 12.1 to 471.3 ng per ml human plasma. No cross-reactivity was observed when heterologous peptides were used. As seen in FIG. 6, the ELISA revealed the highest resolving power between 1 and 400 ng/ml, a range, where hepcidin concentrations in human plasma were determined.

In the present invention, RT-PCR analyses with specific primers confirmed that hepcidin is highly expressed in the human liver. Three different antibodies recognizing different epitopes in a hepcidin precursor molecule concurrently identified an immunoreactive peptide of about 10 kDa by Western blot analysis in liver extracts of two species, man and guinea pig. The apparent molecular mass of this immunoreactive peptide is in accordance with the molecular mass deduced for a hepcidin preprohormone from the cDNA sequence (Pigeon et al., (2001) J. Biol. Chem. 276, 7811-7819). Interestingly, a second immunoreactive band of approximately 20 kDa was detected by all hepcidin antibodies in extracts of the human and guinea pig liver but was lacking in the control tissue. This immunoreactive protein may represent a hepcidin-related peptide of higher molecular mass or, because of the twofold higher molecular mass of the second peptide, it may reflect a dimeric type of hepcidin. In fact, in a previous study an aggregation property and a possible formation of multimers was described for hepcidin-25 but not for hepcidin-20 (Hunter et al., (2002) J. Biol. Chem., 277:37597-37603).

Immunohistochemical and immunofluorescence investigations with three different hepcidin antibodies revealed that, in human and guinea pig liver, hepcidin is specifically localized in hepatocytes mainly located around the portal triads; the coincident staining by different region-specific antibodies not only in the human and guinea pig liver, but also in the HepG2 cells (see below) points to hepatocytes being the source of hepcidin. Hepcidin immunoreactivity decreased from the periportal zones towards the central veins. This zonation within the portal lobules may have a functional significance, since the periportal hepatocytes have first-pass access to portal veins bringing iron-rich blood from the gut. Notably, distinct intercellular differences exist between hepcidin-positive cells even of the same liver acinus with respect to the density of hepcidin immunoreactivity that may reflect intercellular differences in expression or secretion of hepcidin.

At the subcellular level, hepcidin was concentrated at the basolateral pole of hepatocytes. No immunoreactivity was found at the apical membrane domain. The discrete distribution pattern of hepcidin at the subcellular level may infer a basolaterally directed release of hepcidin into the liver sinusoids. This directional secretion route is additionally substantiated by the detection of hepcidin prohormone in human plasma (see below); consequently, these findings provide further evidence that hepatocytes may regulate iron metabolism in an endocrine fashion via the secretion of the peptide hormone hepcidin.

To analyze the expression and cellular distribution of TfR2 as well as the respective target membrane domains, RT-PCR, Western blot and immunohistochemical studies at the cellular level were performed. As shown in previous studies RT-PCR analyses revealed that TfR2 is highly expressed in human liver. (Fleming et al., (2000) Proc. Natl. Acadi. Sci. USA 97, 2214-2219). The presence of this protein was confirmed by Western blot studies using BT-TFR21-S antibody specific to human and mouse TfR2. A ~105 kDa immunoreactive protein was detected in mouse liver extracts; this molecular mass of immunoreactive TfR2 is slightly larger than the expected 95 kDa (Fleming et al., (2000) Proc. Natl. Acadi. Sci. USA 97, 2214-2219) and may represent some posttranslational modifications as described previously (Kawabata et al., (2000) J. Biol. Chem. 275, 16618-16625). Under identical conditions, however, the TfR2-antibody identified the protein at the expected 95 kDa molecular mass and with a lower affinity the 105 kDa protein in human liver extracts. The discrepancy between the immunoblots of human and mouse liver may be due to interspecies differences.

Immunohistochemical investigations revealed that TfR2 is localized to hepatocytes of human and mouse liver; coincident with the cellular distribution of hepcidin, the protein-specific antibody localized TfR2 exclusively at the basolateral membrane. This type of membrane-specific association of TfR2 argues particularly for a basolateral activation of TfR2, which is involved in iron metabolism by binding diferric transferrin and mediating uptake of transferrin-bound iron from the blood into hepatocytes (Philpott, C. C. (2002) Hepatology 35, 993-1001; Subramaniam et al., (2002) Cell Biochem. Biophys. 36, 235-239). Notably, a similar lobular zonation as described for hepcidin was observed for TfR2 with decreasing immunoreactivity from the periportal zones toward the central veins.

Since an interaction between hepcidin and TfR2 at the cellular level has been discussed in previous studies (Nicolas et al., (2001) Proc. Natl. Acad. Sci. USA 98, 8780-8785; Frazer et al., (2002) Gastroenterology 123, 835-844), the coexistence of hepcidin and TfR2 in HepG2 cells-a well-differentiated hepatocellular carcinoma cell line (Aden et al., (1979) Nature 282, 615-616) was analyzed, demonstrating in many aspects the physiology of normal hepatocytes. RT-PCR studies using the appropriate primer specifications and combinations successfully employed in the human liver identified expression of hepcidin and TfR2 in HepG2 cells. At the translational level, the presence of hepcidin and TfR2 in HepG2 cells was confirmed by Western blot studies that yielded immunoreactive protein bands of correct molecular weights, comigrating with the corresponding immunoreactive bands from the liver tissues. The co-localization of the respective proteins in HepG2 cells was particularly substantiated by immunocytochemistry using the corresponding region and molecular domain-specific antibodies. All antibodies demonstrated hepcidin-labeling in HepG2 cells, revealing a granular immunoreactivity pattern in these cells that infers localization of the peptide to small secretory vesicles, already demonstrated in hepatocytes by electron microscopy (Schwartz et al., (1985) EMBO J. 4, 899-904). TfR2 was immunocytochemically localized, with a peculiar distribution pattern, to HepG2 cells.

On the basis of present data at the transcriptional and translational level, hepcidin and TfR2 are coexpressed in the liver and colocalized at the basolateral membrane domain of hepatocytes. In addition to a coincident localization of TfR2 and hepcidin at the cellular level, a similar distribution of these molecules within the hepatic lobules with a concentrated immunoreactivity in periportal zones and a decreasing straining toward the central veins was also detected. The coordinate expression of these proteins in a common (basolateral) membrane domain and their similar lobular zonation argue for a morphofunctional coupling of the regulating peptide hormonohepcidin and the transferrin-bound iron uptake via TfR2. Indeed, different data substantiate the interaction between hepcidin and TfK2. First, alterations in transferrin saturation, probably sensed by TfR2, modulate the expression of hepatic hepcidin (Philpott, C. C. (2002) Hepatology 35, 993-1001). Second, as revealed from quantitative RT-PCR analyses on human liver, hepatic expression of TfR2 correlates significantly with hepcidin expression regulated by the transferrin saturation (S. G. Gehrke, H. Kulaksiz et al. unpublished data). Third, hepcidin and TfR2 are colocalized at a common cell membrane domain and reveal the same lobular distribution with a strong immunoreactivity in periportal zones, the site, where in case of mutations that abrogate expression of TfR2 (Fleming et al., (2002) Proc. Natl. Acad. Sci. USA 99, 10653-10658) and hepcidin (Nicolas et al., (2001) Proc. Natl. Acad. Sci. USA 98, 8780-8785) but also hepcidin (Zhou et al., (1998) Proc. Natl. Acad. Sci. USA 95, 2492-2497; Levy et al., (1999) Blood 94, 9-11) and B2m (Santos et al., (1996) J. Exp. Med. 184, 1975-1985) hepatic iron overloading occurs. The clinical consequences of iron overload include cirrhosis of the liver and hepatocellular cancer, diabetes, heart failure, arthritis, and hypogonadism. Zhou et al., Proc. Natl. Acad. Sci., 95, 2492-2497 (1998). Fourth, mutations in the TfR2 gene were reported to lead to hemoechromatosis (Camasehella et al., (2000) Nat. Genet. 25, 14-15); this may result from decreased hepcidin expression, which, in turn, results in increased iron absorption (Nicolas et al., (2001) Proc. Natl. Acad. Sci. USA 98, 8780-8785). Increased iron absorption in patients suffering from hereditary hemochromatosis leads to accumulation of iron, with eventual tissue damage and organ disfunction. When the disorder remains untreated, premature mortality resulting from hepatocellular carcinoma, cirrhosis, cardiomyopathy, or diabetes mellitus is common. Santos et al., (1996) J. Exp. Med. 184, 1975-1985.

Since blood-forming tissues and sites of iron storage, such as the liver, are thought to transmit signals to the intestinal cells that indicate the body's requirements for dietary iron (Philpott, C. C. (2002) Hepatology 35, 993-1001), hepcidin is a candidate signaling factor secreted from the liver and regulating the intestinal iron absorption. However, there is still controversy about the existence of certain molecular forms of hepcidin in the blood (Krause et al., (2000) FEBS Lett. 480, 147-150; Park et al., (2001) J. Biol. Chem. 276, 7806-7810; Hunter et al., (2002) J. Biol. Chem., M205305200). To analyze whether the prohormone of hepcidin is secreted into the blood, and to assess the range of hepcidin concentration in human plasma, an ELISA was developed by applying the same N-terminal antibody against hepcidin prohormone used successfully in Western blot, immunocytochemical and immunofluorescence experiments. The ELISA was characterized by a high sensitivity with a detection limit of 0.1 ng/well and a powerful resolution in the range of 1 to 400 ng/ml; the range, where hepcidin concentrations were determined. In the human plasma samples tested, the concentration of pro-hepcidin was measured, ranging from 12.1 to 471.3 ng/ml, which is comparable with the concentration of known regulating peptide hormones. The mean concentration of hepcidin in healthy volunteers was 51.6-153.4 ng/mL (106±32.1, mean±SEM, n=26) and approximately 1.2-fold higher than the concentration of hepcidin in human urine (Park, C. H., Valore, E. V., Waring, A. J. & Ganz, T. (2001) J. Biol. Chem. 276, 7806-7810). Interestingly, the measured concentrations exhibit a wide range of pro-hepcidin indicating that the peptide may be subject to strong regulation. Future experiments are intended to determine hepcidin concentrations in plasma of various subjects with disturbances of iron metabolism and to analyze the molecular mechanism of hepcidin regulation using the established ELISA.

The cDNA structure suggests that hepcidin is translated as an 84 amino acid prepropeptide that is N-terminally processed to a 20-25 amino acid peptide (id.). Although a strong consensus sequence for a signal sequence cleavage site is located between $Gly_{24}$ and $Ser_{25}$ that would result in a 60 residue propeptide, previous studies failed to isolate the larger propeptide from native sources like liver tissue and blood (Id.). In addition to technical difficulties, the abundance of propeptide convertases in the liver may inhibit the isolation of certain propeptides. In this context, recent studies have shown that the human circulating form of hepcidin described by two research groups in blood (Krause et al., (2000) FEBS Lett. 480, 147-150) and in urine (Park et al., (2001) J. Biol. Chem. 276, 7806-7810), consists of the C-terminal 20-25 amino acids of the protein. However, the ELISA measurements of the present invention were performed with the specific-antibody raised against the N-terminus of hepcidin precursor, implying that besides the 20-25 amino acid processed forms, a hepcidin prohormone is secreted and circulates in human blood.

To understand the role of hepcidin, the knowledge about the cellular origin and the signaling pathway of the peptide is necessary. In this respect, the present invention describes hepcidin immunoreactivity in human and guinea pig liver, where it is localized to the basolateral membrane domain of hepatocytes. Previous studies have speculated on a possible connection between these cells and the absorptive enterocytes (Hunter et al., (2002) J. Biol. Chem., M205305200; Anderson et al., (2002) Biochem. Soc. Trans. 30, 724-726). The present invention describes the detection of pro-hepcidin in the human plasma thereby indicating that hepatocytes secrete the prohormone of hepcidin that may decrease dietary iron absorption via an endocrine pathway. Moreover, hepcidin was detected in HepG2 cells, where the newly discovered transferrin receptor type 2 was also found. The simultaneous existence of hepcidin and TfR2 in HepG2 cells and their common polarized localization and lobular distribution in the liver may indicate that hepcidin is an intrinsic hepatic peptide morphofunctionally coupled to TfR2, which is regulated by transferrin saturation and, in turn, modulates expression of hepcidin. Hence, pertinent findings are expected from studies on the signaling pathway of hepcidin.

Enzyme Immunoassay for the Quantitative Measurement of Hepcidin in Human or Animal Serum and Other Body Fluids.

In one embodiment of the invention a Hepcidin enzyme immunoassay ("EIA") is used. An EIA is a solid phase enzyme-linked immunosorbent assay (ELISA) based on the competitive principle. Microtiter wells of a 96 well microtiter plate are coated with a polyclonal rabbit anti-hepcidin antibody. An unknown amount of Hepcidin present in the sample and a fixed amount of Hepcidin conjugated with a biotin molecule compete for the binding sites of the Hepcidin antibodies immobilized on the wells. After one hour incubation the microtiter plate is washed to stop the competition reaction. In the following incubation the bound biotin molecules are detected with streptavidin horseradish peroxidase. After one half hour of incubation the plate is washed a second time. Having added the substrate solution the concentration of Hepcidin is inversely proportional to the optical density measured.

Materials
1. Microtiter wells.
   wells coated with Anti-Hepcidin antibody (96 wells).
2. Reagent: Biotin Conjugate (Hepcidin conjugated to biotin) 7 ml.
3. Reference Standard Set, 1.0 ml each
   0, 20, 100, 500, 1000 ng/ml.
4. Reagent: Enzyme Complex (Streptavidin conjugated to horseradish peroxidase ("HRP")) 14 ml.
5. Reagent: Substrate Solution-HS-TMB, 14 ml.
6. Stop Solution, 0.5M $H_2SO_4$, 14 ml.
7. Wash Solution, 40×, 30 ml.
8. A microtiterplate reader (450±10 nm) (e.g., the DRG Instruments Microtiterplate Reader).
9. Precision micropipettes with disposable tips for 50 and 100 µl.
10. Standard refrigerator.
11. Absorbent paper.
12. Deionized water.

While this embodiment has been described in terms of preferred materials, a person skilled in the art of the invention will appreciate that other materials can be used in the invention. For example, one of skill in the art will appreciate that complementary binding moieties other than biotin/streptavidin, as well as enzyme/substrate combinations other than horse radish peroxidase/peroxide, may be used in the invention.

Storage Conditions

When stored at 2° to 8° C. unbroken reagents will retain reactivity until expiration date. Do not use reagents beyond this date. Microtiter wells must be stored at 2° to 8° C. Once the foilbag has been broken care should be taken to close it tightly again. The immuno-reactivity of the coated microtiter wells is stable for approximately 6 weeks in the broken, but tightly closed plastic zip pouch containing the desiccant.

Specimen Collection and Preparation

Human or animal serum or EDTA plasma should be used in the assay. No special pretreatment of the biological sample is necessary. The biological sample may be stored at 2-8° C. for up to 24 hours, and should be frozen at −20° C. or lower for longer periods. Do not use grossly hemolyzed or grossly lipemic specimens. For other sample material a special extraction protocol may be necessary.

Performance of the Assay

General Remarks:

1. All reagents and specimens must be allowed to come to room temperature before use. All reagents must be mixed without foaming.
2. Once the test has been started, all steps should be completed without interruption.
3. Use new disposable plastic pipette tips for each reagent, standard or specimen in order to avoid cross contamination. For the dispensing of the Substrate Solution and the Stop Solution avoid pipettes with metal parts.
4. Pipette standards and samples onto the bottom of the well. For pipetting of Enzyme Conjugate and Stop Solution it is recommended to hold the pipette in a vertical position above the well and dispense the correspondent solution into the center of the well so that a complete mixing of Enzyme Conjugate with sample or standard and of the Stop Solution with the Substrate Solution is achieved.
5. Before starting the assay, it is recommended that all reagents be ready, caps removed, all needed wells secured in holder, etc. This will ensure equal elapsed time for each pipetting step without interruption.
6. As a general rule the enzymatic reaction is linearly proportional to time and temperature. This makes interpolation possible for fixed physico-chemical conditions. If in a test run the absorbance of Zero Standard is lower than 1.0 or above the upper performance limit of your microtiterplate spectrophotometer you can extend or reduce the incubation time of the final enzymatic formation of color to 30 or 10 minutes accordingly. Since calibrators are assayed in each run, absorbance fluctuations do not affect the result.
7. The Substrate Solution should be colorless or slightly blue or green. If the solution is dark blue the reagent is unusable and must be discarded.
8. During incubation with Substrate Solution avoid direct sunlight on the microtiter plate.

Reagent Preparation

Wash Solution: Add deionized water to the 40× concentrated Wash Solution (contents: 30 ml) to a final volume of 1200 ml. The diluted Wash Solution is stable for 2 weeks at room temperature.

Assay Procedure

1. Secure the desired number of coated strips in the holder.
2. Dispense 50 µl of Hepcidin Standards into appropriate wells.
3. Dispense 50 µl of sample into selected wells.
4. Dispense 50 µl of Biotin Conjugate into each well.
5. Thoroughly mix the plate for 10 seconds. It is important to have complete mixing in this step.
6. Incubate for 60 minutes at room temperature.
7. Briskly shake out the contents of the wells.
8. Rinse the wells 3 times with diluted Wash Solution (400 µl per well). Strike the wells sharply on absorbent paper to remove residual droplets.
9. Add 100 µl Streptavidin HRP Complex to all wells.
10. Incubate for 30 minutes at room temperature.
11. Briskly shake out the contents of the wells.
12. Rinse the wells 3 times with diluted Wash Solution (400 µl per well). Strike the wells sharply on absorbent paper to remove residual droplets.
13. Add 100 µl of Substrate Solution to each well, at timed intervals.
14. Incubate for 15 minutes at room temperature.
15. Stop the enzymatic reaction by adding 100 µl of Stop Solution to each well at the same timed intervals as in step 10 and determine the absorbance of each well at 450±10 nm.

Final Reaction Stability

It is recommended that the wells be read within 30 minutes following step 15.

Calculation of Results

Any microwell reader capable of determining the absorbance at 450±10 nm may be used. The Testosterone value of each sample is obtained as follows:

1. Using linear-linear or semi log graph paper, construct an standard curve by plotting the average absorbance (Y) of each Reference Standard against its corresponding concentration (X) in ng/ml. For construction of the standard curve we recommend a four parameter logistic function.

2. Use the average absorbance of each sample to determine the corresponding Testosterone value by simple interpolation from this standard curve, multiplying by the initial sample dilution, if necessary.

A DRG ELIZA MAT 3000 and the DRG Regression Program allow the reading and computer assisted interpretation using a four parameter logistic function.

Preparation of Monoclonal Antibody

From the published human pro-hepcidin sequence (Krause, et al. *Febs Lett.* 480, 147-150 (2000); Pigeon, et al., *J. Biol. Chem.* 276, 7811-7819 (2001)), the peptide hepcidin-(74-81) was synthesized as C terminal amide using a standard FMOC protocol. To avoid the problem with cystein-disulfide-bridges the amino acid cystein at position hepcidin-78 was replaced by the isosteric amino acid alpha aminobutyric acid (Abu).

The immunization peptide was coupled to keyhole limpet hemocyanin using M-maleimidobenzoyl-N-hydroxysuccinimide ester, and mice were immunized with the peptide conjugate.

After producing monoclonal antibodies using standard protocol the titer of the antibodies were tested by ELISA. The antibodies mHK(5), mHK(8/1), mHK(8/2), MHK(8/3), and mHK(9), each directed against hepcidin-(74-Abu-81), were able to identify hepcidin in western blot, immunohistochemistry and elisa experiments.

The peptide epitopes used for the generation of the antibodies displayed no homology to any hitherto reported protein except hepcidin as confirmed by the blast P2 search.

Expression of Hepcidin in the Human and Rat Pancreas

Figure 9:
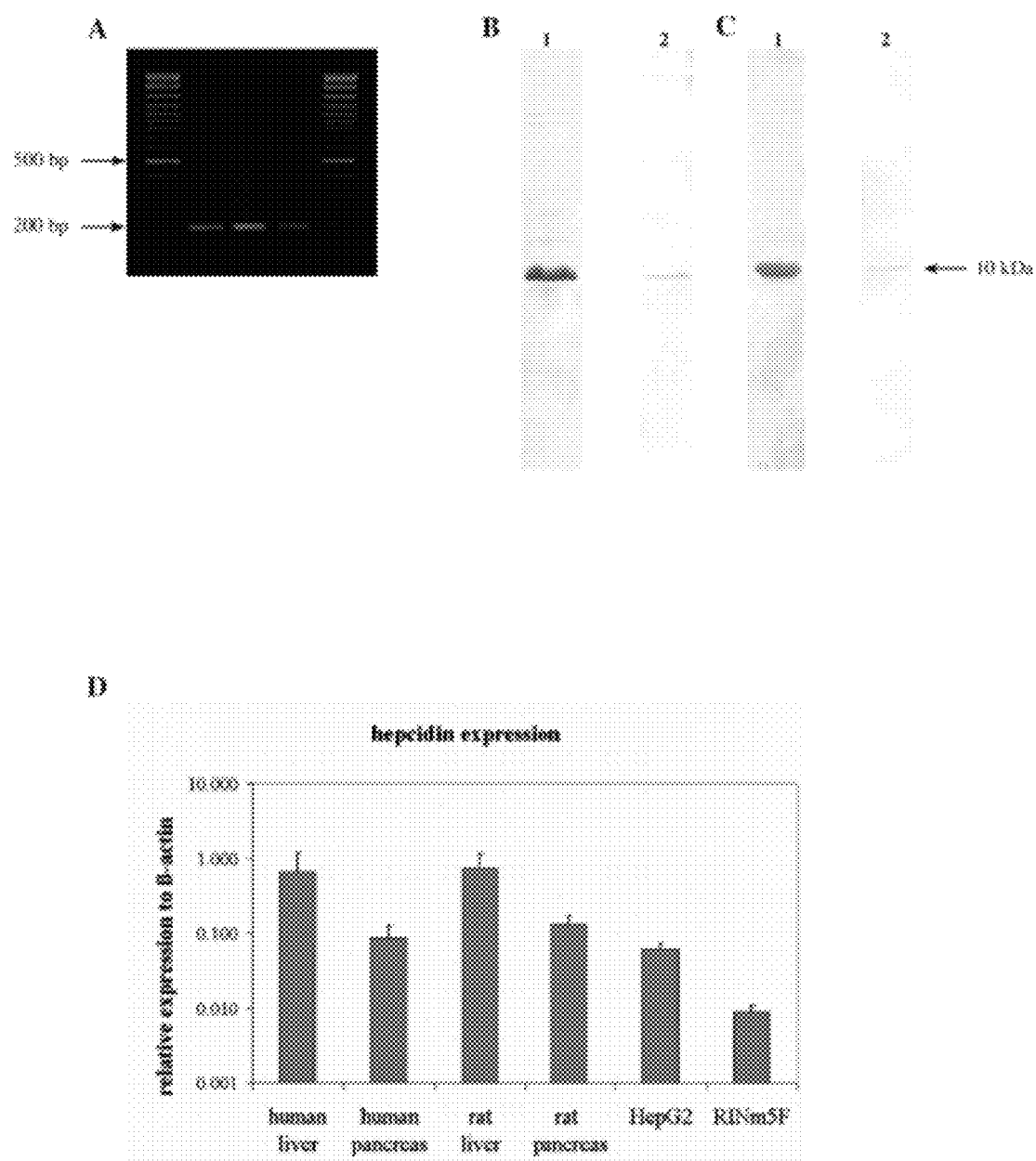
FIG. 9A-D shows that hepcidin is highly expressed in human and rat pancreas. (A): RT-PCR analysis of human pancreas (lane 2), rat pancreas (lane 3) and RIN m5F cells (lane 4). A by DNA ladder is indicated (lanes 1 and 5). (B, C): Immunoblot analysis of hepcidin in extracts of human (lanes 1) and rat (lanes 2) pancreas. Note the immunoreactive peptide bands at 10 kDa obtained with both N- and C-terminal antibodies EG(2)-HepN (B) and EG(2)-HepC (C). D: Quantitative RT-PCR (n=6). The expression levels of hepcidin (means) are given as the amount relative to the expression of the housekeeping gene actin in each sample.
Figure 10:
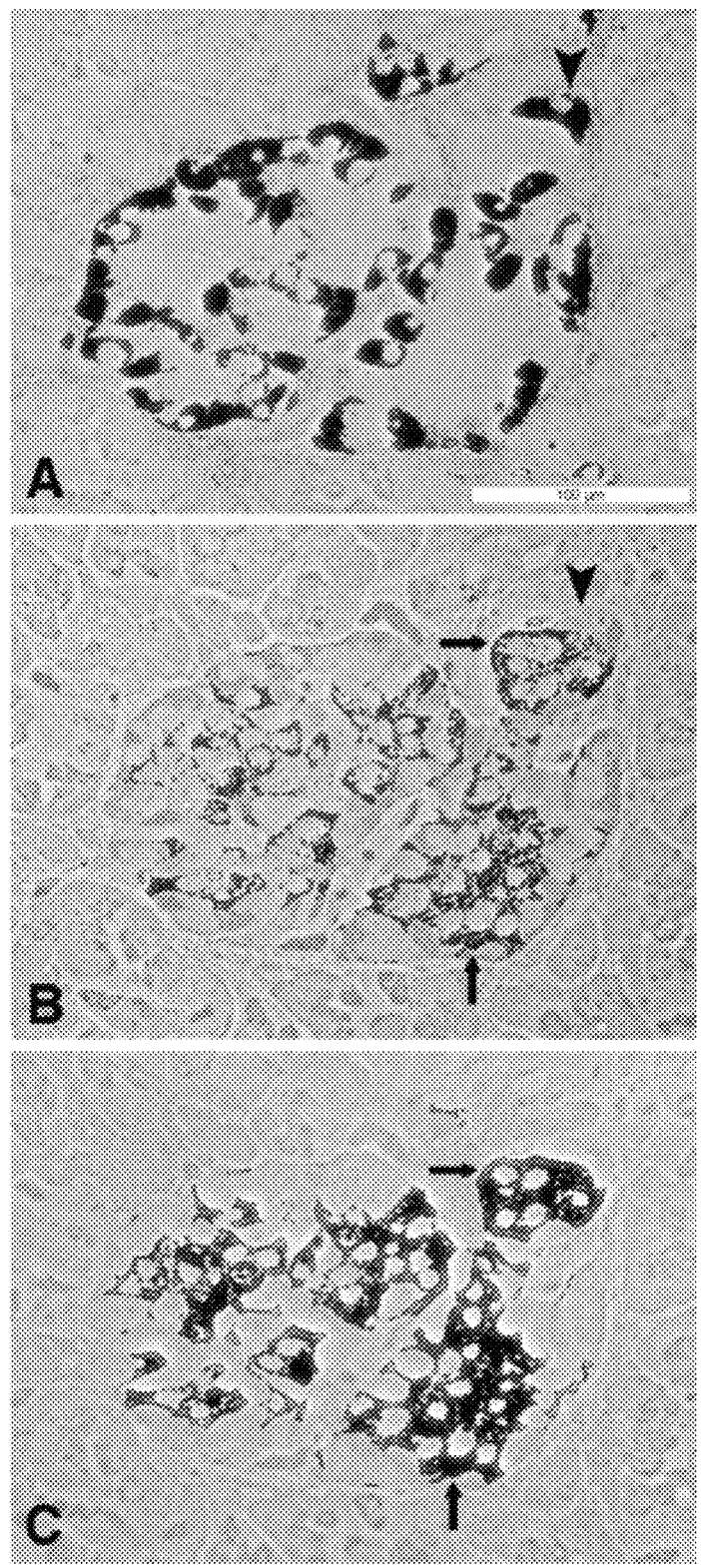
FIG. 10A-C shows cellular and subcellular localization of hepcidin in the pancreas. Three serial semithin (0.5 µm) sections of human pancreas immunostained for glucagon (A), hepcidin (B), and insulin (C). In the pancreatic islet, hepcidin immunoreactivity is exclusively localized to insulin (β-) cells (arrows). No immunoreactivity is found in glucagon (α) cells (arrowheads).
Figure 11:
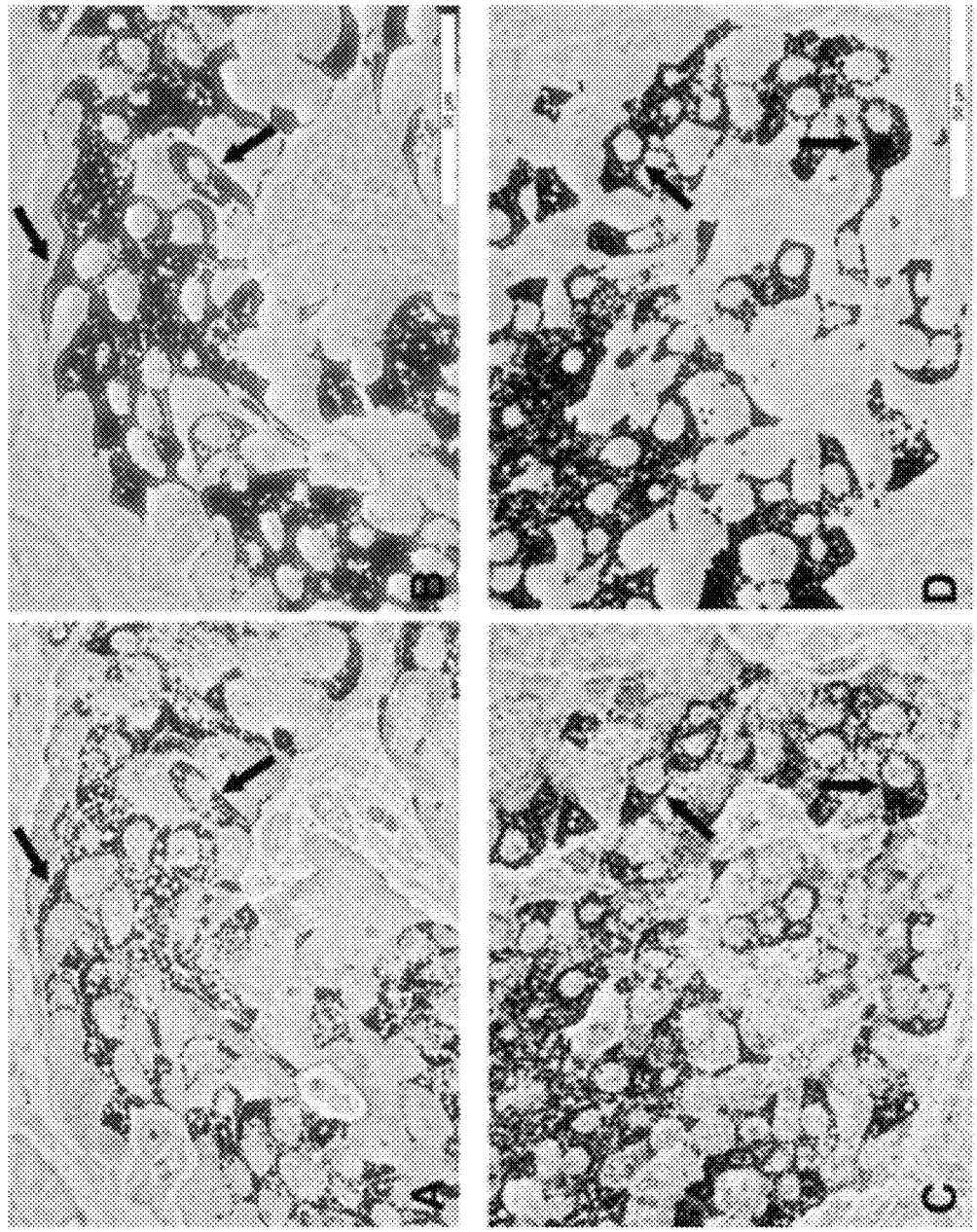
FIG. 11A-D shows that hepcidin is co-localized with insulin within the human Langerhans islets. The granular immunoreactivity pattern for hepcidin is shown with N- and C-terminal hepcidin antisera (EG(2)-HepN (A) and EG(2)-HepC (C)) in serial semithin sections in pancreatic insulin cells (B and D) (arrows). Within the pancreatic islet both hepcidin antisera exhibit a co-localization of hepcidin and insulin in the same cells.

RT-PCR analyses using specific primers revealed that hepcidin is highly expressed in human and rat pancreas (FIG. 9A-D). The amplification yielded an expected transcript of 201 bp (FIG. 9A). Sequence analyses of the amplification products confirmed complete homology with the hepcidin cDNAs of rat and man. As determined by quantitative RT-PCR, the expression of hepcidin in the pancreas was about 13-18% compared to that in the liver (FIG. 9D). The existence of hepcidin at the translational level was verified by immunoblotting analyses in human and rat pancreatic extracts. Both N- (FIG. 9B) and C-terminal region-specific hepcidin antisera (FIG. 9C) concurrently identified the immunoreactive peptide of ~10 KDa. The size of this pancreatic peptide comigrating with the immunoreactive band observed in homogenates of the liver (positive control) corresponds to the molecular mass of hepcidin deduced from the respective cDNA sequence.

RNA isolation was performed using QIAGEN RNAEasy kit including DNA digestion. reverse transcription (RT)-PCR analysis was performed using the following primers and specifications given in 5'-3' orientation: human hepcidin (Genbank database accession no. NM021175), 5'-CCT GAC CAG TGG CTC TGT TT-3'(SEQ ID NO:14) and 5'-GGT TCT ACG TCT TGC AGC AC-3'(SEQ ID NO:15); corresponding to positions 130-149 and 330-311; rat hepcidin (Genbank database accession no. NM053469), 5'-GGC AGA AAG CAA GAC TGA TGA C-3' (SEQ ID NO:16) and 5'-ACA GGA ATA AAT AAT GGG GCG-3'(SEQ ID NO:17); corresponding to positions 146-168 and 346-332.

After an initial denaturation of 94° C. for 4 min, reactions were subjected to 30 cycles of the following thermal program: 94° C. for 30 s, 60° C. for 30 s, and 72° C. for 30 s; this program was followed by a final 5-min elongation step at 72° C. Amplification products were run on an ethidium bromide-stained 1.8% 89 mM TRIS/89 mM boric acid/2 mM EDTA (pH 8.3) agarose gel. The amplification of significant levels of genomic DNA was excluded by appropriate controls. As specificity controls, the amplified PCR products were sequenced on a 377 DNA sequencer (Perkin Elmer).

Hepcidin is Co-Localized with Insulin in Secretory Granules of the Human and Rat Pancreatic β-Cells All hepcidin antisera under study coincidently immunostained distinct cells within the human Langerhans islets which by their typical location within the islets and by co-localization with insulin were clearly identified as β-cells (FIGS. 10A-C and 11A-D). Other endocrine cell types (i.e., glucagon α-, somatostatin σ-, and pancreatic polypeptide PP-cells) or the exocrine gland cells were completely unreactive for hepcidin. The same cellular distributive pattern was found in the rat pancreas where strong hepcidin immunoreactivity was detected in β-cells.

Figure 12:
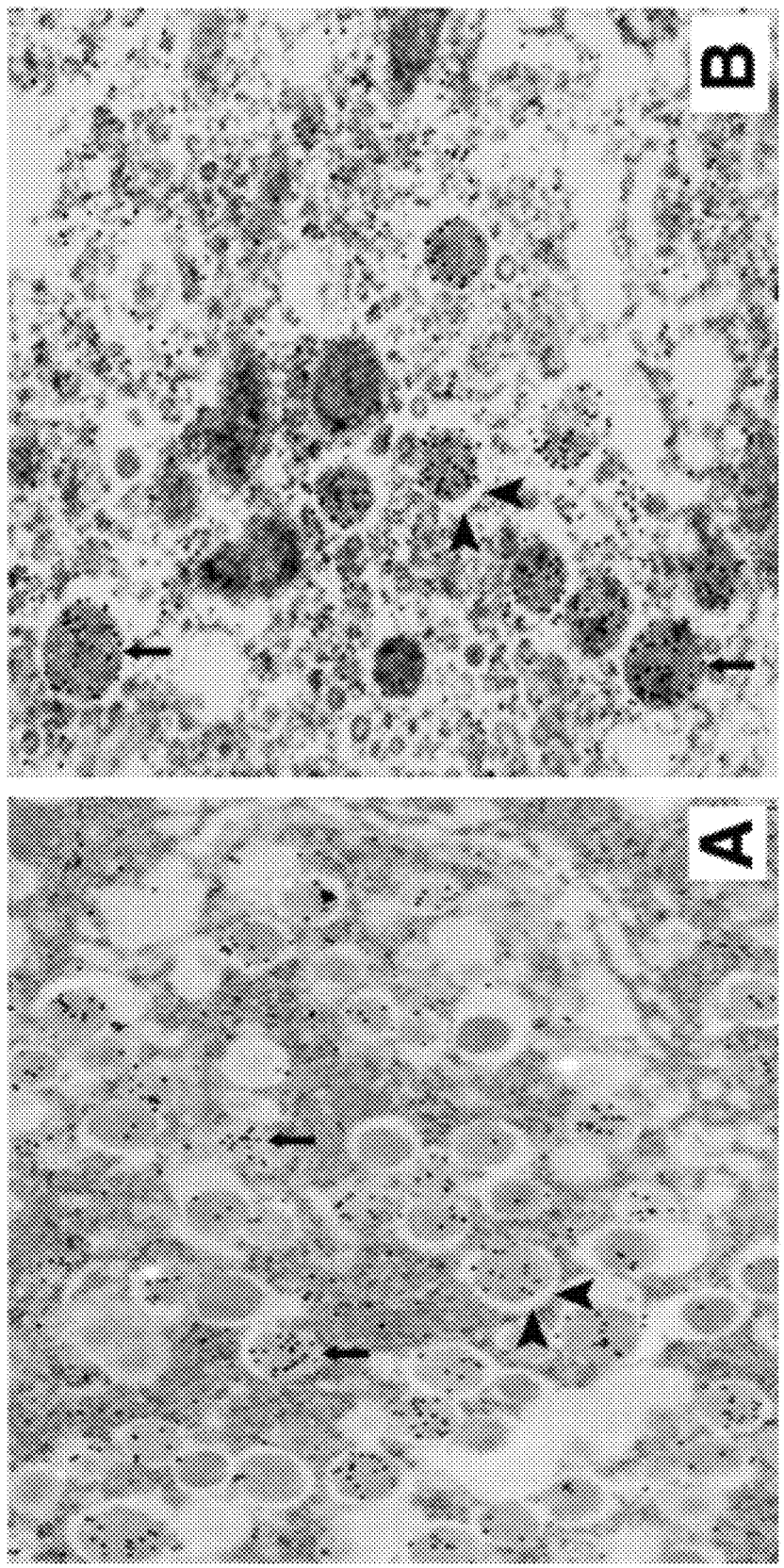
FIG. 12A-B shows that hepcidin was confined to secretory granules of the β-cells, where insulin is localized. The subcellular localization of hepcidin in normal human (A) and rat (B) pancreatic β-cells by immunoelectron microscopy. Within the β-cells, hepcidin immunoreactivity is exclusively confined to the secretory granules. Immunoreactivity for this peptide is accumulated in the dense core of the secretory granules (arrows); the electron-lucent halo of these granules exhibits no immunoreactivity for hepcidin (arrowheads). Electron micrograph (X 25,000).

At the subcellular level, hepcidin was confined to the typical secretory granules of the β-cells, where insulin is localized (FIG. 12A-B). Hepcidin immunoreactivity exhibited a distinct intragranular topology; the immunoreactivity for this peptide was absent in the electron-lucent halo but was confined to the dense core of the β-cell secretory granules, i.e., the compartment where insulin is also resident. Based on this granular co-segregation we assume that hepcidin is co-released with insulin upon glucose stimulation of β-cells. Hence, β-cells are not only involved in glucose homeostasis but may also regulate iron metabolism by secreting hepcidin and thus exert a dual function. Thereafter, we addressed the question of regulation of hepcidin expression and secretion by glucose and iron.

Hepcidin Expression in β-Cells is Regulated by Iron

RINM5F cells, rat insulinoma cells of the pancreas, exhibiting preserved β-cell features represent a suitable model for β-cell experiments.

RINM5F cells were grown in RPMI1640 media (PAA, Austria) containing L-glutamine, supplemented with 10% (vol/vol) heat inactivated fetal calf serum, penicillin (100 units/ml) and streptomycin (100 μg/mL). Cells were cultivated at 37° C. in 5% $CO_2$. Cells were incubated with increasing concentrations of FENTA from 1 μM up to 65 μM for 72 hours and with 100 mM glucose (Merck, Darstadt, Germany) for up to 8 hours. After stimulation experiments, total rna or proteins were extracted from RINM5F cells and analyzed by quantitative PCR and immunoblot assays.

RT-PCR analyses using the appropriate primer specifications and combinations successfully employed in the rat liver and pancreas identified expression of hepcidin in RINM5F cells (FIG. 9A-D). In analogy to the human and rat pancreas the amplification product in RINM5F cells was also of 201 bp which after sequencing revealed a complete homology to the rat hepcidin cDNA. The existence of the respective translated proteins in these cells was verified by immunocytochemistry and immunoblotting experiments using the region-specific hepcidin antisera (see FIGS. 13A-C and 14A-B).

The regulation of hepcidin expression in RINm5F cells was analyzed upon exposure to iron, since iron regulates hepcidin expression in the liver. The regulatory effect of iron on hepcidin gene expression was measured in these cells under various FENTA concentrations using quantitative RT-PCR as described, for example, in Gehrke et al., *Blood* 102: 371-376 (2003). A 2-step reverse transcriptase-polymerase chain reaction (RT-PCR) was performed using the Lightcycler system and relative quantification software version 1.0 (ROCHE Molecular Biochemicals; Mannheim, Germany). In a first step, cDNA synthesis was performed with the first strand cDNA synthesis kit for RT-PCR (ROCHE Molecular Biochemicals) according to manufacturer's instructions. In a second step, transcripts of hepcidin were amplified in duplicates with specific sense and antisense primers. all transcripts were detected using SYBR GREEN I according to manufacturer's instructions and were normalized to β-actin as internal control.

Under small amounts of iron, i.e., 1 μM up to 10 μM, a significant up-regulation of hepcidin-mRNA up to three-fold was observed in RINM5F cells (FIG. 13A), as is also the case in the liver. Remarkably, hepcidin expression was down-regulated when FENTA concentrations of 65 μM or higher were used, even if the concentrations of FENTA were not cytotoxic as shown in a neutral red assay (FIG. 13B). These results were confirmed by immunoblot analyses (FIG. 13C). In these experiments, protein extracts were incubated for 7 min at 94° C. in sample buffer with 4% (wt/vol) SDS (Merck, Darmstadt, Germany), 50 mM TRIS-HCl (PH 8.45), 1 mM EDTA, 3.24 mM dithiothreitol (ROTH, Karlsruhe, Germany), 12.5% (wt/vol) glycerol (Merck, Darmstadt, Germany), and 0.002% Bromophenol blue (Merck, Darmstadt, Germany). To detect hepcidin, a 16.5% Tricine-SDS-polyacrylamide gel was used. The immunoreaction on the western blot was specifically blocked after preincubation of the antibodies with the corresponding peptide immunogens. Cross reactivity with the second goat anti-rabbit antibody was excluded by appropriate controls (data not shown) Thus, these findings clearly show that hepcidin expression was regulated by FENTA not only at the transcriptional but also at the protein level.

Hepcidin Expression in β-Cells is Regulated by Glucose.

After providing evidence for expression and localization of hepcidin in β-cells we addressed the question of glucose-regulated hepcidin expression which was analyzed in RINM5F cells as prototypical of pancreatic β-cells. Treatment of RINM5F cells with 100 mM glucose resulted after two and four hours in a significant up to eightfold increase of hepcidin expression in these cells (FIG. 14A). This increase was reduced in the following 8 hours, but the level of hepcidin expression still remained higher than in the control cells with 10 mM glucose in the media. These findings were further confirmed by immunoblot assays (FIG. 14B). In contrast, experiments with HEPG2 cells revealed no change of hepcidin expression under glucose treatment (data not shown).

Regulation of Hepcidin Secretion into the Circulation by Glucose.

To analyze whether the experimental findings at the level of RINM5F cells are transferable to in vivo physiological regulatory pathways an oral glucose tolerance test in humans was performed to induce hepcidin secretion by increasing serum glucose levels. Healthy 10 persons started the test in a fasting state (having no food or drink for 12 hours). Initial blood sugar, insulin, and hepcidin were drawn and then the persons were given a glucose solution with 37.5 grams of glucose. The parameters were tested again 30 minutes and 1 hour after drinking the high glucose drink. For hepcidin measurements the hepcidin ELISA competitive binding assay was used. For that assay, blood samples were withdrawn into serum-tubes and centrifuged at 2,500×G for 10 min at 4° C. The measurements were performed by a hepcidin ELISA competitive binding assay using the antibody EG(2)-Hepn against hepcidin-(28-47), as disclosed, for example, in Kulaksiz, et al. *Gut.* 53: 735-743 (2004), Kulaksiz et al., *J. Endocrinol.* 184: 361-370 (2005) or Pietrangelo, et al., *Gastroenterology.* 128: 470-479 (2005). Determinations were performed in duplicate using 96-well-microtiter plates coated with 200 μl/well rabbit anti-hepcidin antibody EG(2)-Hepn diluted 1:4000 in TRIS buffered saline (TBS) containing 40 mM TRIS-HCL (PH 7.3), 100 mM NaCl. 50 μl standards containing various amounts of synthetic peptides (0, 20, 100, 500, and 1000 ng/ml) or human serum samples and 150 μL N-terminally biotinylated hepcidin-(28-47) (Peptide Specialty Laboratories GMBH, Heidelberg, Germany) (2 ng/well) were added to each well and incubated for 1 hour at RT. After washing with tbst (TBS WITH 0.05% TWEEN 20), the biotinylated antigen-antibody complexes were detected by streptavidin-peroxidase enzyme (DAKO, Hamburg, Germany) with the substrate tetramethylbenzidine (DRG INSTRUMENTS GMBH, Marburg, Germany); the color reaction was stopped with 1 m $H_2SO_4$ and the extinction of the solution was read at 450/630 nm wavelength.

Figure 15:
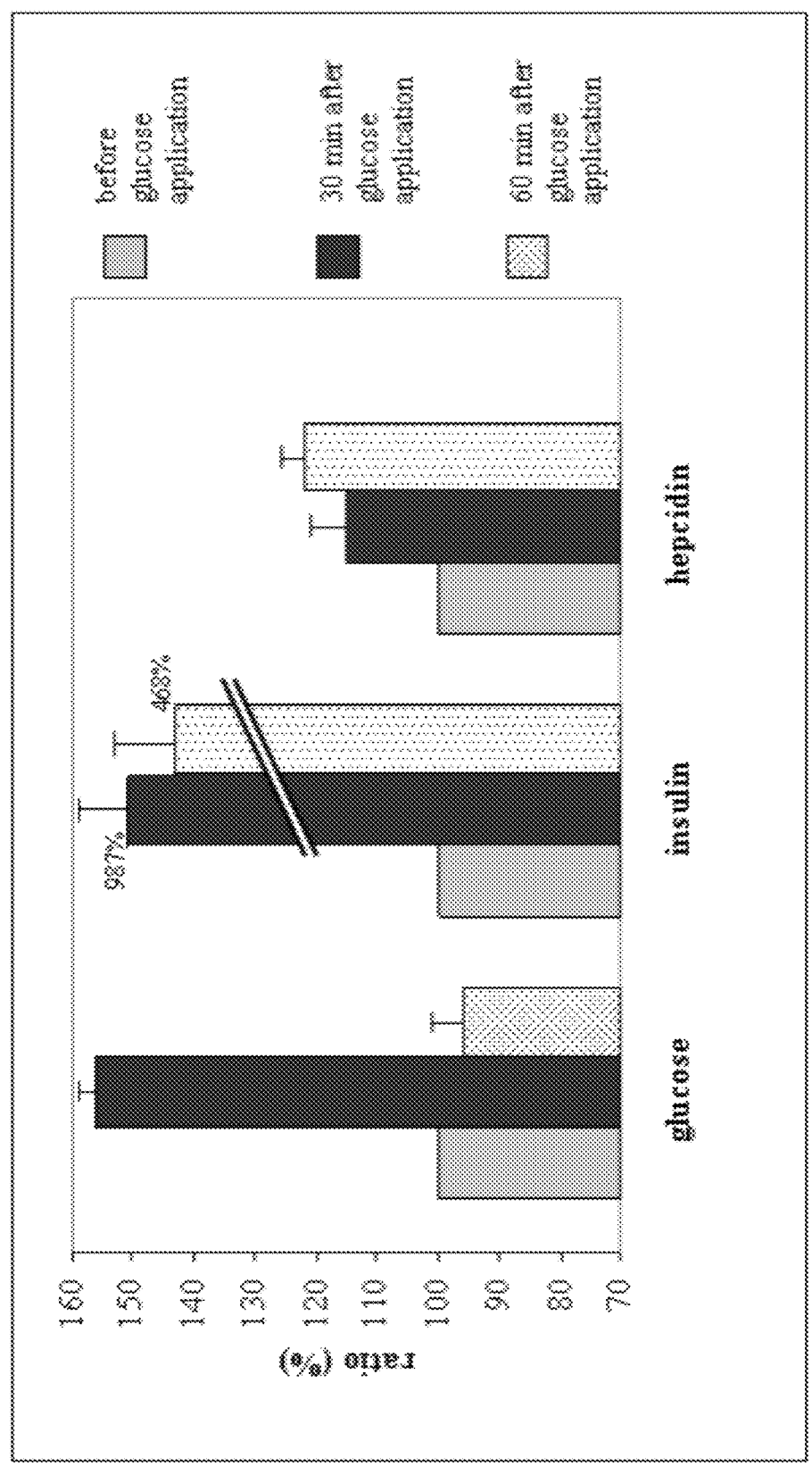
FIG. 15 shows that administration of glucose results in an increase of hepcidin secretion in blood serum. Serum glucose, insulin, and hepcidin levels before and 30 or 60 min after oral glucose tolerance test with 37.5 g glucose (n=10). Note the significant up-regulation of hepcidin after glucose administration (P<0.03).

This test revealed that 30 min and 60 min after oral glucose application the serum hepcidin levels increased significantly to 137 and 158% (FIG. 15). In the oral glucose tolerance test also insulin serum concentrations increased significantly parallel to hepcidin as expected; these data are in line with the co-localization of hepcidin and insulin in the same secretory granules of β-cells and confirmative for our thesis that both hormones are stimulated and co-secreted by glucose.

Expression of Ferroprtin in the Human and Rat Pancreas and in RINM5F Cells.

Figure 16:
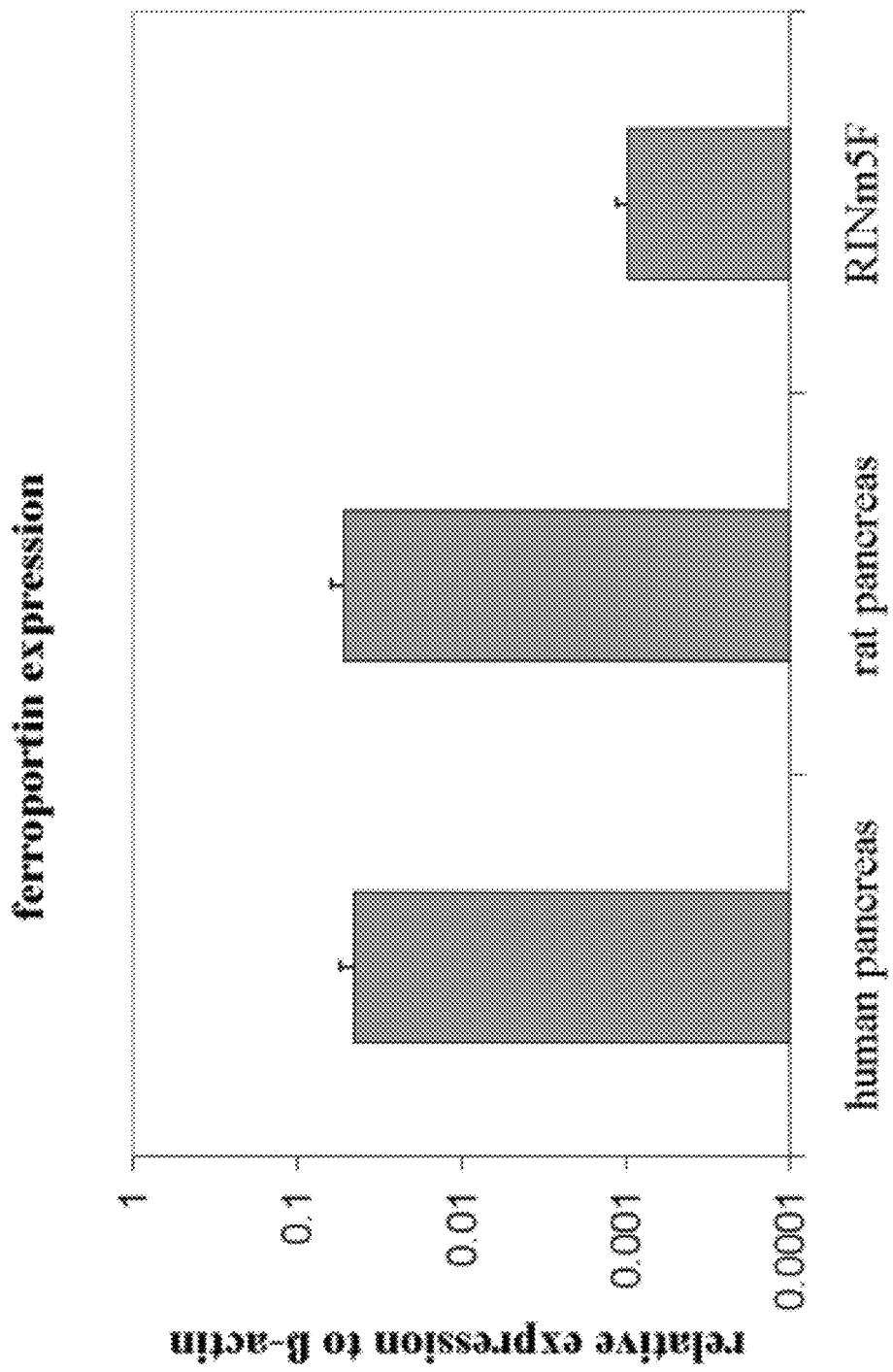
FIG. 16 shows quantitative RT-PCR for ferroportin (n=4). The expression levels of ferroportin (means) are given as the amount relative to the expression of the housekeeping gene actin in each sample. Ferroportin is highly expressed in human and rat pancreas, as well as in RINM5F cells.

RT-PCR analyses using specific primers revealed that not only hepcidin, but also ferroportin is highly expressed in human and rat pancreas, as well as in RINM5F cells (FIG. 16). The amplification yielded an expected transcript of 120 bp for rat ferroportin and 163 bp for human ferroportin. RNA isolation was performed using QIAGEN RNAEasy kit including DNA digestion. reverse transcription (RT)-PCR analysis was performed using the following primers and specifications given in 5'-3' orientation: rat ferroportin (Genbank database accession no. AF 394785), 5'-GCT AGA ATC GGT CTT TGG TCC-3' (SEQ ID NO:18) and 5'-ACC ATG ATG AAA TGC AGA AGG-3' (SEQ ID NO:19); corresponding to positions 1646-1666 and 1765-1745. Human ferroportin (Genbank database accession no. NM014585), 5'-CTT CAG CCT GGC AAG TTA CAT G-3'(SEQ ID NO:20) and 5'-TTC TCA AAG GCA TTT GAA AGG G-3'(SEQ ID NO:21); corresponding to positions 2992-3013 and 3154-3133. sequence analyses of the amplification products confirmed complete homology with the ferroportin cDNAs of rat and man. immunohistochemical studies using an antiserum against ferroportin localized the protein in islet cells that were also immunoreactive for insulin and hepcidin (data not shown).

Monoclonal Antibodies of the Instant of the Invention are Capable of Inactivating Hepcidin cR293 cells were stably transfected with a plasmid containing an ecdysone-regulated Ferroportin-GFP (Fpn-GFP) construct. In resulting HEK293-Fpn cells bioactive hepcidin binds to ferroportin and specifically induces the internalization of Fpn-GFP. Briefly, Fpn-GFP was induced by ponasterone treatment for 24 h. Cells were then incubated with 0.1 to 0.5 μM purified human hepcidin (from urine) for 6 h and imaged by epi-fluorescence microscopy.

Addition of hepcidin to Fpn-GFP expressing cells changed the distribution of Fpn-GFP from the cell surface to punctuate intracellular vesicles. When hepcidin was absent from the medium, there was no internalization of Fpn-GFP.

Concentrations of hepcidin as low as 0.1 μM induced Fpn internalization within 1 h. We synthesized hepcidin chemically and performed the same experiments. Chemically synthesized hepcidin was as efficient in inducing Fpn-GFP internalization as hepcidin purified from urine.

Addition of monoclonal hepcidin antibodies, detecting hepcidin specifically, showed no change of the localization of cell surface Fpn-GFP. In the presence of monoclonal hepcidin antibodies, which bind to hepcidin in the medium, no internalization of Fpn-GFP by hepcidin was observed.

These data clearly show that the monoclonal antibodies exemplified herein specifically bind to and inactivate hepcidin.

Monoclonal Antibodies which Bind SEQ. ID. NO. 3 are Suitable for use in Elisa foe the Mature 20-25 Amino Acid Long Form of Hepcidin The invention provides sensitive diagnostic methods and kits enabling the detection of hepcidin in human plasma, urine and other body fluids. The invention opens a broad range of therapeutic perspectives, where a hepcidin antibody and diagnostic methods and kits can be used for the determination of hepcidin as a parameter for the progress of the diseases mentioned above during and after therapy.

At least two different assay versions can be designed for qualitative determination of a mature 20-25 amino acid long form of hepcidin (preferably, 25 amino acid long form) in human serum or urine.

Version 1:

96 well microtiter plate was coated with Goat anti Mouse (150 μl/well) and is stabilized with phosphate buffer pH 7.2, containing sucurose and BSA.

Assay Performance is as Follows:
1. 100 μl monoclonal Mouse anti-Hepcidin 25 antibody (diluted 1:5000 in Stabilzyme Select (SurModics) was pipetted into the microtiterplate wells and is incubated for 1 h at room temperature.
2. The content of the plate was discarded and the wells were washed with 3×400 μl wash buffer in order to remove unbound antibodies.
3. 50 μl standard or sample were pipetted into the wells. The standards are produced by diluting the stock standard 2 μg/μl with Stabilzyme Select (SurModics) to the following final concentrations:
   333 ng/ml
   37.0 ng/ml
   12.3 ng/ml
   4.1 ng/ml
   0.0 ng/ml
   50 μl conjugate (biotinilylated HRSK peptide) concentration of 0.05 ng/ml diluted in 0.25 M Tris Buffer pH 9.5, which contains 0.2% Tween 20, were added into the wells. The contents of the wells was mixed by a brief shaking of the plate and then incubated for 1 h at room temperature.
4. The content of the plate was discarded and the wells are washed with 3×400 μl wash buffer in order to remove unbound material.
5. 100 μl enzyme complex, Streptavidin HRP (DAKO) diluted 1:5000 in Stabilzyme HRP (SurModics) were pipetted into the wells and then incubated for 30 minutes at room temperature.
6. The content of the plate was discarded and the wells are washed with 3×400 μl wash buffer in order to remove unbound material.
7. 100 μl TMB (BioFX) was pipetted into the wells of the microtiterplate and was incubated for 20 minutes. The enzymatic reaction was stopped by addition of 100 μl 05M $H_2SO_4$. Optical Density was measured by an ELISA reader at an Optical Density of 450 nm and a 640 nm reference wavelength.

Figure 17A:
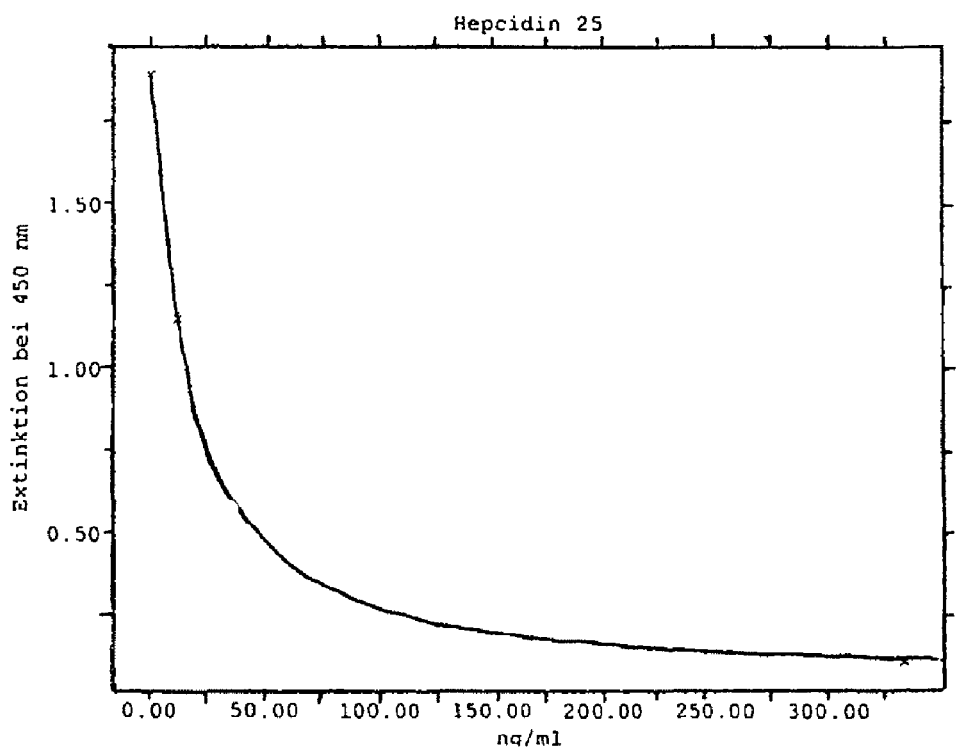
FIGS. 17A, 17B, and 17C show standard curves of ELISA for a 25 amino acid long form of hepcidin using the antibodies binding to SEQ ID NO:3, according to a first (A), (C) and a second (B) version of the assay, respectively.

An example of a typical standard curve for the Hepcidin-25 Assay Version 1 is shown in FIG. 17A.

Version 2:

96 well microtiter plate was coated with Avidin (150 μl/well) and stabilized with Stabilcoat (SurModics).

Assay Performance is as Follows:
1. 100 μl biotinylated peptide (HRSK-biotin) in concentration 0.1 ng/ml diluted in Stabilzyme Select (SurModics) was pipetted into the microtiterplate wells and is incubated for 30 min at room temperature.
2. The content of the plate was discarded and the wells were washed with 3×400 μl wash buffer in order to remove the unbound peptide-conjugate.
3. 50 μl standard or samples were pipetted into the wells. The standards are produced by diluting the stock standard 2 μg/ul with Stabilzyme Select (SurModics) to the following final concentrations:
   333 ng/ml
   37.0 ng/ml
   12.3 ng/ml
   4.1 ng/ml
   0.0 ng/ml
   50 μl of the monoclonal mouse anti-Hepcidin diluted 1:5000 in 0.25 M Tris Buffer pH 9.5, which contains 0.2% Tween 20, were added into the wells. The contents of the wells is mixed by a brief shaking of the plate and then incubated for 1 h at room temperature.
4. The content of the plate was discarded and the wells were washed with 3×400 μl wash buffer in order to remove unbound material.
5. 100 μl of Goat a Mouse HRP Complex (Pierce) diluted 1:5000 in Stabilzyme HRP (SurModics) were pipetted into the wells and then incubated for 30 minutes at room temperature.
6. The content of the plate was discarded and the wells were washed with 3×400 μl wash buffer in order to remove unbound material.
7. 100 μl TMB (BioFX) was pipetted into the wells of the microtiterplate and was incubated for 20 minutes. The enzymatic reaction is stopped by addition of 100 ul 0.5M $H_2SO_4$. Optical Density was measured by an ELISA reader at an Optical Density of 450 nm and a 640 nm reference wavelength.

Figure 17B:
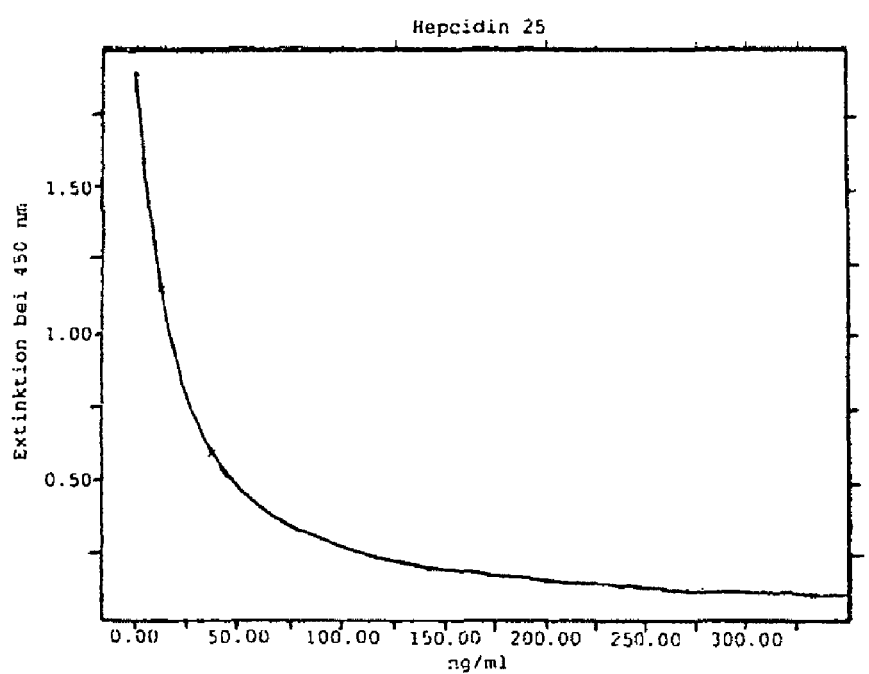

An example of a typical standard curve for the Hepcidin-25 Assay Version 2 is shown in FIG. 17B.

Figure 17C:
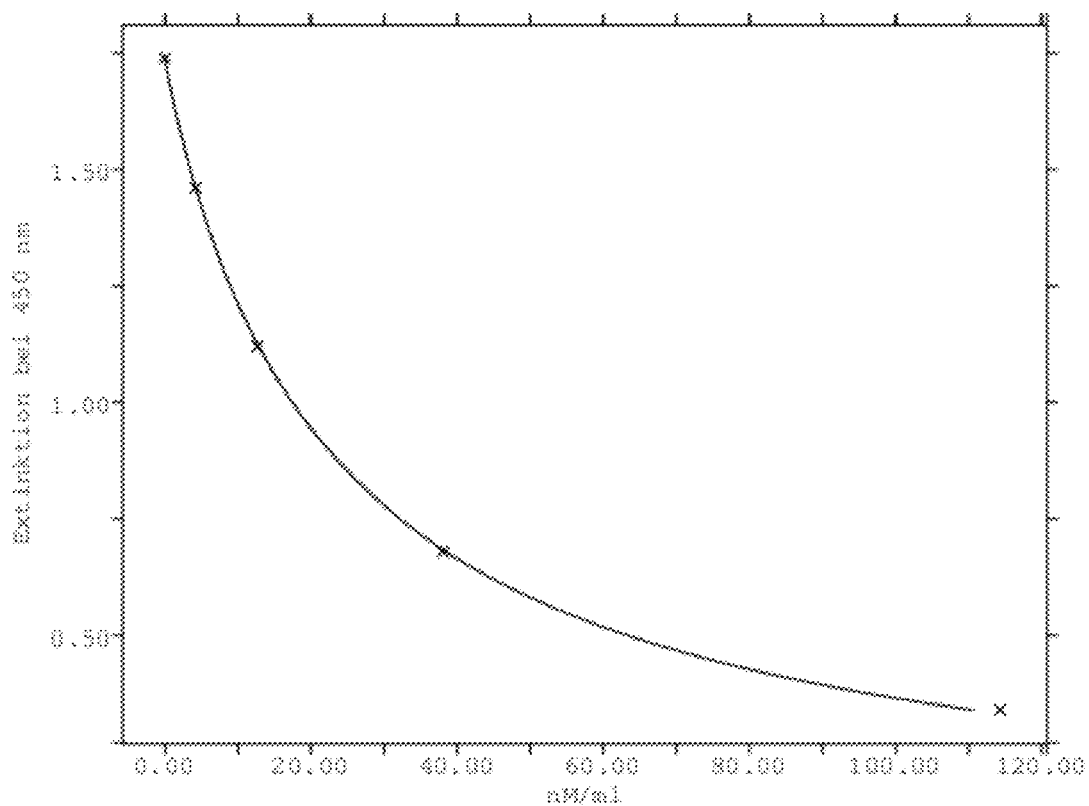

Version 1A:

A variation on Version 1 is also presented, as Version 1A. An example of standard curve is shown in FIG. 17C.

A 96 well microtiter plate is coated with Goat anti Mouse (150 μl/well) and is stabilized with phosphate buffer pH 7.2, containing sucurose and BSA.

Assay Performance is as Follows:
1. 50 μl monoclonal Mouse anti-Hepcidin 25 antibody (diluted 1:3000 in Stabilzyme Select (SurModics) is pipetted into the microtiterplate wells and is incubated for 1 h at room temperature.
2. The content of the plate is discarded and the wells are washed with 3×400 μl wash buffer in order to remove unbound antibodies.
3. 200 μl standard or sample are pipetted into the wells.

The standards are produced by diluting the stock standard 2 µg/µl with Stabilzyme Select (SurModics) to the following final concentrations:

| Fragment MW 903 | Hepcidin 25 MW 2789 |
|---|---|
| 37.0 ng/m | 114.3 nM/ml |
| 12.3 ng/ml | 38.1 nM/ml |
| 4.1 ng/ml | 12.7 nM/ml |
| 1.4 ng/ml | 4.2 nM/ml |
| 0.0 ng/ml | 0.0 nM/ml |

4. 100 µl conjugate (biotinilylated HRSK peptide) concentration of 0.05 ng/ml diluted in 0.5 M Tris Buffer pH 9.5, which contains 0.2% Tween 20 and 10 mM EDTA are added into the wells. The contents of the wells is mixed by a brief shaking of the plate and then incubated for 3 h at room temperature.
5. The content of the plate is discarded and the wells are washed with 3×400 µl wash buffer in order to remove unbound material.
6. 50 µl enzyme complex, Streptavidin HRP (DAKO) diluted 1:5000 in Stabilzyme HRP (SurModics) are pipetted into the wells and then incubated for 30 minutes at room temperature.
7. The content of the plate is discarded and the wells are washed with 3×400 µl wash buffer in order to remove unbound material.
8. 50 µl TMB (BioFX) is pipetted into the wells of the microtiterplate and is incubated for 20 minutes. The enzymatic reaction is stopped by addition of 50 µl 05M $H_2SO_4$.
9. Optical Density is measured by an ELISA reader at an Optical Density of 450 nm and a 640 nm reference wavelength.

INDUSTRIAL APPLICABILITY

The invention has applications in connection with diagnosing a disease condition characterized by non-physiological levels of hepcidin protein, including prohepcidin and fragments thereof.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

All patent and non-patent publications cited in this specification are indicative of the level of skill of those skilled in the art to which this invention pertains. All these publications and patent applications are herein incorporated by reference to the same extent as if each individual publication or patent application was specifically and individually indicated to be incorporated herein by reference.

What is claimed is:

1. A method of producing a monoclonal antibody which specifically binds to one or more epitopes within SEQ. ID. NO. 4, comprising:
   immunizing a mammal with a peptide comprising the amino acid sequence of SEQ. ID. NO. 4;
   harvesting B-cells of said mammal;
   creating hybridomas from the harvested B-cells, wherein said hybridomas produce antibodies; and,
   selecting hybridomas which produce antibodies specifically binding to one or more epitopes within SEQ. ID. NO. 4, wherein the antibodies are able to identify hepcidin in an enzyme linked immunosorbent assay (ELISA).

2. The method of claim 1, wherein X of SEQ ID NO:4 is an alpha aminobutyric acid.

3. The method of claim 1, wherein X of SEQ ID NO:4 is a cysteine (Cys).

4. The method of claim 1, wherein the immunizing step is conducted by administering to the mammal the peptide and an adjuvant.

5. The method of claim 1, wherein the mammal is a non-human mammal.

6. The method of claim 5, wherein the mammal is a horse, a cow, a rabbit, a mouse, or a rat.

7. The method of claim 1, wherein the peptide consists of the amino acid sequence of SEQ. ID. NO. 4.

* * * * *

```
                      SEQUENCE LISTING

<160> NUMBER OF SEQ ID NOS: 20

<210> SEQ ID NO 1
<211> LENGTH: 40
<212> TYPE: PRT
<213> ORGANISM: Homo sapiens

<400> SEQUENCE: 1

Cys Leu Leu Leu Leu Leu Leu Leu Ala Ser Leu Thr Ser Gly Ser Val
1               5                   10                  15

Phe Pro Gln Gln Thr Gly Gln Leu Ala Glu Leu Gln Pro Gln Asp Arg
            20                  25                  30

Ala Gly Ala Arg Ala Ser Trp Met
        35                  40

<210> SEQ ID NO 2
<211> LENGTH: 25
<212> TYPE: PRT
<213> ORGANISM: Homo sapiens

<400> SEQUENCE: 2

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 3
<211> LENGTH: 8
<212> TYPE: PRT
<213> ORGANISM: Homo sapiens

<400> SEQUENCE: 3
```

His Arg Ser Lys Cys Gly Met Cys
1               5

<210> SEQ ID NO 4
<211> LENGTH: 8
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Xaa is any known amino acid, including L or D
      stereoisomeric forms of the 20 common amino acids, as well as any
      modified or unusual amino acid, including alpha aminobutryic acid

<400> SEQUENCE: 4

His Arg Ser Lys Xaa Gly Met Cys
1               5

<210> SEQ ID NO 5
<211> LENGTH: 8
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Xaa is alpha aminobutryic acid

<400> SEQUENCE: 5

His Arg Ser Lys Xaa Gly Met Cys
1               5

<210> SEQ ID NO 6
<211> LENGTH: 430
<212> TYPE: DNA
<213> ORGANISM: Homo sapiens

<400> SEQUENCE: 6
gactgtcact cggtcccaga caccagagca agctcaagac ccagcagtgg gacagccaga      60
cagacggcac gatggcactg agctcccaga tctgggccgc ttgcctcctg ctcctcctcc     120
tcctcgccag cctgaccagt ggctctgttt tcccacaaca gacgggacaa cttgcagagc     180
tgcaacccca ggacagagct ggagccaggg ccagctggat gcccatgttc agaggcgaa      240
ggaggcgaga cacccacttc cccatctgca ttttctgctg cggctgctgt catcgatcaa     300
agtgtgggat gtgctgcaag acgtagaacc tacctgccct gccccgtcc cctcccttcc     360
ttatttattc ctgctgcccc agaacatagg tcttggaata aatggctgg ttcttttgtt      420
ttccaaaaaa                                                            430

<210> SEQ ID NO 7
<211> LENGTH: 84
<212> TYPE: PRT
<213> ORGANISM: Homo sapiens

<400> SEQUENCE: 7

Met Ala Leu Ser Ser Gln Ile Trp Ala Ala Cys Leu Leu Leu Leu
1               5                   10                  15

Leu Leu Ala Ser Leu Thr Ser Gly Ser Val Phe Pro Gln Gln Thr Gly
            20                  25                  30

Gln Leu Ala Glu Leu Gln Pro Gln Asp Arg Ala Gly Ala Arg Ala Ser
        35                  40                  45

Trp Met Pro Met Phe Gln Arg Arg Arg Arg Asp Thr His Phe Pro
    50                  55                  60

Ile Cys Ile Phe Cys Cys Gly Cys Cys His Arg Ser Lys Cys Gly Met

```
                65                  70                  75                  80
Cys Cys Lys Thr

<210> SEQ ID NO 8
<211> LENGTH: 20
<212> TYPE: PRT
<213> ORGANISM: Homo sapiens

<400> SEQUENCE: 8

Pro Gln Gln Thr Gly Gln Leu Ala Glu Leu Gln Pro Gln Asp Arg Ala
1               5                   10                  15

Gly Ala Arg Ala
            20

<210> SEQ ID NO 9
<211> LENGTH: 15
<212> TYPE: PRT
<213> ORGANISM: Homo sapiens

<400> SEQUENCE: 9

Cys Gly Cys Cys His Arg Ser Lys Cys Gly Met Cys Cys Lys Thr
1               5                   10                  15

<210> SEQ ID NO 10
<211> LENGTH: 19
<212> TYPE: DNA
<213> ORGANISM: Homo sapiens

<400> SEQUENCE: 10
ctgcaacccc aggacagag                                                  19

<210> SEQ ID NO 11
<211> LENGTH: 23
<212> TYPE: DNA
<213> ORGANISM: Homo sapiens

<400> SEQUENCE: 11
ggaataaata aggaagggag ggg                                             23

<210> SEQ ID NO 12
<211> LENGTH: 20
<212> TYPE: DNA
<213> ORGANISM: Homo sapiens

<400> SEQUENCE: 12
gattcagggt cagggaggtg                                                 20

<210> SEQ ID NO 13
<211> LENGTH: 20
<212> TYPE: DNA
<213> ORGANISM: Homo sapiens

<400> SEQUENCE: 13 gaagggctg tgattgaagg                                                  20

<210> SEQ ID NO 14
<211> LENGTH: 17
<212> TYPE: DNA
<213> ORGANISM: Homo sapiens

<400> SEQUENCE: 14
gaccagtggc tctgttt                                                    17
```

```
<210> SEQ ID NO 15
<211> LENGTH: 20
<212> TYPE: DNA
<213> ORGANISM: Homo sapiens

<400> SEQUENCE: 15
ggttctacgt cttgcagcac                                                 20

<210> SEQ ID NO 16
<211> LENGTH: 22
<212> TYPE: DNA
<213> ORGANISM: Homo sapiens

<400> SEQUENCE: 16
ggcagaaagc aagactgatg ac                                              22

<210> SEQ ID NO 17
<211> LENGTH: 21
<212> TYPE: DNA
<213> ORGANISM: Homo sapiens

<400> SEQUENCE: 17
acaggaataa ataatggggc g                                               21

<210> SEQ ID NO 18
<211> LENGTH: 21
<212> TYPE: DNA
<213> ORGANISM: Homo sapiens

<400> SEQUENCE: 18
gctagaatcg gtctttggtc c                                               21

<210> SEQ ID NO 19
<211> LENGTH: 21
<212> TYPE: DNA
<213> ORGANISM: Homo sapiens

<400> SEQUENCE: 19
accatgatga aatgcagaag g                                               21

<210> SEQ ID NO 20
<211> LENGTH: 22
<212> TYPE: DNA
<213> ORGANISM: Homo sapiens

<400> SEQUENCE: 20
cttcagcctg gcaagttaca tg                                              22
```